United States Patent
Wong et al.

(10) Patent No.: US 9,840,542 B2
(45) Date of Patent: Dec. 12, 2017

(54) METHODS AND COMPOSITIONS FOR THE PACKAGING OF NUCLEIC ACIDS INTO MICROGLIAL EXOSOMES FOR THE TARGETED EXPRESSION OF POLYPEPTIDES IN NEURAL CELLS

(71) Applicant: Nomadogen Biotechnologies Inc., Calgary (CA)

(72) Inventors: Scott Allan Wong, Lethbridge (CA); Zakery Kevin Stinson, Regina (CA); Aubrey Marissa Demchuk, Lethbridge (CA); Evan Anthony Caton, Lethbridge (CA)

(73) Assignee: Nomadogen Biotechnologies Inc., Calgary, Alberta (CA)

( * ) Notice: Subject to any disclaimer, the term of this patent is extended or adjusted under 35 U.S.C. 154(b) by 0 days.

(21) Appl. No.: 15/259,797

(22) Filed: Sep. 8, 2016

(65) Prior Publication Data

US 2017/0073382 A1    Mar. 16, 2017

Related U.S. Application Data

(60) Provisional application No. 62/217,137, filed on Sep. 11, 2015.

(51) Int. Cl.
| | |
|---|---|
| *A61K 9/00* | (2006.01) |
| *C07K 14/47* | (2006.01) |
| *C07K 14/705* | (2006.01) |
| *C12N 5/0793* | (2010.01) |
| *A61K 38/00* | (2006.01) |

(52) U.S. Cl.
CPC .... *C07K 14/4705* (2013.01); *C07K 14/70596* (2013.01); *C12N 5/0619* (2013.01); *A61K 38/00* (2013.01); *C07K 2319/03* (2013.01); *C07K 2319/055* (2013.01); *C07K 2319/09* (2013.01); *C07K 2319/33* (2013.01); *C07K 2319/50* (2013.01); *C07K 2319/60* (2013.01); *C07K 2319/80* (2013.01); *C12N 2501/60* (2013.01); *C12N 2506/08* (2013.01)

(58) Field of Classification Search
CPC .... A61K 9/00; A61K 48/005; C07K 2319/03; C07K 2319/33; C07K 2319/50; C07K 2319/80; C12N 5/0619; C12N 5/0622; C12N 2501/60
See application file for complete search history.

(56) References Cited

U.S. PATENT DOCUMENTS

| | | | |
|---|---|---|---|
| 7,704,964 B2 | 4/2010 | Delcayre et al. | |
| 2013/0053426 A1* | 2/2013 | Seow | A61K 48/0025 514/44 A |
| 2014/0024599 A1 | 1/2014 | Chen et al. | |
| 2014/0274812 A1* | 9/2014 | Joung | C12P 19/34 506/26 |
| 2014/0308340 A1 | 10/2014 | Chang et al. | |
| 2015/0093433 A1 | 4/2015 | Leonard et al. | |
| 2015/0315252 A1* | 11/2015 | Haugwitz | C12N 9/22 530/350 |

FOREIGN PATENT DOCUMENTS

| | | |
|---|---|---|
| CA | 2658180 A1 | 1/2008 |

OTHER PUBLICATIONS

NDF1_Human; Genbank Q13562, Nov. 1, 1997.*
Genbank JC4317, Jul. 9, 2004.*
Genbank Q85422_9RHAB, Nov. 1, 1996.*
Alvarez-Erviti, L. et al., (2011). Delivery of siRNA to the mouse brain by systemic injection of targeted exosomes. Nature Biotechnology, 29, 341-347.
Choudhury, G.R. and Shinghua, D. (2016). Reactive astrocytes and therapeutic potential in focal ischemic stroke. Neurobiology of Disease, 85, 234-44.
Guo, Z. et al. (2014). In vivo direct reprogramming of reactive glial cells into functional neurons after brain injury and in an Alzheimer's disease model. Cell Stem Cell, 14, 188-202.
Lee, Y. et al. (2008). GFAP promoter elements required for region-specific and astrocyte-specific expression. Glia, 56, 481-493.
Sanjana, N.E. et al. (2012). A transcription activator-like effector (TALE) toolbox for genome engineering. Nat Protoc., 7(1), 171-192.
Tanaka, R., et al. (2003). Migration of enhanced green fluorescent protein expressing bone marrow-derived microglia/macrophage into the mouse brain following permanent focal ischemia. Neuroscience, 117(3), 531-539.
Poster titled 'Nomadocytes: Engineering Microglia for Neural Cell Therapy', at the IGEM (international Genetically Engineered Machines) World Jamboree, Boston, MA (Oct. 30-Nov. 4, 2014).
Powerpoint document titled "Nomadocytes: Engineering Microglia for Neural Cell Therapy", at the IGEM (international Genetically Engineered Machines) World Jamboree, Boston, MA (Oct. 30-Nov. 4, 2014).

* cited by examiner

*Primary Examiner* — Kevin K Hill
(74) *Attorney, Agent, or Firm* — Bereskin & Parr LLP/S.E.N.C.R.L., s.r.l.; Micheline Gravelle

(57) ABSTRACT

Methods for expressing a polypeptide of interest in an astroglial cell. The methods permit the localization and transport of nucleic acids in microglial exosomes, the reprogramming of astroglial cells to neuronal cells, and the treatment of ischemic stroke or traumatic brain injury patients.

21 Claims, 8 Drawing Sheets

METHODS AND COMPOSITIONS FOR THE PACKAGING OF NUCLEIC ACIDS INTO MICROGLIAL EXOSOMES FOR THE TARGETED EXPRESSION OF POLYPEPTIDES IN NEURAL CELLS

RELATED APPLICATION

This application claims benefit of 35. U.S.C. 119 based on priority of U.S. Provisional Patent Application No. 62/217,137 filed on Sep. 11, 2015, which is incorporated herein by reference in its entirety.

INCORPORATION OF SEQUENCE LISTING

A computer readable form of the Sequence Listing "21806-P49086US01_SequenceListing.txt" (122,880 bytes), submitted via EFS-WEB and created on Sep. 7, 2016 and amended on Nov. 10, 2016, is herein incorporated by reference.

FIELD OF THE DISCLOSURE

The present disclosure relates to neural cells, notably astroglial cells, microglial cells, and neuronal cells. The present disclosure further relates to methods for the modification of microglial exosomes to package and deliver nucleic acid molecules, expression of polypeptides in neural cells, and to methods of replenishing damaged or destroyed neuronal cells.

BACKGROUND OF THE DISCLOSURE

The following paragraphs are provided by way of background to the present disclosure. They are not however an admission that anything discussed therein is prior art or part of the knowledge of persons skilled in the art.

It is estimated that traumatic brain injury (TBI) and stroke collectively cost the Canadian and American medical systems 110 billion dollars annually (Finkelstein, Corso, and Miller, 2006; Heidenreich et al., 2011; Public Health Agency of Canada, 2009). Both TBI and ischemic stroke are characterized by the death of neural tissues, which initiates a molecular signaling cascade that induces the formation of astroglial scar tissue that protects surrounding tissue from further damage. However, this scar tissue can also inhibit neuronal regrowth or regeneration, and thus functional recovery. Currently, ischemic stroke therapies are directed at emergency care, notably at dissolving or removing blood clots. While these immediate care stroke treatments substantially limit the acute neural damage to a stroke patient by targeting the direct causal agent, and while these known treatments, if initiated in a timely manner, save lives, they are not effective in regenerating injured or destroyed neuronal cells. Hence stroke symptoms, such as cognitive, motor, and memory impairments, are commonly experienced by surviving stroke patients, and are frequently permanent. It is therefore desirable to develop effective medical therapies that replace damaged or destroyed neurons, or reduce the inhibitory astroglial scar to promote recovery and alleviate these functional deficits. The efficacy of the heretofore known therapeutic methodologies to restore neurons and astroglial scar is limited. Therefore there exists a need in the art for methods to restore functional neurons following stroke or TBI.

SUMMARY OF THE DISCLOSURE

The following paragraphs are intended to introduce the reader to the more detailed description that follows and not to define or limit the claimed subject matter of the present disclosure.

In one aspect, the present disclosure relates to neural cells, including microglial cells, neuronal cells, and astroglial cells.

In another aspect, the present disclosure relates to methods for the expression of polypeptides of interest in neural cells.

In another aspect, the present disclosure relates to methods for the reprogramming of astroglial cells into neuronal cells.

In another aspect, the present disclosure provides, in at least one embodiment, a method of expressing a polypeptide of interest in an astroglial cell, the method comprising:
  a) introducing a first and second chimeric nucleic acid sequence in a microglial host cell, the first chimeric nucleic acid sequence comprising as operably linked components:
    (i) a nucleic acid sequence encoding an exosomal membrane polypeptide;
    (ii) a nucleic acid sequence encoding a neural cell targeting polypeptide; and
    (iii) a nucleic acid sequence encoding a nucleic acid binding polypeptide capable of binding a nucleic acid binding polypeptide recognition sequence; and
  the second chimeric nucleic acid sequence comprising as operably linked components:
    (i) a nucleic acid binding polypeptide recognition sequence; and
    (ii) a nucleic acid sequence encoding a polypeptide of interest;
  (b) growing the microglial host cell to produce exosomes;
  (c) delivering the exosomes to an astroglial cell; and
  (d) expressing the polypeptide of interest in the astroglial cell.

In some embodiments, the first chimeric nucleic acid sequence may further additionally comprise one or more of the following:
  (iv) a nucleic acid sequence encoding a cleavable polypeptide; and
  (v) a nucleic acid sequence encoding a polypeptide providing a signal for nuclear localization in the astroglial cell.

In some embodiments, the exosomes are produced in microglia cells in vitro. In such embodiments, the exosomes may be separated from the microglia cells and provided to a human or an animal in need thereof.

In some embodiments, the exosomes are produced in microglia cells in vivo. In such embodiments, the microglia cells may be provided to a human or an animal in need thereof.

In some embodiments, the polypeptide of interest is a protein capable of reprogramming astroglial cells into neuronal cells.

In some embodiments, the polypeptide of interest is NeuroD1.

In another aspect, the present disclosure provides microglia cells capable of producing exosomes, wherein the exosomes comprise:
  (I) a chimeric polypeptide comprising as operably linked components:
    (i) an exosomal membrane polypeptide;
    (ii) a neural cell targeting polypeptide; and (iii) a nucleic acid binding polypeptide capable of binding a nucleic acid binding polypeptide recognition sequence; and
(II) a chimeric nucleic acid sequence comprising as operably linked components:
(i) a nucleic acid binding polypeptide recognition sequence; and
(ii) a nucleic acid sequence encoding a polypeptide of interest.

In another aspect, the present disclosure provides microglia cells capable of producing exosomes, wherein the exosomes comprise:
(I) a chimeric polypeptide encoded by a first chimeric nucleic acid sequence; and
(II) a second chimeric nucleic acid sequence:
(a) the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
(b) the second chimeric nucleic acid sequence comprising as operably linked components:
(i) a nucleic acid binding polypeptide recognition sequence; and
(ii) a nucleic acid sequence encoding a polypeptide of interest.

In another aspect, the present disclosure provides a preparation comprising substantially pure exosomes comprising:
(I) a chimeric polypeptide comprising as operably linked components:
(i) an exosomal membrane polypeptide;
(ii) a neural cell targeting polypeptide; and
(iii) a nucleic acid binding polypeptide capable of binding a nucleic acid binding polypeptide recognition sequence; and
(II) a chimeric nucleic acid sequence comprising as operably linked components:
(i) a nucleic acid binding polypeptide recognition sequence; and
(ii) a nucleic acid sequence encoding a polypeptide of interest.

In another aspect, the present disclosure provides a preparation comprising substantially pure microsomes comprising:
(I) a chimeric polypeptide encoded by a first chimeric nucleic acid sequence; and
(II) a second chimeric nucleic acid sequence:
(a) the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
(b) the second chimeric nucleic acid sequence comprising as operably linked components:
(i) a nucleic acid binding polypeptide recognition sequence; and
(ii) a nucleic acid sequence encoding a polypeptide of interest.

In another aspect, the present disclosure provides a method for reprogramming astroglial cells into neuronal cells, the method comprising:
introducing a first and second chimeric nucleic acid sequence in a microglial host cell, the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
the second chimeric nucleic acid sequence comprising as operably linked components:
(i) a nucleic acid binding polypeptide recognition sequence; and
(ii) a nucleic acid sequence encoding a polypeptide capable of reprogramming astroglial cells into neuronal cells;
(b) growing the microglial host cell to produce exosomes;
(c) delivering the exosomes to an astroglial cell; and
(d) expressing the polypeptide to reprogram astroglial cells into neuronal cells in the astroglial cell.

In another aspect, the present disclosure provides a transgenic microglial cell line, wherein the microglial cells have been obtained by:
introducing a chimeric nucleic acid sequence into the genome of a microglial host cell, the chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence.

In another aspect, the present disclosure provides a transgenic animal comprising transgenic astroglial cells in which a protein of interest is expressed, wherein the transgenic astroglial cells have been obtained by:
introducing a first and second chimeric nucleic acid sequence in a microglial host cell, the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
the second chimeric nucleic acid sequence comprising as operably linked components:
(i) a nucleic acid binding polypeptide recognition sequence; and
(ii) a nucleic acid sequence encoding a polypeptide of interest;
(b) growing the microglial host cell to produce exosomes;
(c) delivering the exosomes to an astroglial cell; and
(d) expressing the polypeptide of interest in the astroglial cell.

In yet another aspect, the present disclosure provides a transgenic animal comprising transgenic astroglial cells wherein the transgenic astroglial cells comprise a chimeric nucleic acid sequence comprising:
(i) a nucleic acid binding polypeptide recognition sequence; and
(ii) a nucleic acid sequence encoding a polypeptide of interest.

In yet another aspect, the present disclosure provides a use of exosomes to treat a person in need thereof wherein the exosomes comprise:
(I) a chimeric polypeptide comprising as operably linked components:
(i) an exosomal membrane polypeptide;
(ii) a neural cell targeting polypeptide; and
(iii) a nucleic acid binding polypeptide capable of binding a nucleic acid binding polypeptide recognition sequence; and In yet another aspect the present disclosure provides, a use of exosomes to treat an animal in need thereof wherein the exosomes comprise:
(I) a chimeric polypeptide comprising as operably linked components:
(i) an exosomal membrane polypeptide;
(ii) a neural cell targeting polypeptide; and
(iii) a nucleic acid binding polypeptide capable of binding a nucleic acid binding polypeptide recognition sequence; and
(II) a chimeric nucleic acid sequence comprising as operably linked components:
(i) a nucleic acid binding polypeptide recognition sequence; and
(ii) a nucleic acid sequence encoding a polypeptide of interest.

Other features and advantages of the present disclosure will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described in relation to its figures. The figures provided herein are provided for illustration purposes and are not intended to limit the present disclosure.

Figure 1:
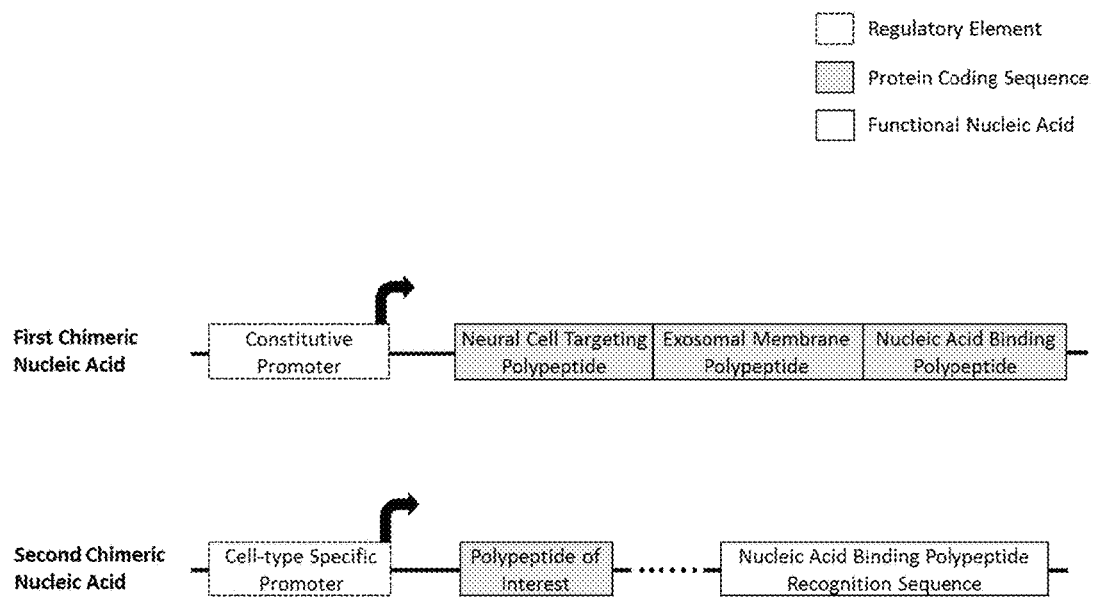
FIG. 1 depicts an overview of the first and second chimeric nucleic acid sequences. The first chimeric nucleic acid sequence comprises as operably linked components: (i) a nucleic acid sequence encoding an exosomal membrane polypeptide; (ii) a nucleic acid sequence encoding a neural cell targeting polypeptide; and (iii) a nucleic acid sequence encoding a nucleic acid binding polypeptide capable of binding a nucleic acid binding polypeptide recognition sequence. The second chimeric nucleic acid sequence comprises as operably linked components: (i) a nucleic acid binding polypeptide recognition sequence; and (ii) a nucleic acid sequence encoding a polypeptide of interest regulated by a promoter element specific to the target cell of interest.

The figures together with the following detailed description make apparent to those skilled in the art how the disclosure may be implemented in practice.

DETAILED DESCRIPTION OF THE DISCLOSURE

Various compositions and methods will be described below to provide an example of an embodiment of each claimed subject matter. No embodiment described below limits any claimed subject matter and any claimed subject matter may cover methods, processes, compositions or systems that differ from those described below. The claimed subject matter is not limited to compositions or methods having all of the features of any one composition, method, system or process described below or to features common to multiple or all of the compositions, systems or methods described below. It is possible that a composition, system, method or process described below is not an embodiment of any claimed subject matter. Any subject matter disclosed in a composition, system, method or process described below that is not claimed in this document may be the subject matter of another protective instrument, for example, a continuing patent application, and the applicants, inventors or owners do not intend to abandon, disclaim or dedicate to the public any such subject matter by its disclosure in this document.

All publications, patents, and patent applications are herein incorporated by reference in their entirety to the same extent as if each individual publication, patent or patent application was specifically and individually indicated to be incorporated by reference in its entirety.

Definitions

The term "glial cell", as used herein, refers to connective tissue cells of the central nervous system providing structural and functional support to the neuronal cells of the central nervous system, including, for example, in the form of providing nutrition and homeostasis and/or by participation in signal transmission in the nervous system. Glial cells include, but are not limited to, astrocytes (also referred to herein as astroglial cells), microglia, and oligodendrocytes.

The term "microglial cell" or "microglia", as used herein, refers to a class of glial cells involved in the mediation of an immune response within the central nervous system by acting as macrophages. Microglial cells are capable of producing exosomes, and further include different forms of microglial cells, including amoeboid microglial cells, ramified microglial cells and reactive microglial cells. Microglial cells include reactive microglia, which are defined as quiescent ramified microglia that transform into a reactive, macrophage-like state and accumulate at sites of brain injury and inflammation to assist in tissue repair and neural regeneration (Kreutzberg, 1996).

The term "astroglial cell" or "astrocyte", as used herein, refers to a class of glial cells involved in the structural and nutritional support of central nervous system cell populations and in the repair and scarring process following neural injury. Astroglial cells further include different forms including reactive astroglial cells, fibrous astroglial cells, protoplasmic astroglial cells, and radial astroglial cells. The term astroglial cell includes reactive astrocytes which, in response to brain injury, proliferate and become the primary cellular component of the resulting glial scar (Stitchel & Miller, 1988). Reactive astrocytes undergo morphological changes, increase synthesis of glial fibrillary acidic protein (GFAP), and secrete molecules to modulate neuronal outgrowth thereby restricting neuronal regeneration and functional recovery following a TBI or stroke.

The term "exosome" as used herein refers to nanometer sized (having a diameter in the range of approximately 30 nm-150 nm) membrane-derived vesicles, secreted by a mammalian cell, including, for example, a microglial cell.

The term "exosomal membrane polypeptide", as used herein refers to any protein associated with or integrated within exosomal membranes. The term exosomal membrane polypeptide includes, without limitation, LAMP-1 polypeptide, LAMP-2A polypeptide, LAMP-2B polypeptide, LAMP-2C polypeptide, LIMP-2/SCARB2 polypeptide, Flotillin-1 polypeptide, and any other protein capable of association with or integration within exosomal membranes.

The term "neural cell targeting polypeptide", as used herein in refers to any polypeptide capable of associating with or binding to neural cells. The term neural cell targeting polypeptide includes, without limitation, the entirety, or any functional portion of viral envelope proteins known to associate with or bind to neural cells, including rabies virus glycoprotein (RVG). The term neural cell targeting polypeptide further also includes cell-surface expression of antibodies including, but not limited to, anti-GLAST IgG, which confers in vivo and in vitro selective targeting to astrocytes (Fassler et al., 2013; Balyasnikova et al., 2010). Neural cell targeting polypeptide further also includes a T7/transferrin receptor-binding polypeptide operably linked to a cell membrane permeant peptide (such as penetratin or transportan) as described by Youn, Chen and Furgeson (2014) or Muratovska and Eccles (2004).

The term "nucleic acid binding polypeptide" or "nucleic acid binding domain", as may be used interchangeably herein, refers to a polypeptide capable of specifically binding to a specific nucleic acid recognition sequence. The term nucleic acid binding polypeptide includes, without limitation, any polypeptide comprising a helix-turn-helix, zinc finger, leucine zipper, winged helix, winged helix-turn-helix, helix-loop-helix, HMG-box, Wor3, immunoglobulin fold, 83, TAL effector, or RNA-guided DNA-binding domain. Further included are the Gal4 polypeptide and any TAL effector, including a synthetically engineered TAL effector (Sanjana et al., 2013).

The term "nucleic acid binding polypeptide recognition sequence" as used herein, refers to a nucleic acid sequence capable of specifically associating with a polypeptide capable of binding to the sequence. The nucleic acid sequence may vary in length and may for example be a DNA sequence of at least 10 base pairs, at least 20 base pairs, or at least 50 base pairs in length. The term nucleic acid binding polypeptide recognition sequence includes, for example, the Gal4 Upstream Activator Sequence (specific to the Gal4 polypeptide) or any TAL effector recognition sequence, including any synthetically engineered TAL effector recognition sequence (specific to its corresponding TAL effector polypeptide; Sanjana et al., 2013).

The term "nucleic acid sequence", as used herein, refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil, and xanthine and hypoxanthine.

"Operably linked" refers to a configuration of nucleic acids in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Furthermore, the polynucleotide sequences contemplated herein may be present in expression vectors.

The term "vector" or "expression vector" refers to a means by which nucleic acid (e.g., DNA) can be introduced into a host organism or host tissue. There are various types of vectors including plasmid vector, bacteriophage vectors, cosmid vectors, bacterial vectors, and viral vectors. The term vector, as used herein, may refer to a recombinant nucleic acid that has been engineered to express a heterologous polypeptide (e.g., the fusion proteins disclosed herein), or a heterologous promoter (e.g., a eukaryotic or prokaryotic promoter) operably linked to a polynucleotide that encodes a protein.

A "heterologous promoter" refers to a promoter that is not the native or endogenous promoter for the protein that is being expressed. For example, as contemplated herein, heterologous promoters for NeuroD1 include a synthetic gfaABC$_1$D promoter, a eukaryotic GFAP promoter, or a prokaryotic CMV promoter, none of which are the native, endogenous promoter for NeuroD1. The vectors contemplated herein may be introduced and propagated in a prokaryote, such as *Escherichia coli*, which may be used to amplify copies of a vector to be introduced into a eukaryotic cell or as an intermediate vector in the production of a vector to be introduced into a eukaryotic cell (e.g. amplifying a plasmid as part of a viral vector packaging system).

The term "expression", as used herein, refers to the process by which a polynucleotide is transcribed from a DNA template (such as into and mRNA or other RNA transcript) and/or the process by which a transcribed mRNA is subsequently translated into peptides, polypeptides, or proteins. If the polynucleotide is derived from genomic DNA, expression may include splicing of the mRNA in a eukaryotic cell.

The terms "peptide", "protein", or "polypeptide", as used herein, typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids. The polypeptides contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myrtstoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine threonine or histidine). The amino acid sequences of polypeptide variants, mutants, or derivatives as contemplated herein may also include conservative amino acid substitutions relative to a reference amino acid sequence. For example, a variant, mutant, or derivative protein may include conservative amino acid substitutions relative to a reference molecule. Conservative amino acid substitutions are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation. (b) the charge or hydrophobicity of the molecule at the site of the substitution, and/or (c) the bulk of the side chain. The following table provides a list of exemplary conservative amino acid substitutions which are contemplated herein:

| Original residue | Conservative substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Gln, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

By the term "substantially identical" it is meant that two polypeptide sequences preferably are at least 70% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch, 1970, as revised by Smith and Waterman, 1981, so that the highest order match is obtained between the two sequences and the number of identical amino acids is determined between the two sequences. Methods to calculate the percentage identity between two amino acid sequences are generally art recognized and include, for example, those described by Carillo and Lipman, 1988 and those described in: Lesk, 1988. Generally, computer programs will be employed for such calculations. Computer programs that may be used in this regard include, but are not limited to, GCG (Devereux et al. 1984) BLASTP, BLASTN and FASTA (Altschul et al. 1990). A particularly preferred method for determining the percentage identity between two polypeptides involves the Clustal W algorithm (Thompson, J D, Higgines, D G and Gibson T J, 1994) together with the BLOSUM 62 scoring matrix (Henikoff S & Henikoff, J G, 1992) using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature ($Tm=81.5°$ C.$-16.6$ (Log 10 [Na+])$+0.41$(% (G+C)$-600/l$), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Ausubel, 1989 and in: Sambrook et al., 1989.

The term "chimeric", as used herein in the context of nucleic acid sequences or proteins, refers to at least two linked nucleic acid sequences or polypeptide sequences, which are not naturally linked. Chimeric nucleic acid sequences and chimeric polypeptide sequences include linked nucleic acid sequences or polypeptide sequences of different natural origins. For example, a nucleic acid sequence constituting an astrocyte specific promoter linked to a nucleic acid sequence encoding a NeuroD1 polypeptide is considered a chimeric nucleic acid sequence. For example, a polypeptide sequence constituting an exosomal membrane polypeptide linked to a neural targeting polypeptide is considered a chimeric protein. Chimeric nucleic acid sequences and protein sequences also may comprise nucleic acid sequences or polypeptide sequences of the same natural origin, provided they are not naturally linked. For example a nucleic acid sequence constituting a promoter obtained from a particular cell-type may be linked to a nucleic acid sequence encoding a polypeptide obtained from that same cell-type, but not normally linked to the nucleic acid sequence constituting the promoter. Chimeric nucleic acid sequences and protein sequences also include nucleic acid sequences comprising any naturally occurring nucleic acid sequence linked to any non-naturally occurring nucleic acid sequence or polypeptide sequence.

The terms "LAMP-2B protein", "LAMP-2B polypeptide" and "LAMP-2B", as may be used interchangeably herein, refer to any and all proteins comprising a sequence of amino acid residues which is (i) substantially identical to the amino acid sequences constituting any LAMP-2B polypeptide set forth herein, including, for example, SEQ. ID. NO: 33, or (ii) encoded by a nucleic acid sequence capable of hybridizing under at least moderately stringent conditions to any nucleic acid sequence encoding any LAMP-2B polypeptide set forth herein, but for the use of synonymous codons.

The terms "RVG protein", "RVG polypeptide" and "RVG", as may be used interchangeably herein, refer to any and all proteins comprising a sequence of amino acid residues which is (i) substantially identical to the amino acid sequences constituting any RVG polypeptide set forth herein, including, for example, SEQ. ID. NO: 45, or (ii) encoded by a nucleic acid sequence capable of hybridizing under at least moderately stringent conditions to any nucleic acid sequence encoding any RVG polypeptide set forth herein, but for the use of synonymous codons.

The terms "Gal4 protein", "Gal4 polypeptide" and "Gal4", as may be used interchangeably herein, refer to any and all proteins comprising a sequence of amino acid residues which is (i) substantially identical to the amino acid sequences constituting any Gal4 polypeptide set forth herein, including, for example, SEQ. ID. NO: 47, or (ii) encoded by a nucleic acid sequence capable of hybridizing under at least moderately stringent conditions to any nucleic acid sequence encoding any Gal4 polypeptide set forth herein, but for the use of synonymous codons.

The terms "TAL effector protein", "TAL effector polypeptide" and "TAL effector", as may be used interchangeably herein, refer to any and all proteins comprising a sequence of amino acid residues which is (i) substantially identical to the amino acid sequences constituting any TAL effector polypeptide set forth herein, including, for example, SEQ. ID. NO: 48, or (ii) encoded by a nucleic acid sequence capable of hybridizing under at least moderately stringent conditions to any nucleic acid sequence encoding any TAL effector polypeptide set forth herein, but for the use of synonymous codons.

The terms "NeuroD1 protein", "NeuroD1 polypeptide" and "NeuroD1", as may be used interchangeably herein, refer to any and all proteins comprising a sequence of amino acid residues which is (i) substantially identical to the amino acid sequences constituting any NeuroD1 polypeptide set forth herein, including, for example, SEQ. ID. NO: 49, or (ii) encoded by a nucleic acid sequence capable of hybridizing under at least moderately stringent conditions to any nucleic acid sequence encoding any NeuroD1 polypeptide set forth herein, but for the use of synonymous codons.

The terms "LAMP-2B nucleic acid sequence", "nucleic acid sequence encoding LAMP-2B protein", "nucleic acid sequence encoding LAMP-2B polypeptide" and "nucleic acid sequence encoding LAMP-2B", as may be used interchangeably herein, refer to any and all nucleic acid sequences encoding a LAMP-2B polypeptide, including, for example, SEQ. ID. NO: 1. Nucleic acid sequences encoding a LAMP-2B polypeptide further include any and all nucleic acid sequences which (i) encode polypeptides that are substantially identical to the LAMP-2B polypeptide sequences set forth herein; or (ii) hybridize to any LAMP-2B nucleic acid sequences set forth herein under at least moderately stringent hybridization conditions or which would hybridize thereto under at least moderately stringent conditions but for the use of synonymous codons.

The terms "RVG nucleic acid sequence", "nucleic acid sequence encoding RVG protein", "nucleic acid sequence encoding RVG polypeptide" and "nucleic acid sequence encoding RVG", as may be used interchangeably herein, refer to any and all nucleic acid sequences encoding a RVG polypeptide, including, for example, SEQ. ID. NO: 13. Nucleic acid sequences encoding a RVG polypeptide further include any and all nucleic acid sequences which (i) encode polypeptides that are substantially identical to the RVG polypeptide sequences set forth herein; or (ii) hybridize to any RVG nucleic acid sequences set forth herein under at least moderately stringent hybridization conditions or which would hybridize thereto under at least moderately stringent conditions but for the use of synonymous codons.

The terms "Gal4 nucleic acid sequence", "nucleic acid sequence encoding Gal4 protein", "nucleic acid sequence encoding Gal4 polypeptide" and "nucleic acid sequence encoding Gal4", as may be used interchangeably herein, refer to any and all nucleic acid sequences encoding a Gal4 polypeptide, including, for example, SEQ. ID. NO: 15. Nucleic acid sequences encoding a Gal4 polypeptide further include any and all nucleic acid sequences which (i) encode polypeptides that are substantially identical to the Gal4 polypeptide sequences set forth herein; or (ii) hybridize to any Gal4 nucleic acid sequences set forth herein under at least moderately stringent hybridization conditions or which would hybridize thereto under at least moderately stringent conditions but for the use of synonymous codons.

The terms "TAL effector nucleic acid sequence", "nucleic acid sequence encoding TAL effector protein", "nucleic acid sequence encoding TAL effector polypeptide" and "nucleic acid sequence encoding TAL effector", as may be used interchangeably herein, refer to any and all nucleic acid sequences encoding a TAL effector polypeptide, including, for example, SEQ. ID. NO: 16. Nucleic acid sequences encoding a TAL effector polypeptide further include any and all nucleic acid sequences which (i) encode polypeptides that are substantially identical to the TAL effector polypeptide sequences set forth herein; or (ii) hybridize to any TAL effector nucleic acid sequences set forth herein under at least moderately stringent hybridization conditions or which would hybridize thereto under at least moderately stringent conditions but for the use of synonymous codons.

The terms "NeuroD1 nucleic acid sequence", "nucleic acid sequence encoding NeuroD1 protein", "nucleic acid sequence encoding NeuroD1 polypeptide" and "nucleic acid sequence encoding NeuroD1", as may be used interchangeably herein, any and all nucleic acid sequences encoding a NeuroD1 polypeptide, including, for example, SEQ. ID. NO: 19. Nucleic acid sequences encoding a NeuroD1 polypeptide further include any and all nucleic acid sequences which (i) encode polypeptides that are substantially identical to the NeuroD1 polypeptide sequences set forth herein; or (ii) hybridize to any NeuroD1 nucleic acid sequences set forth herein under at least moderately stringent hybridization conditions or which would hybridize thereto under at least moderately stringent conditions but for the use of synonymous codons.

The terms "Gal4 Upstream Activator Sequence", "Gal4 UAS", and "Gal4 UAS nucleic acid sequence", as may be used interchangeably herein, refer to any and all nucleic acid sequences capable of binding Gal4 polypeptide, including, for example, SEQ. ID. NO: 17. Gal4 UAS further includes any and all nucleic acid sequences which hybridize to any Gal4 UAS nucleic acid sequences set forth herein under at least moderately stringent hybridization conditions, and capable of binding a Gal4 UAS polypeptide.

The terms "TAL effector recognition sequence", and "TAL effector nucleic acid recognition sequence", as may be used interchangeably herein, refer to any and all nucleic acid sequences capable of binding a TAL effector polypeptide, including, for example, SEQ. ID. NO: 18. TAL effector recognition sequence further includes any and all nucleic acid sequences which hybridize to any TAL effector nucleic acid recognition sequences set forth herein under at least moderately stringent hybridization conditions, and capable of binding a TAL effector polypeptide.

The terms "substantially pure" and "isolated", as may be used interchangeably herein describe a compound, cell, subcellular structure, chemical compound or pharmaceutical compound, for example, a glial cell, an exosome or a polypeptide, which has been separated from other components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis, or HPLC analysis.

The terms "reprogramming" and "reprogram", as used herein, refer to a process involving the re-differentiation or de-differentiation of a cell having the morphological and functional characteristics representative of a certain class of cells, into a cell having known morphological and functional characteristics of a different class of cells. Thus for example astroglial cells may be reprogrammed to neuronal cells.

The term "in vivo", as used herein to describe methods of producing exosomes, refers to methods involving the production of exosomes by a cell, including, for example, a microglial cell, while such cell is present within a living human or animal.

The term "in vitro" as used herein to describe methods of making exosomes refers to methods involving the production of exosomes by a cell, including for example a microglial cell, while such cell is not present within a living human or animal, including, without limitation, for example, in a microwell plate, a tube, a flask, a beaker, a tank, a reactor and the like, to form the exosomes.

The term "animal", as used herein, refers to any non-human animal belonging to the animal kingdom.

The term "transgenic" as used herein refers to an entity, e.g. a cell or an animal or human, having received nucleic acid material wherein such material is integrated into the genome of the entity, and wherein the material is received through other than naturally occurring processes or events, e.g. breeding, non-recombinant bacterial or viral infection, spontaneous mutation and the like.

It should be noted that terms of degree such as "substantially", "essentially" "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

All publications, patents and patent applications are herein incorporated by reference in their entirety to the same extent as if each individual publication.

General Implementation

As hereinbefore mentioned, the present disclosure relates to neural cells. Neural cells, including astrocytes, microglia and neurons, are located in the central and peripheral nervous system, and the heretofore known techniques for the selective delivery of therapeutics specific to neural cell types are suboptimal. The herein provided novel methods permit the specific delivery of protein or nucleic acid therapeutics to neural cells, by introducing in vivo nucleic acid sequences encoding a polypeptide of interest into microglial cells. The methods of the present disclosure are useful inter alia in the reprogramming of astroglial cells to replace damaged neuronal cells, such as those lost due to traumatic brain injury or ischemic stroke.

Accordingly, the present disclosure provides, in at least one aspect, in at least one embodiment, a method of expressing a polypeptide of interest in an astroglial cell, the method comprising
  a) introducing a first and second chimeric nucleic acid sequence in a microglial host cell, the first chimeric nucleic acid sequence comprising as operably linked components:
    (i) a nucleic acid sequence encoding an exosomal membrane polypeptide;
    (ii) a nucleic acid sequence encoding a neural cell targeting polypeptide; and
    (iii) a nucleic acid sequence encoding a nucleic acid binding polypeptide capable of binding a nucleic acid binding polypeptide recognition sequence; and
  the second chimeric nucleic acid sequence comprising as operably linked components:
    (i) a nucleic acid binding polypeptide recognition sequence; and
    (ii) a nucleic acid sequence encoding a polypeptide of interest;
  (b) growing the microglial host cell to produce exosomes;
  (c) delivering the exosomes to an astroglial cell; and
  (d) expressing the polypeptide of interest in the astroglial cell.

The present disclosure provides, in at least one aspect, methods for the expression of polypeptides in a glial cell, the methods involving introducing a first and second chimeric nucleic acid sequence into a microglial cell. In accordance herewith the first and second chimeric nucleic acid sequence are separate, unlinked nucleic acid sequences. In accordance with some embodiments, the first and second chimeric nucleic acid sequences are introduced into microglial cells by means of a first and second expression vector. The first and second chimeric nucleic acid sequence may be introduced into the microglial cell together or separately.

In accordance with the present disclosure, the first chimeric nucleic acid sequence comprises as operably linked components:
  (i) a nucleic acid sequence encoding an exosomal membrane polypeptide;
  (ii) a nucleic acid sequence encoding a neural cell targeting polypeptide; and
  (iii) a nucleic acid sequence encoding a nucleic acid binding polypeptide capable of binding a nucleic acid binding polypeptide recognition sequence; and
    the second chimeric nucleic acid sequence comprising as operably linked components:
  (i) a nucleic acid binding polypeptide recognition sequence; and
  (ii) a nucleic acid sequence encoding a polypeptide of interest;

Referring now to FIG. 1, shown therein is a schematic overview of an embodiment of the present disclosure, namely an embodiment comprising a first and second chimeric nucleic acid sequence. Shown at the top panel is the a first chimeric nucleic acid sequence comprising as operably linked components:

(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence.

Shown at the bottom panel is a second chimeric nucleic acid sequence comprising as operably linked components:
(i) a nucleic acid binding polypeptide recognition sequence; and
(ii) a nucleic acid sequence encoding a polypeptide of interest.

Further shown are regulatory elements included in an expression vector ensuring expression of the first and second chimeric sequence.

In accordance herewith, the nucleic acid sequence encoding an exosomal membrane polypeptide may be any nucleic acid sequence encoding an exosomal membrane polypeptide, including any polypeptide capable of integrating into, or associating with, an exosomal membrane.

In some embodiments, the nucleic acid sequence encoding an exosomal membrane polypeptide is a nucleic acid sequence encoding a LAMP-2B polypeptide. In some embodiments, the nucleic acid sequence encoding an exosomal membrane polypeptide is the nucleic acid sequence set forth in SEQ. ID NO: 1 or SEQ. ID NO: 2. In some embodiments, the exosomal membrane polypeptide is the polypeptide set forth in SEQ. ID NO: 33 or SEQ. ID NO: 34.

In some embodiments, the nucleic acid sequence encoding an exosomal membrane polypeptide is a nucleic acid sequence encoding the LAMP-2A polypeptide. In some embodiments, the nucleic acid sequence encoding an exosomal membrane polypeptide is the nucleic acid sequence set forth in SEQ. ID NO: 3 or SEQ. ID NO: 4. In some embodiments, the exosomal membrane polypeptide is the polypeptide set forth in SEQ. ID NO: 35 or SEQ. ID NO: 36.

In some embodiments, the nucleic acid sequence encoding an exosomal membrane polypeptide is a nucleic acid sequence encoding the LAMP-2C polypeptide. In some embodiments, the nucleic acid sequence encoding an exosomal membrane polypeptide is the nucleic acid sequence set forth in SEQ. ID NO: 5 or SEQ. ID NO: 6. In some embodiments, the exosomal membrane polypeptide is the polypeptide set forth in SEQ. ID NO: 37 or SEQ. ID NO: 38.

In some embodiments, the nucleic acid sequence encoding an exosomal membrane polypeptide is a nucleic acid sequence encoding the LAMP-1 polypeptide. In some embodiments, the nucleic acid sequence encoding an exosomal membrane polypeptide is the nucleic acid sequence set forth in SEQ. ID NO: 7 or SEQ. ID NO: 8. In some embodiments, the exosomal membrane polypeptide is the polypeptide set forth in SEQ. ID NO: 39 or SEQ. ID NO: 40.

In some embodiments, the nucleic acid sequence encoding an exosomal membrane polypeptide is a nucleic acid sequence encoding the Limp-2/SCARB2 polypeptide. In some embodiments, the nucleic acid sequence encoding an exosomal membrane polypeptide is the nucleic acid sequence set forth in SEQ. ID NO: 9 or SEQ. ID NO: 10. In some embodiments, the exosomal membrane polypeptide is the polypeptide set forth in SEQ. ID NO: 41 or SEQ. ID NO: 42.

In some embodiments, the nucleic acid sequence encoding an exosomal membrane polypeptide is a nucleic acid sequence encoding the Flotillin-1 polypeptide. In some embodiments, the nucleic acid sequence encoding an exosomal membrane polypeptide is the nucleic acid sequence set forth in SEQ. ID NO: 11 or SEQ. ID NO: 12. In some embodiments, the exosomal membrane polypeptide is the polypeptide set forth in SEQ. ID NO: 43 or SEQ. ID NO: 44.

In other embodiments, the nucleic acid sequence encoding an exosomal membrane polypeptide may be a nucleic acid sequence encoding a suitable substitute for the LAMP-2B polypeptide, LAMP-2A polypeptide, LAMP-2C polypeptide, LAMP-1polypeptide, Limp-2/SCARB2 polypeptide or Flotillin-1 polypeptide.

In accordance herewith the nucleic acid sequence encoding a neural cell targeting polypeptide may be any nucleic acid sequence encoding a neural cell targeting polypeptide, including any polypeptide capable of being directed to or targeted to a neural cell. The neural cell targeting polypeptide may be targeted to any neural cell.

In some embodiments, the nucleic acid sequence encoding a neural cell targeting polypeptide is a nucleic acid sequence encoding a Rabies Virus Glycoprotein (RVG). In some embodiments, the nucleic acid sequence encoding a neural cell targeting polypeptide is the nucleic acid sequence set forth in SEQ. ID NO: 13. In some embodiments, the neural cell targeting polypeptide is the polypeptide set forth in SEQ. ID NO: 45.

In some embodiments, the nucleic acid sequence encoding a neural cell targeting polypeptide is a nucleic acid sequence encoding a T7/transferrin receptor binding and cell permeating polypeptide. In some embodiments, the nucleic acid sequence encoding a neural cell targeting polypeptide is the nucleic acid sequence set forth in SEQ. ID NO: 14. In some embodiments, the neural cell targeting polypeptide is the polypeptide set forth in SEQ. ID NO: 46.

In other embodiments, the nucleic acid sequence encoding a neural cell targeting polypeptide may be a nucleic acid sequence encoding a suitable substitute for the RVG polypeptide or the T7/transferrin receptor binding and cell permeating polypeptide.

In accordance herewith the nucleic acid sequence encoding a nucleic acid binding polypeptide may be any nucleic acid sequence encoding a polypeptide capable of binding a specific nucleic acid binding polypeptide recognition sequence.

In some embodiments, the nucleic acid sequence encoding a nucleic acid binding polypeptide is a nucleic acid sequence encoding a Gal4 polypeptide. In some embodiments, the nucleic acid sequence encoding a nucleic acid binding polypeptide is the nucleic acid sequence set forth in SEQ. ID NO: 15. In some embodiments, the nucleic acid binding polypeptide is the polypeptide set forth in SEQ. ID NO: 47.

In some embodiments, the nucleic acid sequence encoding a nucleic acid binding polypeptide is a nucleic acid sequence encoding a synthetic TAL effector polypeptide. In some embodiments, the nucleic acid sequence encoding a nucleic acid binding polypeptide is the nucleic acid sequence set forth in SEQ. ID NO: 16. In some embodiments, the nucleic acid binding polypeptide is the polypeptide set forth in SEQ. ID NO: 48.

In other embodiments, the nucleic acid sequence encoding a nucleic acid binding polypeptide may be a nucleic acid sequence encoding a suitable substitute for the Gal4 polypeptide or a nucleic acid sequence encoding a synthetic TAL effector polypeptide.

In accordance herewith, the nucleic acid sequence comprising a nucleic acid binding polypeptide recognition sequence may be any nucleic acid sequence comprising a nucleic acid binding polypeptide recognition sequence.

In some embodiments, the nucleic acid sequence comprising a nucleic acid binding polypeptide recognition sequence is a nucleic acid sequence comprising the Gal4 Upstream Activator Sequence. In some embodiments, the nucleic acid sequence comprising a nucleic acid binding polypeptide recognition sequence is the nucleic acid sequence set forth in SEQ. ID NO: 17.

In some embodiments, the nucleic acid sequence comprising a nucleic acid binding polypeptide recognition sequence is a nucleic acid sequence comprising the synthetic TAL effector polypeptide recognition sequence. In some embodiments, the nucleic acid sequence comprising a nucleic acid binding polypeptide recognition sequence is the nucleic acid sequence set forth in SEQ. ID NO: 18.

In other embodiments, the nucleic acid sequence encoding a nucleic acid binding polypeptide recognition sequence may be a nucleic acid sequence encoding a suitable substitute for the Gal4 Upstream Activator Sequence, or the TAL effector polypeptide recognition sequence.

In accordance herewith the nucleic acid sequence encoding a polypeptide of interest may be any nucleic acid sequence encoding a polypeptide of interest. In some embodiments the polypeptide of interest is a polypeptide capable of reprogramming an astroglial cell.

In some embodiments, the nucleic acid sequence encoding a polypeptide of interest is a nucleic acid sequence encoding a NeuroD1 polypeptide. In some embodiments, the nucleic acid sequence encoding a polypeptide of interest is the nucleic acid sequence set forth in SEQ. ID NO: 19 or SEQ. ID NO: 20. In some embodiments, the polypeptide of interest is the polypeptide set forth in SEQ. ID NO: 49 or SEQ. ID NO: 50.

In some embodiments, the nucleic acid sequence encoding a polypeptide of interest is a nucleic acid sequence encoding a Sox2 polypeptide. In some embodiments, the nucleic acid sequence encoding a polypeptide of interest is the nucleic acid sequence set forth in SEQ. ID NO: 21 or SEQ. ID NO: 22. In some embodiments, the polypeptide of interest is the polypeptide set forth in SEQ. ID NO: 51 or SEQ. ID NO: 52.

In other embodiments, the nucleic acid sequence encoding a polypeptide of interest may be a nucleic acid sequence encoding a suitable substitute for NeuroD1 polypeptide, or Sox2 polypeptide.

In other embodiments, the nucleic acid sequence encoding a polypeptide of interest is a nucleic acid sequence encoding a fluorescent polypeptide. Such polypeptide may be used for research purposes. In some embodiments, the nucleic acid sequence of interest is a nucleic acid sequence encoding a green fluorescent polypeptide or a variant thereof. In some embodiments, the nucleic acid sequence encoding a polypeptide of interest is a nucleic acid sequence encoding enhanced green fluorescent protein (eGFP). In some embodiments, the nucleic acid sequence encoding a polypeptide of interest is the nucleic acid sequence set forth in SEQ. ID NO: 23. In some embodiments, the polypeptide of interest is the polypeptide set forth in SEQ. ID NO: 53.

The first chimeric nucleic acid sequence may, in accordance with some embodiments hereof, further additionally comprise one or more of the following nucleic acid sequences:
(iv) a nucleic acid sequence encoding a cleavable polypeptide; and
(v) a nucleic acid sequence encoding a polypeptide providing a signal for nuclear localization in the target cell.

In accordance herewith the nucleic acid sequence encoding a cleavable polypeptide linker may be any nucleic acid sequence encoding a cleavable polypeptide linker.

In some embodiments, the nucleic acid sequence encoding a cleavable polypeptide linker is capable of undergoing autocatalytic cleavage. In some embodiments, the autocatalytic polypeptide linker is an intein that is cleaved in reducing environments including, but not limited to, the Ssp DnaE, Npu DnaE, or Prp8 inteins. In some embodiments, these inteins have been modified to include a disulfide bond between the N-terminal extein and the intein. In some embodiments, the nucleic acid sequence encoding an autocatalytic intein-based polypeptide linker is the nucleic acid sequence set forth in SEQ. ID NO: 24 or SEQ. ID NO: 25 or SEQ. ID NO: 26. In some embodiments, the autocatalytic intein-based polypeptide linker is the polypeptide set forth in SEQ. ID NO: 54 or SEQ. ID NO: 55 or SEQ. ID NO: 56.

In other embodiments, the nucleic acid sequence encoding a cleavable polypeptide linker is protease-cleavable. In some embodiments, this protease-cleavable linker is cleavable specifically by Furin. In some embodiments, the nucleic acid sequence encoding a protease-cleavable linker is the nucleic acid sequence set forth in SEQ. ID NO: 27. In some embodiments, the protease-cleavable linker is the polypeptide set forth in SEQ. ID NO: 57.

In accordance herewith, the nucleic acid sequence encoding a polypeptide providing a signal for nuclear localization in the target cell may be any nucleic acid sequence encoding a polypeptide providing a signal for nuclear localization in the target cell.

In some embodiments, the nucleic acid sequence encoding a polypeptide providing a signal for nuclear localization in the target cell is the nucleic acid sequence encoding the simian virus 40 (SV40) nuclear localization signal. In some embodiments, the nucleic acid sequence encoding a polypeptide providing a signal for nuclear localization in the target cell is the nucleic acid sequence set forth in SEQ. ID NO: 28. In some embodiments, the polypeptide providing a signal for nuclear localization in the target cell is the polypeptide set forth in SEQ. ID NO: 58.

The second chimeric nucleic acid sequence may, in accordance with some embodiments hereof, further additionally comprise one or more of the following nucleic acid sequences:
(iii) a nucleic acid sequence encoding a regulatory element, such as a promoter, capable of expressing a polypeptide of interest in a astroglial cell; and
(iv) a nucleic acid sequence providing a selectable or screenable marker.

In some embodiments, the nucleic acid sequence encoding a regulatory element capable of expressing a polypeptide of interest in an astroglial cell is an astrocyte-specific promoter, such as a glial fibrillary acidic protein (GFAP) promoter or a derivative thereof. In some embodiments, the nucleic acid sequence encoding a regulatory element capable of expressing a polypeptide of interest in an astroglial cell is the nucleic acid sequence set forth in SEQ. ID NO: 29 or SEQ. ID NO: 30. In some embodiments, the nucleic acid sequence encoding a regulatory element capable of expressing a polypeptide of interest in an astroglial cell is the synthetic nucleic acid sequence set forth in SEQ. ID NO: 31.

In accordance herewith the nucleic acid sequence providing a selectable or screenable marker may be any nucleic acid sequence providing a selectable or screenable marker, permitting screening and selection of prokaryotic or eukaryotic cells comprising the marker. This marker enables for the selection of prokaryotic cells which contain DNA vectors useful in the generation of the above described chimeric nucleotide sequences. In some embodiments, the nucleic acid providing a selectable or screenable marker encodes a polypeptide. In other embodiments, the selectable or screenable marker provides for a polynucleotide, for example an RNA polynucleotide.

In some embodiments, the nucleic acid sequence providing a selectable or screenable marker encodes an antibiotic resistance marker. In some embodiments, the nucleic acid sequence providing a selectable or screenable marker encodes an RNA polynucleotide capable of preventing expression of an otherwise lethal polypeptide. Such RNA polynucleotides may prevent the expression of lethal polypeptides via hybridization with the ribosome binding site of the lethal peptide coding sequence. One example of such RNA polynucleotides is the RNA-OUT polynucleotide from the *Escherichia coli* insertion sequence IS10 and engineered variants thereof (Mutalik et al., 2012). Such a lethal polypeptide may be encoded by a nucleic acid sequence separately introduced into host prokaryotic cells, and its expression may be controlled by an inducible promoter. In some embodiments, the nucleic acid sequence encoding a lethal polypeptide encodes the cytotoxic protein known as "control of cell death B" or CcdB. RNA polynucleotides capable of preventing expression of an otherwise lethal polypeptide, in accordance herewith are deemed preferred as a selectable marker, since they avoid the use of antibiotic resistance markers and are typically smaller in size. The latter is deemed beneficial in view of the limited size and space available for exosomes to accept nucleic acid sequences.

In some embodiments, the lethal polypeptide is encoded by the nucleic acid sequence set forth in SEQ. ID NO: 32.

As hereinbefore mentioned, the first and second chimeric nucleic acid sequence may be introduced into microglial cells by means of an expression vector. Accordingly, the present disclosure further comprises:

a first recombinant expression vector comprising as operably linked components:
  (a) one or more nucleic acid sequences capable of controlling expression in a host glial cell; and
  (b) (i) a nucleic acid sequence encoding an exosomal membrane polypeptide;
    (ii) a nucleic acid sequence encoding a neural cell targeting polypeptide; and
    (iii) a nucleic acid sequence encoding a nucleic acid binding polypeptide capable of binding a nucleic acid binding polypeptide recognition sequence,
  wherein the expression vector is suitable for expression in a host glial cell.

The present disclosure further comprises:

a second recombinant expression vector comprising as operably linked components:
  (a) one or more nucleic acid sequences capable of controlling expression in a host glial cell; and
  (b) (i) a nucleic acid binding polypeptide recognition sequence; and
    (ii) a nucleic acid sequence encoding a polypeptide of interest, wherein the expression vector is suitable for expression in a host glial cell.

The term "suitable for expression in a host glial cell" means that the recombinant expression vector comprises the first or second chimeric nucleic acid sequences of the present disclosure linked to genetic elements required to achieve expression in a host glial cell. Genetic elements that may be included in the expression vector in this regard include a transcriptional termination region, one or more nucleic acid sequences encoding marker genes, one or more origins of replication, enhancer sequences, and the like. The genetic elements are operably linked, typically, as will be known to those of skill in the art, by linking e.g. a promoter in the 5' to 3' direction of transcription to a coding sequence. In preferred embodiments, the expression vector further comprises genetic elements required for the integration of the vector or a portion thereof in the glial host cell's genome.

Pursuant to the present disclosure, the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include, but are not limited to, β-galactosidase, β-glucuronidase (GUS), red fluorescent protein (RFP), cyan fluorescent protein (CFP), and green fluorescent protein (GFP) including derivatives such as Clover and enhanced GFP (eGFP).

In accordance herewith, a first and second chimeric nucleic acid sequence are introduced in a microglial cell. The introduction of a first and second chimeric nucleic acid sequence in a microglial cell may be achieved by transforming or transfecting cultured microglial cells with expression vectors comprising the first and second chimeric nucleic acid sequences. In accordance herewith, a wide variety of suitable microglial cell lines may be selected and used, including, for example, any commercially available immortalized microglial cell lines (e.g., the mouse microglial cell lines EOC 13.31 (CRL-2468), EOC 2 (CRL-2467), or EOC 20 (CRL-2469) from the American Type Culture Collection (ATCC)). In some embodiments, microglial cells are isolated directly from samples of animal or human tissue obtained via biopsy, autopsy, donation, or other surgical or medical procedure. In some embodiments, microglial cells are derived from other cell types taken from samples of animal or human tissue obtained via biopsy, autopsy, donation, or other surgical or medical procedure. Suitable cell types for direct isolation or derivation of microglia include, but are not limited to, stem cells (e.g., mesenchymal stem cells), cortical cells, or bone marrow cells. Further suitable microglial cells include amoeboid microglial cells, ramified microglial cells and reactive microglial cells.

In some embodiments, microglial cells from a human or a specific animal species, e.g. microglial cells originating from mice, are used.

Microglial cells may be obtained using a variety of techniques and methodologies including, but not limited to, subculture from an immortalized cell line, density separation, derivation from other cell types, and cell culture selection. For example, mouse microglia may be obtained from mixed cortical cell populations using the "shake off" cell culture selection method described by Schildge et al. (2013). Further guidance describing the isolation of microglial cells may be found in Lee and Tansey (2013), and Moussaud and Draheim (2010), among others. In some embodiments, microglial cells from a specific individual, for example an individual selected to receive therapeutic treatment using microglial cells in accordance with the present disclosure, may be used, for example by deriving microglial cells from cultured patient bone marrow cells. Microglial cells may be derived from bone marrow cells through cell culture selection and media supplementation as described, for example, by Hinze and Stolzing (2012).

Microglial cells may be distinguished from other cell types based on adherence, morphology, silver carbonate staining, lectin staining, flow cytometry, membrane ion channel expression, protein profiling, and immunoreactivity, among other methods. For example, microglial identification may readily be accomplished using flow cytometry as it enables differences in antigen expression levels to be reliably quantified. Ramified parenchymal microglia have been demonstrated to possess the phenotype CD11b+, $CD45^{low}$, while reactive microglia and peripheral macrophages exhibit the phenotype $CD11b^+$, $CD45^{high}$ (Ford et al., 1995; Becher & Antel 1996). CD11b refers to "cluster of differentiation 11b" and belongs to the integrin alpha chain family that is used as a marker to distinguish macrophages. CD45 refers to "cluster of differentiation 45" and is a membrane tyrosine phosphatase that is used as a marker to distinguish cells of the hematopoietic lineage from the endothelial lineage. As another example, microglia may also be detected immunologically using antibodies raised against a number of macrophage-specific antigens (e.g. OX-42, CD68, and CD11b) although they may not readily distinguish microglia from other macrophages. Microglial cells may further be distinguished from other cell types by lack of immunoreactivity. For example, whereas astrocytes may be detected immunologically using antibodies raised against GFAP, microglial cells will demonstrate no immunoreactivity with this astrocyte-specific marker.

Microglial cells may be grown under controlled in vitro conditions allowing multiplication of the microglial cells. The exemplary conditions described herein below demonstrate at least one functional set of culture conditions useful for cultivation of microglial cells. It is to be understood, however, that the optimal plating and culture conditions can be determined by one of ordinary skill in the art using only routine experimentation. Cells can be plated onto the surface of culture vessels without attachment factors (e.g. in a microwell plate, a tube, a flask, a beaker, a tank, a reactor, and the like). Alternatively, the vessels can be precoated with natural, recombinant or synthetic attachment factors or peptide fragments (e.g., collagen or fibronectin, or natural or synthetic fragments thereof). The cell seeding densities for each experimental condition can be optimized for the specific culture conditions being used. When cell cultures reach at least 90% confluence, they may be subcultivated at an optimal ratio between 1:2 and 1:4 of confluent cells to fresh media. Microglial cells may be cultivated in a humidified cell incubator at about 37° C. and the incubator should contain about 3-10% carbon dioxide in air. Appropriate culture media are known in the art and may comprise, for example, a combination of any number of the following: an N2-medium (i.e. Dulbecco's Modified Eagle's Medium (DMEM) or DMEM: Nutrient Mixture F-12), L-glutamine, fetal bovine serum (FBS), sodium bicarbonate, glucose, sodium pyruvate, penicillin/streptomycin, dexamethasone, ascorbic acid, granulocyte-monocyte colony stimulating factor, astrocyte-conditioned media, and/or LADMAC-conditioned media. For example, a preferred media for differentiating a cell population comprising bone marrow cells into microglial cells is: 40% DMEM, 10% FBS, 50% astrocyte-conditioned media, and 20 ng/mL granulocyte-monocyte colony stimulating factor. As another example, a preferred media for culturing immortalized mouse microglia (ATCC EOC 13.31) is: 70% DMEM with 4 mM L-glutamine adjusted to contain 1.5 g/L sodium bicarbonate and 4.5 g/L glucose, 10% FBS, and 20% LADMAC-conditioned media. Culture medium pH should be in the range of about 7.0-7.6. Cells in closed or batch culture should undergo complete medium exchange (i.e., replacing spent media with fresh media) about every 2-3 days, or more or less frequently as required by the specific cell type. Further guidance describing growth and cultivation of microglial cells may be found, as examples, in Bronstein et al. (2013), Hinze and Stolzing (2012), and Witting and Moller (2011).

Transformation or transfection describes a process by which exogenous nucleic acids (for example, DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid:nucleic acid conjugates, naked DNA, artificial virions, and agent-enhanced uptake of DNA. Lipofection agents are sold commercially (e.g., Lipofectamine® 3000). Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time. Further guidance describing the transformation or transfection of microglial cells may be found, as examples, in Kim and Eberwine (2010), Felgner et al. (1987), and Kingston, Chen, and Rose (2003).

In the methods contemplated herein, a host cell may be transiently or non-transiently stably transfected with one or more vectors described herein. In some embodiments, a cell is transfected as it naturally occurs in a subject (i.e., in situ). In some embodiments, a cell that is transfected is taken from a subject (i.e., explanted). In some embodiments, the cell is derived from cells taken from a subject, such as a cell line. A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors) in order to establish a new cell line comprising cells containing the modification but lacking any other exogenous sequence.

In accordance herewith, microglial cells are grown to produce exosomes. In accordance with one embodiment, the microglial cells are grown to produce exosomes in vitro. In accordance with another embodiment the microglial cells are grown to produce exosomes in vivo. Thus the present disclosure further provides, in another aspect, microglia cells capable of producing exosomes, wherein the exosomes comprise:

(I) a chimeric polypeptide comprising as operably linked components:
  (i) an exosomal membrane polypeptide;
  (ii) a neural cell targeting polypeptide; and
  (iii) a nucleic acid binding polypeptide capable of binding a nucleic acid binding polypeptide recognition sequence; and (II) a chimeric nucleic acid sequence comprising as operably linked components:
(i) a nucleic acid binding polypeptide recognition sequence; and
(ii) a nucleic acid sequence encoding a polypeptide of interest.

In another aspect, the present disclosure provides microglia cells capable of producing exosomes, wherein the exosomes comprise:
(I) a chimeric polypeptide encoded by a first chimeric nucleic acid sequence; and
(II) a second chimeric nucleic acid sequence:
(a) the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
(b) the second chimeric nucleic acid sequence comprising as operably linked components:
(i) a nucleic acid binding polypeptide recognition sequence; and
(ii) a nucleic acid sequence encoding a polypeptide of interest.

In some embodiments, the exosomes are produced in microglia cells in vitro. In such embodiments, the exosomes may be separated from the microglia cells and an isolated exosome preparation may be obtained. Isolation of exosomes from microglial cells may be achieved using a variety of methodologies and techniques including, but not limited to, ultracentrifugation, precipitation, or affinity chromatography. Further guidance describing the isolation of exosomes may be found in El-Andaloussi et al. (2012).

Upon separation of the exosomes from the microglial cells, a substantially pure exosome preparation may be obtained. Accordingly, in another aspect the present disclosure further provides:
a preparation comprising substantially pure exosomes comprising:
(I) a chimeric polypeptide comprising as operably linked components:
(i) an exosomal membrane polypeptide;
(ii) a neural cell targeting polypeptide; and
(iii) a nucleic acid binding polypeptide capable of binding a nucleic acid binding polypeptide recognition sequence; and
(II) a chimeric nucleic acid sequence comprising as operably linked components:
(i) a nucleic acid binding polypeptide recognition sequence; and
(ii) a nucleic acid sequence encoding a polypeptide of interest.

In another aspect, the present disclosure provides a preparation comprising substantially pure exosomes comprising:
(I) a chimeric polypeptide encoded by a first chimeric nucleic acid sequence; and
(II) a second chimeric nucleic acid sequence,
(a) the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
(b) the second chimeric nucleic acid sequence comprising as operably linked components:
(i) a nucleic acid binding polypeptide recognition sequence; and
(ii) a nucleic acid sequence encoding a polypeptide of interest.

In accordance herewith, the exosomes comprise a chimeric polypeptide comprising an exosomal membrane polypeptide embedded in the exosomal membrane linked to a neural targeting polypeptide and a nucleic acid binding polypeptide capable of binding a specific nucleic acid binding polypeptide recognition sequence. In some embodiments, the neural targeting polypeptide is located N-terminally relative to the exosomal binding polypeptide. In some embodiments, the nucleic acid binding polypeptide capable of binding a specific nucleic acid binding polypeptide recognition sequence is located C-terminally from the exosomal membrane polypeptide.

In accordance herewith, the second chimeric nucleic acid sequence is located within the lumen of the exosome. The second chimeric nucleic acid sequence is connected to the polypeptide encoded by the first chimeric nucleic acid sequence via the nucleic acid binding polypeptide recognition sequence bound to the nucleic acid binding polypeptide capable of binding the recognition sequence.

Figure 2:
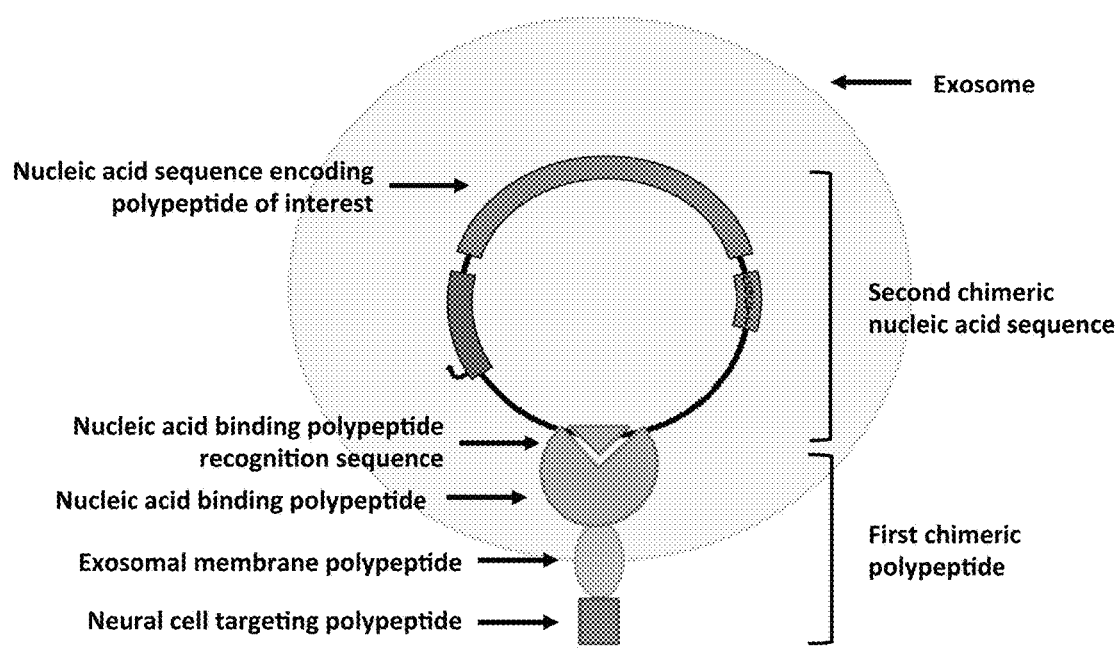
FIG. 2 depicts a schematic overview of an exosome produced by a microglial cell after introduction therein of a first and second chimeric nucleic acid sequence in accordance with the simplest embodiment of the present disclosure. Shown is a first chimeric polypeptide embedded in the exosomal membrane via an exosomal membrane polypeptide. A neural cell targeting polypeptide is located at the N-terminus of the exosomal membrane polypeptide, which is external to the exosome and allows for targeting of the exosome to neural cells. The C-terminus of the first chimeric polypeptide is a nucleic acid binding polypeptide that binds the second chimeric nucleic acid sequence via a specific nucleic acid binding polypeptide recognition sequence. The second chimeric nucleic acid sequence (in plasmid vector form) contains a regulatory element specific to the target cell operably linked to a nucleic acid sequence encoding a polypeptide of interest.

Referring now to FIG. 2, shown therein is a schematic representation of an embodiment of present disclosure, namely an exosome in an exosome preparation comprising a chimeric polypeptide and chimeric nucleic acid sequence,
the chimeric polypeptide comprising as operably linked components:
(i) an exosomal membrane polypeptide;
(ii) a neural cell targeting polypeptide; and
(iii) a nucleic acid binding polypeptide capable of binding a nucleic acid binding polypeptide recognition sequence; and
the chimeric nucleic acid sequence comprising as operably linked components:
(i) a nucleic acid binding polypeptide recognition sequence; and
(ii) a nucleic acid sequence encoding a polypeptide of interest.

In some embodiments of the present disclosure, the chimeric polypeptide additionally comprises:
(iv) a cleavable polypeptide; and
(v) a nucleic acid sequence encoding a polypeptide providing a signal for nuclear localization in the target cell.

Figure 3:
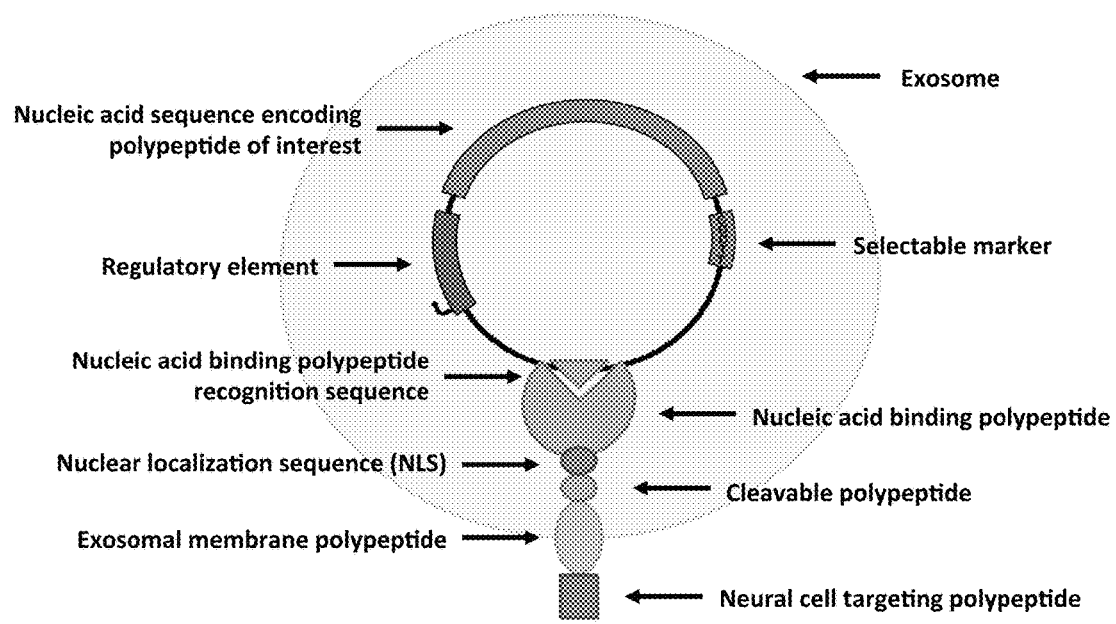
FIG. 3 depicts a schematic overview of an exosome produced by a microglial cell after introduction therein of a first and second chimeric nucleic acid sequence in accordance with another embodiment of the present disclosure. Shown is a first chimeric polypeptide embedded in the exosomal membrane via an exosomal membrane polypeptide. A neural cell targeting polypeptide is located at the N-terminus of the exosomal membrane polypeptide, which is external to the exosome and allows for targeting of the exosome to neural cells. The C-terminus of the first chimeric polypeptide is a nucleic acid binding polypeptide that binds the second chimeric nucleic acid sequence via a specific nucleic acid binding polypeptide recognition sequence. In this embodiment, the exosomal membrane polypeptide is linked to the nucleic acid binding polypeptide via a cleavable polypeptide linker and a nuclear localization polypeptide. When the first chimeric polypeptide is cleaved, the second chimeric nucleic acid sequence (bound to the nucleic acid binding polypeptide and nuclear localization polypeptide) is released for transport to the nucleus of the target neural cell (guided by the nuclear localization polypeptide). The second chimeric nucleic acid sequence (in plasmid vector form) contains a regulatory element specific to the target cell operably linked to a nucleic acid sequence encoding a polypeptide of interest. The plasmid also contains a selectable marker for preparation in bacteria.

A schematic representation of the foregoing embodiment of the present disclosure is further shown in FIG. 3.

In some embodiments of the present disclosure, the chimeric polypeptide comprises:
(i) exosomal membrane polypeptide wherein the exosomal polypeptide is a LAMP-2B polypeptide;
(ii) a neural cell targeting polypeptide wherein the neural targeting polypeptide is an RVG polypeptide;
(iii) a nucleic acid binding polypeptide capable of binding a nucleic acid binding polypeptide recognition sequence, wherein nucleic acid binding polypeptide capable of binding a nucleic acid binding polypeptide recognition sequence is a TAL-effector polypeptide;

(iv) a cleavable polypeptide; and
(v) a polypeptide providing a signal for nuclear localization in the target cell; and
and the chimeric nucleic acid sequence comprises:
(i) a nucleic acid binding polypeptide recognition sequence, wherein the nucleic acid binding polypeptide recognition sequence is a TAL-effector sequence; and
(ii) a nucleic acid sequence encoding a polypeptide of interest wherein the polypeptide of interest is NeuroD1.

Figure 4:
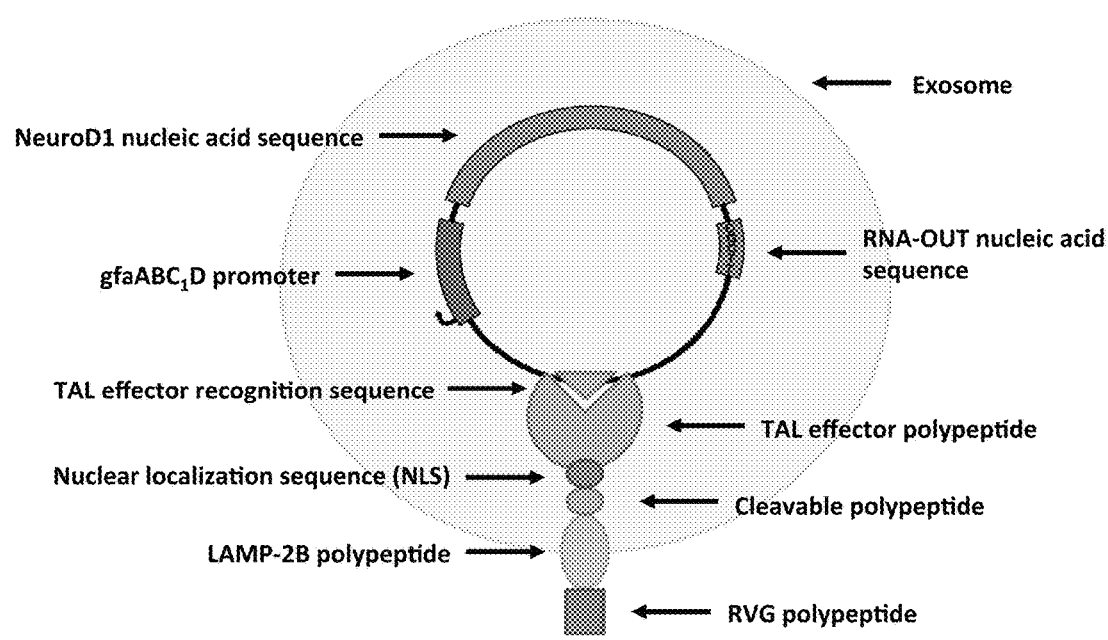
FIG. 4 depicts a schematic overview of an exosome produced by a microglial cell after introduction therein of a first and second chimeric nucleic acid sequence in accordance with another embodiment of the present disclosure. Shown is a first chimeric polypeptide embedded in the exosomal membrane via a LAMP-2B polypeptide transmembrane domain. An RVG is located near the N-terminus of LAMP-2B, which is external to the exosome and allows for targeting of the exosome to neural cells. The C-terminus of the first chimeric polypeptide is a synthetic transcription activator-like (TAL) effector nucleic acid binding polypeptide that binds the second chimeric nucleic acid sequence via the nucleic acid recognition sequence specific to the TAL effector. LAMP-2B is linked to the TAL effector polypeptide via a cleavable polypeptide and a nuclear localization polypeptide. When the first chimeric polypeptide is cleaved, the second chimeric nucleic acid sequence (bound to the TAL effector and nuclear localization polypeptide) is released for transport to the nucleus of the target neural cell (guided by the nuclear localization polypeptide). The second chimeric nucleic acid sequence contains an astrocyte-specific promoter operably linked to NeuroD1, a gene encoding a transcription factor necessary for neuronal differentiation. The plasmid also contains a small selectable nucleic acid sequence encoding an RNA polynucleotide for preparation in bacteria, namely an RNA-OUT sequence.

A schematic representation of the foregoing embodiment in accordance with the present disclosure is further shown in FIG. 4.

In one aspect, in some embodiments of the present disclosure, the exosomes are delivered to an astroglial cell. This can be achieved by contacting exosomes with an astroglial cell, for example, by preparing a formulation comprising microglial cells capable of producing exosomes, or by preparing a formulation comprising exosomes, and providing the formulation to an animal or human in need thereof in a manner that allows the exosomes or the microglial cells capable of producing the exosomes, to contact astroglial cells of the human or animal. While microglia innately migrate to sites of neural damage, target cell specificity for exosomes appears to be dictated solely by a combination of antigen and major histocompatibility complex (MHC) class I and II molecules, the expression of which is dependent on the parent cell (McKelvey et al., 2015). Thus, inclusion of a neural cell targeting polypeptide (such as RVG) and/or administration of exosomes derived from microglial cells may improve target cell specificity in some embodiments. Expression of the polypeptide of interest in the target astrocyte cells requires binding of the exosomes to the plasma membrane of the target cell and internalization of the chimeric nucleic acid vector, which is then shuttled to the nucleus of the target cell via the included nuclear localization sequence.

The exosomes may be formulated to prepare a pharmaceutical or veterinary composition comprising exosomes for delivery to an animal or human in need thereof in a manner that permits expression of the protein of interest in the astroglial cells of the animal or human.

In some embodiments, the exosomes are produced in microglia cells in vivo. In such embodiments, microglial cells are prepared for delivery to a human or an animal in need thereof. Delivery of the prepared microglial cells stimulates the production in vivo of exosomes by microglial cells, in vivo contacting of the produced exosomes with neural cells, and expression of the protein of interest in the astroglial cells of the human or animal.

Thus in another aspect, the present disclosure provides a transgenic animal comprising transgenic astroglial cells in which a protein of interest is expressed, wherein the transgenic astroglial cells have been obtained by:
introducing a first and second chimeric nucleic acid sequence in a microglial host cell, the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
the second chimeric nucleic acid sequence comprising as operably linked components:
(i) a nucleic acid binding polypeptide recognition sequence; and
(ii) a nucleic acid sequence encoding a polypeptide of interest;
(b) growing the microglial host cell to produce exosomes;
(c) delivering the exosomes to an astroglial cell; and
(d) expressing the polypeptide of interest in the astroglial cell.

In yet another aspect, the present disclosure provides a transgenic animal comprising transgenic astroglial cells wherein the transgenic astroglial cells comprise a chimeric nucleic acid sequence comprising:
(i) a nucleic acid binding polypeptide recognition sequence; and
(ii) a nucleic acid sequence encoding a polypeptide of interest.

In yet another aspect, the present disclosure provides a transgenic animal comprising transgenic astroglial cells in which a protein of interest is transgenically expressed in the astroglial cells. In some embodiments the protein of interest is NeuroD1.

In accordance herewith, the astroglial cells in which a protein of interest is expressed includes the astroglial cells of a human or an animal. The astroglial cells may be any astroglial cells of the central nervous system or peripheral nervous system. The astroglial cells in which the protein of interest is expressed include reactive astrocyte cells, fibrous astroglial cells, protoplasmic astroglial cells, and radial astroglial cells. The astroglial cells, as a result of the expression of the protein of interest, may reprogram. Thus, for example, certain astroglial cells, e.g. reactive astrocyte cells, may as a result of the expression of a protein of interest, such as NeuroD1, re-differentiate to form neurons. The astroglial cells further include astroglial cells that have formed scar tissue as a result of a brain injury. In further embodiments, the astroglial cells are astroglial cells that have formed scar tissue as a result of an ischemic stroke or traumatic brain injury.

In embodiments hereof wherein exosomes are delivered as a pharmaceutical or veterinary compositions to a human or an animal in need thereof, and in embodiments hereof wherein microglial cells are delivered as a pharmaceutical or veterinary composition to an animal or human in need thereof, the animal or human will receive a nucleic acid sequence encoding a protein of interest which is incorporated into astroglial cells of the human or animal, and expressed therein. Accordingly, the genetic constitution of the astroglial cell is modulated in such a manner that at least one protein that is not naturally produced by the astroglial cell, or not normally produced at certain levels by the cell, is produced by the astroglial cell, or produced at altered levels by the cell.

Veterinary compositions include compositions for the treatment of any animal including, without limitation, compositions for the treatment of a cow, horse, pig, chicken, or fish and further including, without limitation, compositions for the treatment of companion animals such as a dog or a cat.

As hereinbefore described, the exosomes and the microglial cells of the present disclosure obtained in accordance with the present disclosure may be used to prepare a pharmaceutical composition for use as a pharmaceutical drug, therapeutic agent or medicinal agent, or as a veterinary composition for use as a veterinary drug, therapeutic or medicinal agent. Thus the present disclosure further includes pharmaceutical and veterinary compositions comprising the exosomes or the microglial cells prepared in accordance with the methods of the present disclosure for delivery to an astroglial cell. Pharmaceutical or veterinary drug preparations comprising the exosomes and microglial cells in accordance with the present disclosure in some embodiments further comprise vehicles, excipients, diluents, and auxiliary substances, such as wetting or emulsifying agents, pH buffering substances and the like. These vehicles, excipients and auxiliary substances are generally pharmaceutically or veterinary acceptable agents that may be administered without undue toxicity. Pharmaceutically and veterinary acceptable excipients include, but are not limited to, liquids such as water, saline, polyethylene glycol, hyaluronic acid, glycerol and ethanol. Pharmaceutically and veterinary acceptable salts can also be included therein, for example, mineral acid salts such as hydrochlorides, phosphates, sulfates, and the like; and the salts of organic acids such as acetates, propionates, benzoates, and the like. It is also preferred, although not required, that the preparation will contain a pharmaceutically or veterinary acceptable excipient that serves as a stabilizer. Examples of suitable carriers that also act as stabilizers for peptides include, without limitation, pharmaceutical grades of dextrose, sucrose, lactose, sorbitol, inositol, dextran, and the like. Other suitable carriers include, again without limitation, starch, cellulose, sodium or calcium phosphates, citric acid, glycine, polyethylene glycols (PEGs), and combinations thereof. The pharmaceutical or veterinary composition may be formulated for intravenous administration and other routes of local or systemic administration including, but not limited to, inhalation as a nasal spray, rectal compositions such as enemas or suppositories, and direct injection into the cerebrospinal fluid, spinal cord, or brain as desired. Dosing may vary and may be optimized using routine experimentation. Powder formulations for exosome delivery can be prepared by conventional methods for inhalation into the lungs of the subject to be treated or for intranasal administration into the nose and sinus cavities of a subject to be treated. For example, the compositions can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch. Exosomes can also be formulated as rectal compositions, such as suppositories or retention enemas, e.g., containing conventional suppository bases such as cocoa butter or other glycerides. Further, the exosomal compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt. For intravenous injections, water soluble versions of the microglial cell or exosome compositions can be administered by the drip method or direct injection, whereby a formulation including a pharmaceutical composition of the present invention and a physiologically-acceptable excipient is infused. Physiologically-acceptable excipients can include, for example, 5% dextrose, 0.9% saline, Ringer's solution, human serum albumin, or other suitable excipients.

The pharmaceutical and veterinary compositions of the present disclosure may be used as a neuro-regenerative therapeutic agent, including as an agent for reprogramming astroglial cells as a method of replenishing lost or damaged neuronal populations. Thus, in yet another aspect, the present disclosure provides a method for regenerating neurons, the method comprising:

(a) introducing a first and second chimeric nucleic acid sequence in a microglial host cell, the first chimeric nucleic acid sequence comprising as operably linked components:
(i) a nucleic acid sequence encoding an exosomal membrane polypeptide;
(ii) a nucleic acid sequence encoding a neural cell targeting polypeptide; and
(iii) a nucleic acid sequence encoding a nucleic acid binding polypeptide capable of binding a nucleic acid binding polypeptide recognition sequence; and
the second chimeric nucleic acid sequence comprising as operably linked components:
(i) a nucleic acid binding polypeptide recognition sequence; and
(ii) a nucleic acid sequence encoding a polypeptide capable of reprogramming an astroglial cell;
(b) growing the microglial host cell to produce exosomes;
(c) delivering the microglia and/or exosomes to sites of neural damage including, but not limited to, reactive astroglial cell populations; and
(d) expressing the polypeptide to reprogram an astroglial cell into a neuronal cell.

In yet further embodiments, the present disclosure provides methods for treating a patient with a pharmaceutical composition comprising exosomes or microglial cells in accordance with the present disclosure. Accordingly, the present disclosure further provides a method for treating a patient with exosomes or microglial cells of the present disclosure, said method comprising administering to the patient exosomes or microglial cells of the present disclosure, wherein the exosomes or microglial cells are administered in an amount sufficient to ameliorate a medical condition in the patient. In some embodiments, the medical condition is a neurodegenerative condition that may be ameliorated by administration of the exosomes or microglial cells of the present disclosure. In some embodiments, the medical condition is traumatic brain injury. In some embodiments, the medical condition is ischemic stroke.

The current disclosure further includes a use of exosomes to treat a person in need thereof wherein the exosomes comprise:

(I) a chimeric polypeptide comprising as operably linked components:
(i) an exosomal membrane polypeptide;
(ii) a neural cell targeting polypeptide; and
(iii) a nucleic acid binding polypeptide capable of binding a nucleic acid binding polypeptide recognition sequence; and
(II) a chimeric nucleic acid sequence comprising as operably linked components:
(i) a nucleic acid binding polypeptide recognition sequence; and
(ii) a nucleic acid sequence encoding a polypeptide of interest The person treated in accordance herewith may be treated to ameliorate traumatic brain injury or ischemic stroke, or symptoms associated therewith.

In yet further embodiments, the present disclosure provides methods for treating an animal with a veterinary composition comprising exosomes or microglial cells in accordance with the present disclosure. Accordingly, the present disclosure further provides a method for treating an animal with exosomes or microglial cells of the present disclosure, said method comprising administering to the animal exosomes or microglial cells of the present disclosure, wherein the exosomes or microglial cells are administered in an amount sufficient to ameliorate a health condition in the animal. In some embodiments, the health condition is a neurodegenerative condition that may be ameliorated by administration of the exosomes or microglial cells of the present disclosure. In some embodiments, the health condition is traumatic brain injury. In some embodiments, the health condition is ischemic stroke.

The current disclosure further includes a use of exosomes to treat an animal in need thereof wherein the exosomes comprise:
  (I) a chimeric polypeptide comprising as operably linked components:
    (i) an exosomal membrane polypeptide;
    (ii) a neural cell targeting polypeptide; and
    (iii) a nucleic acid binding polypeptide capable of binding a nucleic acid binding polypeptide recognition sequence; and
  (II) a chimeric nucleic acid sequence comprising as operably linked components:
    (i) a nucleic acid binding polypeptide recognition sequence; and
    (ii) a nucleic acid sequence encoding a polypeptide of interest.

The animal treated in accordance herewith may be treated to ameliorate traumatic brain injury or ischemic stroke, or symptoms associated therewith.

The above disclosure generally describes various aspects of methods and compositions of the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Example 1—System Overview

In accordance with one aspect, the mode of action of the herein disclosed system is that microglia, even when intravenously administered, innately migrate to regions of neural damage in the brain. In accordance with the methodology of the present disclosure, microglia are modified to include a chimeric polypeptide which is capable both of localizing to exosomes through its transmembrane LAMP-2B domain and binding a nucleic acid recognition sequence through its nucleic acid binding polypeptide domain. During the process of exosome biogenesis, the nucleic acid binding domain is initially localized in the cytoplasm, where it has access to cytoplasmic DNA species, including a second transfected chimeric nucleic acid plasmid vector. The inward budding of the multivesicular body (MVB) membrane to form intraluminal vesicles (ILVs), results in the nucleic acid binding polypeptide domain localizing in the lumen of ILVs. Bound nucleic acid vectors move in concert with the nucleic acid binding polypeptide, also localizing to the ILV lumen. As ILVs are released from the exosome-producing cell, as exosomes, the nucleic acid binding polypeptide and bound nucleic acid vector remain in the vesicle lumen, ultimately resulting in their presence in the lumen of exosomes (FIG. 2-FIG. 4). After being released from an exosome-producing cell, such as a microglial cell, the exosomes may be delivered to a target cell (i.e., recipient cell) where the exosomes are taken up and the cargo is delivered to the cytoplasm of the target cell. To enhance delivery of the nucleic acid vector to the target cell cytoplasm and, more specifically, its nucleus, the nucleic acid binding domain may be operably linked to a NLS and fused to LAMP-2B via a cleavable linker. In some embodiments, the cleavable linker is intein-based and autocatalytic in the reducing environment of the exosome, allowing release of the nucleic acid vector from the exosomal membrane. The bound NLS and nucleic acid binding polypeptide then targets the nucleic acid vector for expression in the nucleus of the target cell. In some embodiments, as a therapy for ischemic stroke or traumatic brain injury, expression of the nucleic acid vector encoding NeuroD1 (under the regulation of an astrocyte-specific promoter such as gfaABC$_1$D) by recipient reactive astrocytes may provide a method of replenishing damaged or dead neuronal cells.

This system may be implemented as follows: (a) a chimeric polypeptide comprising a neural cell targeting polypeptide (e.g., RVG) on the external terminus and a nucleic acid binding protein (e.g., a synthetic TAL effector) on the internal terminus of an exosomal membrane protein (e.g., LAMP-2B) is designed (FIG. 1); (b) a chimeric nucleic acid encoding the polypeptide of interest is designed (for example, NeuroD1 operably linked to a gfaABC$_1$D promoter; FIG. 1); (c) DNA sequences are generated (by traditional recombinant DNA assembly techniques such as restriction cloning and/or DNA synthesis) and inserted into a suitable expression vector containing the nucleic acid binding protein recognition sequence (e.g., a plasmid vector containing a TAL effector recognition sequence); (e) the chimeric vectors are transfected into a suitable cell line for producing exosomes (e.g., microglia); (f) the microglia or their exosomes are harvested; and (g) the microglia or their exosomes are administered (e.g., by intravenous injection).

Example 2—Exosomal Expression and Localization of Neural Cell Targeting Protein Construct To specifically target exosomes to neural cells, the N-terminus of the mouse exosomal membrane protein, LAMP-2B, was modified to include a Rabies Virus Glycoprotein (RVG) as previously described (Alvarez-Erviti et al., 2011). To verify appropriate expression and exosomal membrane localization of the modified LAMP-2B protein and to validate the viability of C-terminal modifications, Clover (a green fluorescent protein variant) was operably linked to the C-terminus.

Immortalized mouse microglia (EOC 13.31) and human embryonic kidney (HEK-293) cell cultures were lipofected (using Lipofectamine 3000 as per the manufacturer's protocols) with the chimeric pcDNA3.0-RVG-LAMP-2B-NLS-Clover plasmid. Unlipofected cultures were used as controls. One day prior to exosome isolation, the microglia culture medium was replaced with fresh medium centrifuged at 125,000×9 for 70 minutes to remove any pre-existing nanovesicles. During exosome collection, the culture medium was centrifuged at 300×g for 10 minutes to remove non-adherent cells, filtered (200 nm), and centrifuged at 125,000×g for 70 minutes. The resulting pellet was resuspended in either 1×PBS (for fluorescence detection) or 2%

PFA (for transmission electron microscopy; TEM) and stored at 4° C. The presence of exosomes was verified with TEM and samples were quantified and standardized with a Nanodrop 2000 (A280). Half of each of the exosome samples were lysed with sodium deoxycholate and fluorescence was measured using a QuantaMaster 60 fluorescence spectrofluorometer. The adherent microglia and HEK-293 cell cultures were rinsed with 1× phosphate-buffered saline (PBS), fixed with 4% paraformaldehyde (PFA) for 20 minutes, coverslipped with Vectashield plus DAPI, and immediately imaged using an Olympus FluoView FV1000 confocal laser scanning microscope.

Figure 5:
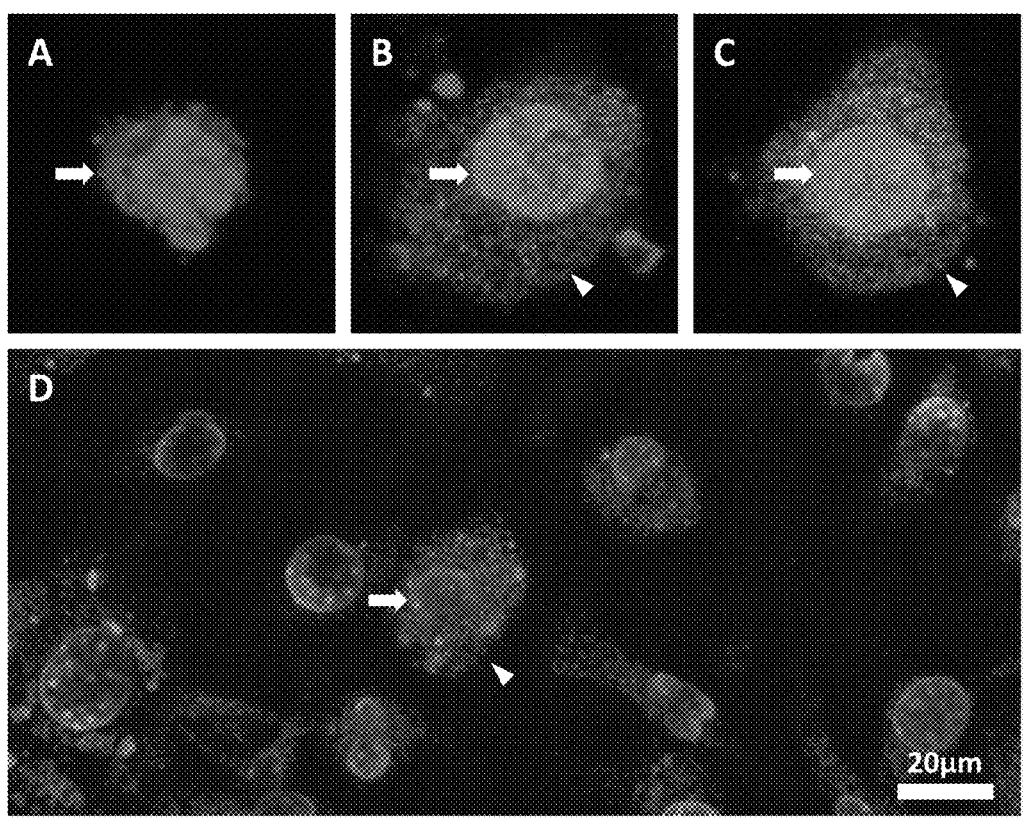
FIG. 5 depicts confocal microscopy images of both control and lipofected human embryonic kidney (HEK-293) cells and lipofected mouse microglia (EOC 13.31) counterstained with 4',6-diamidino-2-phenylindole (DAPI; blue; counterstained nuclei indicated with arrows). Cell cultures were lipofected with a variant of the first chimeric polypeptide where the cleavable polypeptide and the nucleic acid binding polypeptide were replaced with Clover, a green fluorescent protein (GFP) variant. (A) Both non-lipofected and vehicle control (not shown) HEK-293 cell cultures do not exhibit green cytoplasmic fluorescence. (B) HEK-293 cells lipofected with pcDNA3.0-Clover exhibit green fluorescence in the cytoplasm which can be attributed to Clover expression (green fluorescence indicated with arrowheads). (C) HEK-293 cells lipofected with pcDNA3.0-RVG-LAMP-2B-Clover exhibit green fluorescence in the cytoplasm which can be attributed to Clover expression and indicates that a C-terminal modification of LAMP-2B is viable. (D) Murine microglia cells transfected with pcDNA3.0-RVG-LAMP2B-Clover similarly exhibit green fluorescence in the cytoplasm attributable to Clover expression, indicating that this chimeric construct is also viable in mouse models.
Figure 6:
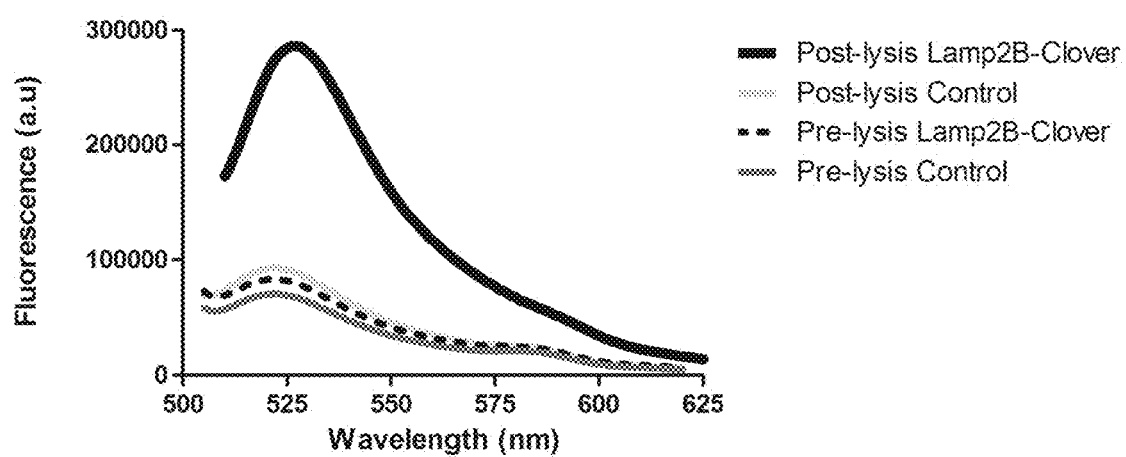
FIG. 6 depicts the fluorescence exhibited by exosomes isolated from unlipofected cell cultures and those lipofected with pcDNA3.0-RVG-LAMP-2B-Clover. Exosomes were excited at 489 nm and monitored for fluorescence with a spectrofluorometer from 505 nm-620 nm. Lysis (with sodium deoxycholate) of exosomes from cells transfected with pcDNA3.0-RVG-LAMP-2B-Clover results in elevated fluorescence peaking at 520 nm which is consistent with the fluorescence spectrum of Clover and indicates that the chimeric polypeptide is appropriately localized to exosomal lumens.

Unlike unlipofected controls, cultured microglia and HEK-293 cells lipofected with the chimeric RVG-LAMP-2B-Clover plasmid demonstrated cytoplasmic green fluorescence (FIG. 5). Upon lysis, exosomes isolated from transfected microglia and HEK-293 culture media exhibited elevated fluorescence (approximately three times that of both control and unlysed exosome samples) with an emission peak at approximately 515 nm (FIG. 6).

Example 3—Efficiency of Exosomal Packaging of Reprogramming Plasmid is Improved by Neural Cell Targeting Protein Construct An immortalized HEK-293 cell culture was co-lipofected (using Lipofectamine 3000 as per the manufacturer's protocols) with experimental versions of both the first chimeric nucleic acid sequence (encoding the neural cell targeting protein; pcDNA3.0-RVG-LAMP-2B-NLS-TALE) and one of two iterations of the second chimeric nucleic acid sequences (the "reprogramming" plasmid; gfaABC$_1$D-NeuroD1). The first chimeric nucleic acid sequence was comprised by the following operably linked components: a LAMP-2B exosomal membrane polypeptide; a cell targeting RVG polypeptide; a TAL-effector nucleic acid binding polypeptide; and a polypeptide providing a signal for nuclear localization in the target cell. Two versions of the second chimeric nucleic acid sequence were used. The first was comprised by the following operably linked components: a nucleic acid sequence encoding NeuroD1 regulated by a synthetic gfaABC$_1$D promoter; and a TAL-effector nucleic acid binding polypeptide recognition sequence (specific to the TAL-effector polypeptide in the first chimeric nucleic acid sequence). The second version included only the nucleic acid sequence encoding NeuroD1 regulated by a synthetic gfaABC$_1$D promoter (no TAL-effector nucleic acid binding polypeptide recognition sequence was included). Vehicle control cells were lipofected without the addition of either vector.

Co-lipofected cells were incubated in serum-free media for two days. Media was then collected and exosomes were isolated using a Qiagen exoEasy Maxi Kit (as per the manufacturer's protocols). DNA and RNA were extracted from the exosome preparations using a Qiagen QIAamp DNA Mini Kit (as per the manufacturer's protocols). DNA was then PCR amplified with either primers specific for gfaABC$_1$D-NeuroD1 (F: 5'-TCATAAAGCCCTCG-CATCCC-3'; SEQ. ID NO: 59; R: 5'-AGACCCCTGAGT-TCCTGTCA-3'; SEQ. ID NO: 60) or primers specific for the pcDNA3.0-LAMP-2B-NLS-TALE vector (F: 5'-GGAG-GTGGCGGATCAC-3'; SEQ. ID NO: 61; R: 5'-TAGAAGGCACAGTCGAGG-3'; SEQ. ID NO: 62).

RNA (in solution with the DNA) isolated from each of the exosome samples was reverse transcribed using a SuperScript III First-Strand Synthesis System (Invitrogen; as per the manufacturer's protocols) and a U6 small nuclear RNA-specific primer (5'-AAAATATGGAACGCTTCAC-GAATTTG-3'; SEQ. ID NO: 63). Quantitative real-time PCR (qRT-PCR) experiments were performed using a SsoAdvanced Universal SYBR Green Supermix (Bio-Rad; as per manufacturer's protocols) with a CFX96 Touch Real-Time PCR Detection System (Bio-Rad). U6 cDNA was used as the internal control. Primers specific to U6 (F: 5'-CTCGCTTCGGCAGCACATATACT-3'; SEQ. ID NO: 64 R: 5'-ACGCTTCACGAATTTGCGTGTC-3'; SEQ. ID NO: 65) and gfaABC$_1$D-NeuroD1 (F: 5'-TCATAAAGC-CCTCGCATCCC-3'; SEQ. ID NO: 59; R: 5'-AGACCCCT-GAGTTCCTGTCA-3'; SEQ. ID NO: 60) were used.

Gel electrophoresis of the PCR products confirmed the presence of the gfaABC$_1$D-NeuroD1 plasmid in both samples (with or without inclusion of the TAL effector binding site) based on the presence of an expected 132 base pair band. A band indicating the presence of pcDNA3.0-RVG-LAMP-2B-NLS-TALE was not evident for either DNA preparation.

Figure 7:
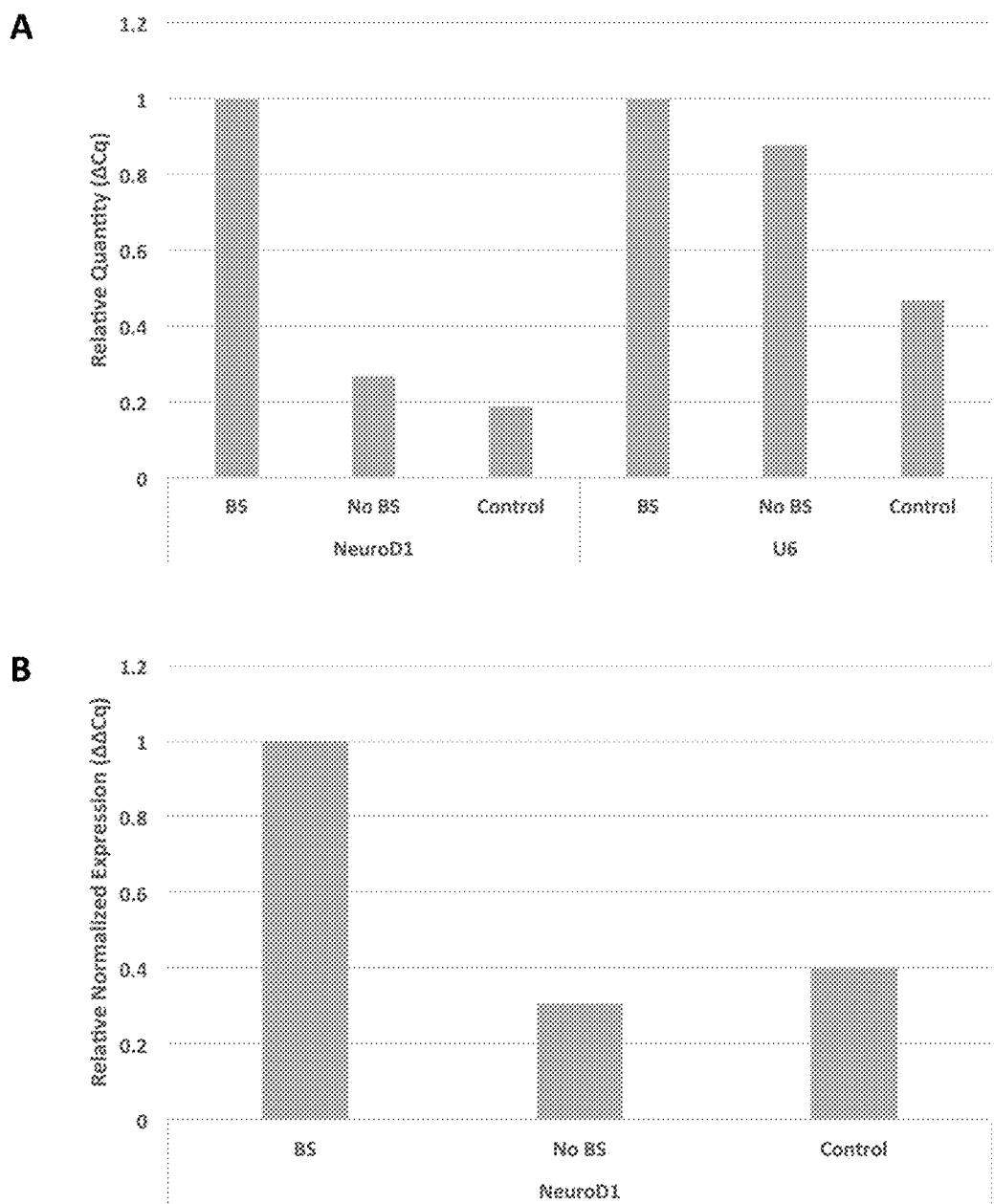
FIG. 7 depicts the quantitative real-time polymerase chain reaction (qRT-PCR) results on DNA samples isolated from exosomes from cell cultures lipofected without plasmid (Control), with both pcDNA3.0-RVG-LAMP-2B-NLS-TALE and gfaABC$_1$D-NeuroD1 with the TAL effector binding site (BS), or with both pcDNA3.0-RVG-LAMP-2B-NLS-TALE and gfaABC$_1$D-NeuroD1 without the TAL effector binding site (No BS). U6 small nuclear RNA cDNA was used as an internal control. (A) Relative quantity (delta quantification cycle; ΔCq) of gfaABC$_1$D-NeuroD1 plasmid and U6 cDNA evident in each sample. (B) Relative normalized expression (delta delta quantification cycle; ΔΔCq) of gfaABC$_1$D-NeuroD1 corrected for U6 cDNA in each sample.

When normalized to U6 small nuclear RNA expression, qRT-PCR revealed a three-fold increase in gfaABC$_1$D-NeuroD1 plasmid isolated from exosome samples when the lipofected plasmid contained the TAL effector binding site relative to those without the TAL effector binding site, suggesting an increase in exosomal packaging efficiency of the gfaABC$_1$D-NeuroD1 plasmid when anchored to the TAL effector nucleic acid binding protein (FIG. 7).

Example 4—Astrocytic Expression of NeuroD1 Results in a Neuronal Phenotype

An immortalized astrocyte (C8-D30) cell culture was lipofected (using Lipofectamine 3000 as per the manufacturer's protocols) with an experimental version of the second chimeric nucleic acid sequence comprising NeuroD1 operably linked to a CMV promoter and an IRES-GFP element. Briefly, adherent astrocytes were rinsed with 1×PBS and fixed with 4% PFA for 20 minutes. Fixed cells were rinsed twice with 1×PBS, blocked with 1×PBS plus 0.3% Triton-X and 3% goat serum for 45 minutes, and incubated with 1:100 anti-GFAP for 2 hours at room temperature. Cells were rinsed twice with 1×PBS and primary antibodies were labeled with 1:200 anti-rabbit-Alexa Fluor 594 in blocking buffer for 1 hour at room temperature. Slides were rinsed twice with 1×PBS, coverslipped with Vectashield plus DAPI, and immediately imaged using an Olympus FluoView FV1000 confocal laser scanning microscope.

Figure 8:
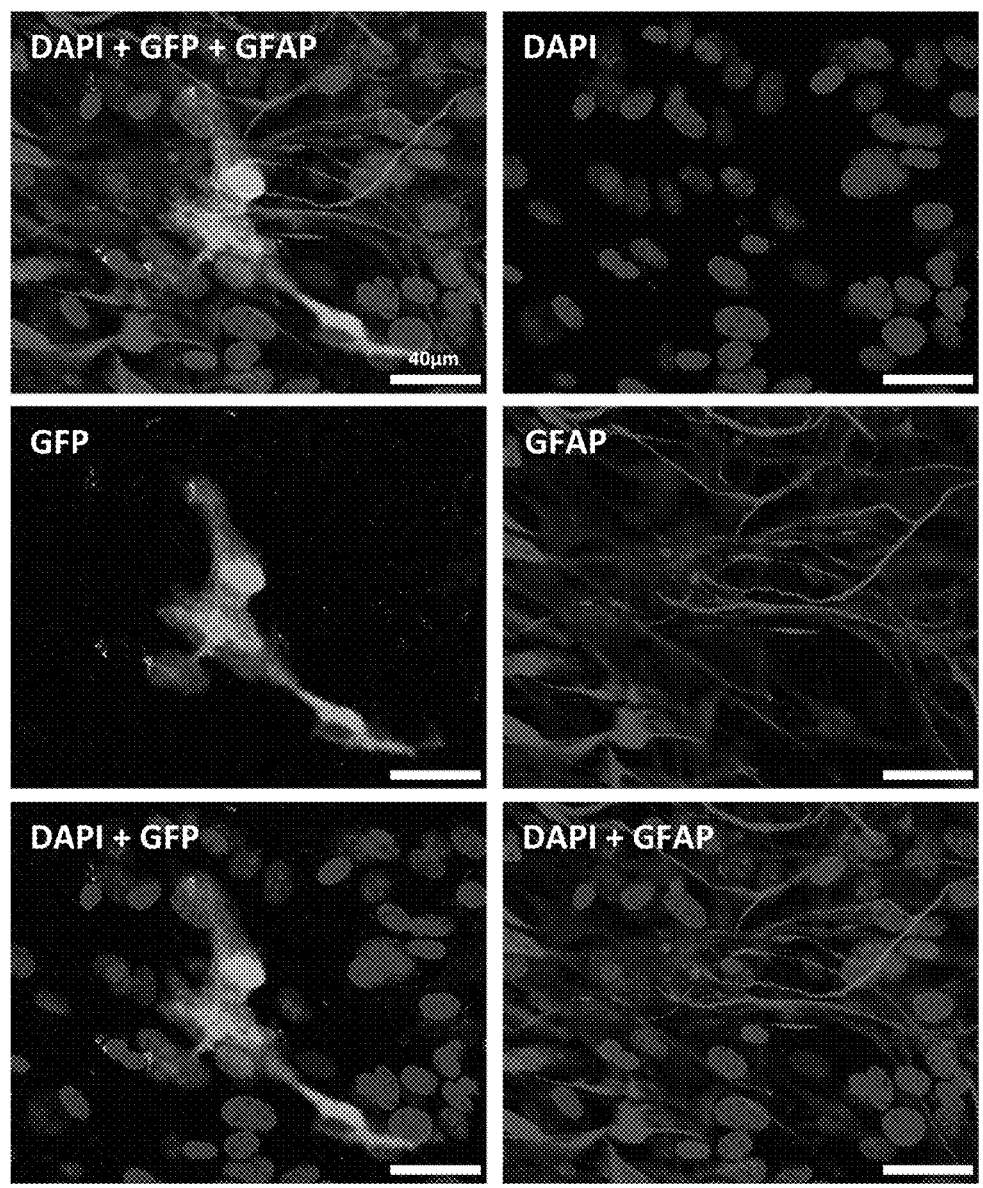
FIG. 8 depicts confocal microscopy images of an immortal astrocyte (C8-D30) cell culture lipofected with an experimental version of the second chimeric nucleic acid sequence comprising NeuroD1 operably linked to a constitutive cytomegalovirus (CMV) promoter and an internal ribosome entry site (IRES) linked to a green fluorescent protein (GFP). This experimental embodiment provides a method of visually confirming cellular expression of NeuroD1 by associating it with GFP expression. Adherent astrocytes were fixed with 4% paraformaldehyde, immunolabeled with 1:100 anti-GFAP and 1:200 anti-rabbit-Alexa Fluor 594 (red), and counterstained with DAPI (blue). GFP expression (green) is evident in the cytoplasm of successfully transfected cells, which do not exhibit co-staining with GFAP (a reactive astrocyte marker). The loss of GFAP expression suggests reprogramming of the reactive astrocytes.

GFP expression was evident in successfully transfected cells, which do not exhibit co-staining with GFAP (a reactive astrocyte marker; FIG. 8).

Example 5—Functional Recovery from Ischemic Stroke in a Mouse Model by Reprogramming of Reactive Astrocytes In Vivo Non-adherent bone marrow cells are first obtained from 2-3 month old mice, cultured, and differentiated into microglia according to Hinze and Stolzing (2012). Briefly, femurae and tibiae are isolated, opened and centrifuged to obtain bone marrow, which is cultured in Dulbecco's modified eagle medium (DMEM) supplemented with 10% fetal calf serum (FCS), $10^{-8}$M dexamethasone and 100 units/ml Penicillin/Streptomycin. After 24 hours, the non-adherent cells are flushed off and transferred to a new dish. Cells are then differentiated for 6 days in 10 ml DMEM supplemented with 10% FCS, 50% astrocyte-conditioned medium (ACM), and 20 ng/ml granulocyte-monocyte colony stimulating factor (GM-CSF).

Microglial cultures are then lipofected (using Lipofectamine 3000 as per the manufacturer's protocols) with the chimeric pcDNA3.0-RVG-LAMP-2B-NLS-TALE and gfaABC$_1$D-NeuroD1-IRES-GFP plasmids. To assess the in vivo reprogramming capability of these cells, a rodent model is used. Specifically, adult male C57BL/6J mice are given cerebral infarcts using the photothrombotic surgical method (Brown et al., 2007; Labat-gest and Tomasi, 2013). Briefly, animals are sedated using buprenorphine and isoflurane and fitted into a rodent stereotaxic frame. A midline incision on the scalp is made and the skin retracted to expose the skull. A dental drill is then used to thin the skull over motor cortex. Following an intraperitoneal injection (100 mg/kg) of Rose-Bengal (1% w/v), superficial motor cortex is illuminated with a green laser (532 nm, 17 mW) for 15 minutes to induce clotting and an ischemic stroke. Control groups will receive either a Rose-Bengal injection and no laser illumination, or illumination and no injection. One day after surgery, experimental group animals are injected in the tail vein with 500 µl of microglial cells suspended in sterile cerebrospinal fluid (CSF). Control animals receive the CSF injection without microglia cells. Animals are then re-tested on measures of motor skill that they had received training for prior to the infarct surgery. These include but are not limited to: the cylinder test, hanging wire test, pole test, and adhesive removal test (Li et al., 2014). Testing sessions will occur on day 4, 6, 10, and 14 following surgery. Mice that have received treatment with microglia are expected to exhibit gradually improving performance in the behavioral tasks, demonstrating the functional recovery promoted by the reprogramming of reactive astrocytes.

Upon completion of behavioral testing, animals will be deeply anesthetized with an intraperitoneally-administered overdose of sodium pentobarbital (100 mg/kg) and then perfused with phosphate-buffered saline (PBS) and 4% paraformaldehyde (PFA). Brains will then be post-fixed for 24 hours in 4% PFA and subsequently cryoprotected in 30% sucrose (in PBS) prior to sectioning. 40 µm tissue sections containing motor cortex are then washed with PBS, blocked with 1×PBS plus 0.3% Triton X-100 and 5% goat serum for 2 hours, and incubated overnight with 1:500 rabbit anti-GFAP antibody in 1×PBS plus 0.3% Triton X-100 at room temperature with agitation. Sections are rinsed twice with 1×PBS plus 0.3% Triton X-100 and primary antibodies are then labeled with 1:500 anti-rabbit-Alexa Fluor 594 secondary antibodies in PBS plus 0.3% Triton X-100 overnight at room temperature. Sections are then rinsed twice with 1×PBS, mounted on slides with Vectashield plus DAPI, coverslipped, and immediately imaged using a confocal laser scanning microscope. Similar to what was demonstrated in Example 4, it is expected that successfully reprogrammed reactive astrocytes in the damaged motor cortex will exhibit GFP expression which will not co-localize with GFAP.

REFERENCES

Alvarez-Erviti, L., et al. (2011). "Delivery of siRNA to the mouse brain by systemic injection of targeted exosomes." *Nat Biotech* 29(4): 341-345.

Altschul et al. (1990). "Basic local alignment search tool." *J. Molec. Biol.* 215 (3): 403-410.

Ausubel, F. (1989). Current Protocols in Molecular Biology, John Wiley & Sons, N.Y., 6.3.1.-6.3.6.

Balyasnikova, I. V., et al. (2010). "Genetic modification of mesenchymal stem cells to express a single-chain antibody against EGFRvIII on the cell surface." *J. Tissue Eng. Regen. Med.* 4(4): 247-258.

Becher. B. and J. P. Antel (1996). "Comparison of phenotypic and functional properties of immediately ex vivo and cultured human adult microglia." *Glia* 18: 1-10.

Bronstein, R., et al. (2013). "Culturing Microglia from the Neonatal and Adult Central Nervous System." *Journal of visualized experiments: JoVE* (78).

Brown, C. E., Li, P., Boyd, J. D., Delaney, K. R., Murphy, T. H., 2007. Extensive turnover of dendritic spines and vascular remodeling in cortical tissues recovering from stroke. *The Journal of Neuroscience* 27, 4101-4109.

Carillo, H. and Lipman, J. (1988). The multiple sequence alignment problem in biology. *SIAM J. Applied Math.* 48:1073-1082.

Devereux et al. (1984). A comprehensive set of sequence analysis programs for the VAX. *Nucleic Acids Res.* 12: 387-395.

El-Andaloussi, S., et al. (2012). "Exosome-mediated delivery of siRNA in vitro and in vivo." *Nat. Protocols* 7(12): 2112-2126.

Fassler, M., et al. (2013). "Preferential lentiviral targeting of astrocytes in the central nervous system." *PLoS One* 8(10): e76092.

Felgner, P. L, et al. (1987). "Lipofection: a highly efficient, lipid-mediated DNA-transfection procedure." *Proceedings of the National Academy of Sciences* 84(21): 7413-7417.

Finkelstein, E. C., Corso, P. S., and T. R. Miller (2006). "*The Incidence and Economic Burden of Injuries in the United States*." New York: Oxford University Press.

Ford, A. L, Goodsall, A. L., Hickey, W. F., and J. D. Sedgwick (1995). "Normal adult ramified microglia separated from other central nervous system macrophages by flow cytometric sorting. Phenotypic differences defined and direct ex vivo antigen presentation to myelin basic protein-reactive CD4+ T cells compared." *J Immunol.* 154(9): 4309-21.

Heidenreich, P. A., et al. (2011). "Forecasting the future of cardiovascular disease in the United States: a policy statement from the American Heart Association." *Circulation* 123: 933-944.

Henikoff S. & Henikoff, J. G. (1992). "Amino acid substitution matrices from protein blocks." *Proc. Natl. Acad. Sci. USA* 89 (22): 10915-10919.

Hinze, A. and A. Stolzing (2012). "Microglia differentiation using a culture system for the expansion of mice non-adherent bone marrow stem cells." *Journal of Inflammation (London. England)* 9: 12-12.

Kim, T. K. and J. H. Eberwine (2010). "Mammalian cell transfection: the present and the future." *Analytical and Bioanalytical Chemistry* 397(8): 3173-3178.

Kingston, R. E., et al. (2001). "Calcium Phosphate Transfection." *Current Protocols in Molecular Biology*. John Wiley & Sons, Inc.

Kreutzberg, G. W. (1996). "Microglia: a sensor for pathological events in the CNS." *Trends in Neurosciences* 19(8): 312-318.

Labat-gest, V., Tomasi, S., 2013. Photothrombotic Ischemia: A Minimally Invasive and Reproducible Photochemical Cortical Lesion Model for Mouse Stroke Studies. *Journal of Visualized Experiments: JoVE*. 50370.

Lee, J.-K. and M. Tansey (2013). "Microglia Isolation from Adult Mouse Brain." *Microglia*. B. Joseph and J. L Venero, Humana Press. 1041: 17-23.

Lesk, A. M. (1988). Computational Molecular Biology, Oxford University Press, New York, Biocomputing: Informatics and Genomics Projects.

Li, H., Zhang, N., Lin, H.-Y., Yu, Y., Cai, Q.-Y., Ma, L., Ding, S., 2014. Histological, cellular and behavioral assessments of stroke outcomes after photothrombosis-induced ischemia in adult mice. *BMC Neuroscience* 15, 1-13.

Moussaud, S. and H. J. Draheim (2010). "A new method to isolate microglia from adult mice and culture them for an extended period of time." *Journal of Neuroscience Methods* 187(2): 243-253.

Muratovska, A. and Eccles, M. R. (2004). "Conjugate for efficient delivery of short interferring RNA (siRNA) into mammalian cells." *FEBS Letters* 558: 36-38.

Mutalik, V. K, Qi, L, Guimaraes, J. C., Lucks, J. B., and A. P. Arkin (2012). "Rationally designed families of orthogonal RNA regulators of translation." *Nature Chemical Biology* 8(5): 447-454.

Needleman, S. B. and Wunsch, C D (1970). "A general method applicable to the search for similarities in the amino acid sequences of two proteins." *J. Mol. Biol.*, 1970, 48 (3): 443-453.

Public Health Agency of Canada (2009). "Tracking heart disease and stroke in Canada." Retrieved from http://www.phac-aspc.gc.ca/publicat/2009/cvd-avc/pdf/cvd-avs-2009-eng.pdf Sambrook et al., (1989). Molecular Cloning, a Laboratory Manual, Cold Spring Harbor Laboratory Press, 1989, Vol. 3.

Sanjana, N. E., et al. (2013). "A transcription activator-like effector (TALE) toolbox for genome engineering." *Nature Protocols* 7(10): 171-192.

Schildge, S., et al. (2013). "Isolation and culture of mouse cortical astrocytes." *Journal of visualized experiments: JoVE* (71).

Smith, T. F. and Waterman, M. S. (1981). "Comparison of biosequences." Adv. Appl. Math. 2 (4): 482-489.

Stitchel, C. C. & H. W. Müller (1988). "The CNS lesion scar: new vistas on an old regeneration barrier." *Cell and Tissue Research* 294(1): 1-9.

Thompson, J D, Higgines, D G and Gibson T J (1994). "Clustal W: improving the sensitivity of progressive multiple sequence alignment through sequence weighting, position-specific gap penalties and weight matrix choice." *Nucleic Acid Res.* 22(22): 4673-4680.

Witting, A. and T. Möller (2011). "Microglia Cell Culture: A Primer for the Novice." *In Vitro Neurotoxicology*. L G. Costa, G. Giordano and M. Guizzetti, Humana Press. 758: 49-66.

Youn, P., Chen, Y. and Furgeson (2014). "A myristoylated cell-penetrating peptide bearing a transferrin receptor-targeting sequence for neuro-targeted siRNA delivery." *Molecular Pharmaceutics* 11(2): 486-495.

---

The invention claimed is:

1. A method of expressing a polypeptide of interest in an astroglial cell, the method comprising
   (a) introducing a first and second chimeric nucleic acid sequence in a microglial host cell,
   (1) the first chimeric nucleic acid sequence comprising as operably linked components:
      (i) a nucleic acid sequence encoding an exosomal membrane polypeptide;
      (ii) a nucleic acid sequence encoding a neural cell targeting polypeptide; and
      (iii) a nucleic acid sequence encoding a nucleic acid binding polypeptide capable of binding a nucleic acid binding polypeptide recognition sequence; and
   (2) the second chimeric nucleic acid sequence comprising as operably linked components:
      (i) a nucleic acid binding polypeptide recognition sequence; and
      (ii) a nucleic acid sequence encoding a polypeptide of interest;
   (b) growing the microglial host cell to produce exosomes;
   (c) delivering the exosomes to an astroglial cell; and
   (d) expressing the polypeptide of interest in the astroglial cell.

2. The method according to claim 1 wherein the first chimeric nucleic acid sequence additionally comprises:
   (iv) a nucleic acid sequence encoding a cleavable polypeptide; or
   (v) a nucleic acid sequence encoding a polypeptide providing a signal for nuclear localization in the astroglial cell.

3. The method according to claim 1 wherein the exosomes are produced in microglia cells in vitro.

4. The method according to claim 3 wherein the exosomes are separated from the microglia cells and provided to a human or an animal in need thereof in a manner that permits expression in astroglial cells of the human or the animal.

5. The method according to claim 1 wherein the exosomes are produced in microglia cells in vivo.

6. The method according to claim 5 wherein the microglia cells are provided to a human or an animal in need thereof in a manner that permits expression in astroglial cells of the human or animal.

7. The method according to claim 1 wherein the polypeptide of interest is a polypeptide capable of reprogramming astroglial cells into neurons.

8. The method according to claim 7 wherein the polypeptide of interest is NeuroD1.

9. The method according to claim 7 wherein the polypeptide of interest comprises the polypeptide set forth by SEQ.ID NO: 49; SEQ.ID NO: 50; SEQ.ID NO: 51; SEQ.ID NO: 52; or SEQ.ID NO: 53.

10. The method according to claim 1 wherein the exosomal membrane polypeptide is LAMP-2B.

11. The method according to claim 10 wherein the exosomal membrane polypeptide comprises the polypeptide set forth by SEQ.ID NO: 33; SEQ.ID NO: 34; SEQ.ID NO: 35; SEQ.ID NO: 36; SEQ.ID NO: 37; SEQ.ID NO: 38 SEQ.ID NO: 39; SEQ.ID NO: 40; SEQ.ID NO: 41; SEQ.ID NO: 42; SEQ.ID NO: 43 or SEQ.ID NO: 44.

12. The method according to claim 1 wherein the neural cell targeting polypeptide is RVG.

13. The method according to claim 12 wherein the neural cell targeting polypeptide comprises the polypeptide set forth by SEQ.ID NO: 45 or SEQ.ID NO: 46.

14. The method according to claim 1 wherein the nucleic acid binding polypeptide is Gal4 or TAL effector polypeptide.

15. The method according to claim 14 wherein the Gal4 polypeptide comprises the polypeptide set forth by SEQ.ID NO: 47.

16. The method according to claim 1 wherein the nucleic acid sequence comprising a nucleic acid binding polypeptide recognition sequence is the Gal4 UAS sequence or the TAL effector polypeptide recognition sequence.

17. The method according to claim 16 wherein the nucleic acid sequence comprising a nucleic acid binding polypeptide recognition sequence comprises the nucleic acid sequence set forth by SEQ.ID NO: 17 or SEQ.ID NO: 18.

18. The method according to claim 7 wherein the astroglial cell is reprogrammed into neurons.

19. A composition comprising microglia cells capable of producing exosomes, wherein the exosomes comprise:
   (I) a chimeric polypeptide comprising as operably linked components:
      (i) an exosomal membrane polypeptide;
      (ii) a neural cell targeting polypeptide; and
      (iii) a nucleic acid binding polypeptide capable of binding a nucleic acid binding polypeptide recognition sequence; and (II) a chimeric nucleic acid sequence comprising as operably linked components:
  (i) a nucleic acid binding polypeptide recognition sequence; and
  (ii) a nucleic acid sequence encoding a polypeptide of interest.

20. A composition comprising substantially pure exosomes comprising:
(I) a chimeric polypeptide comprising as operably linked components:
  (i) an exosomal membrane polypeptide;
  (ii) a neural cell targeting polypeptide; and
  (iii) a nucleic acid binding polypeptide capable of binding a nucleic acid binding polypeptide recognition sequence; and
(II) a chimeric nucleic acid sequence comprising as operably linked components:
  (i) a nucleic acid binding polypeptide recognition sequence; and
  (ii) a nucleic acid sequence encoding a polypeptide of interest.

21. The method of claim 14 wherein the TAL effector polypeptide comprises the polypeptide set forth by SEQ.ID NO: 48.

* * * * *

SEQUENCE LISTING

```
<160> NUMBER OF SEQ ID NOS: 58

<210> SEQ ID NO 1
<211> LENGTH: 1230
<212> TYPE: DNA
<213> ORGANISM: Homo sapiens

<400> SEQUENCE: 1
atggtgtgct tcaggctgtt ccccgtgccc ggcagcggcc tggtgctggt gtgcctggtg      60
ctgggcgccg tgaggagcta cgccctggag ctgaacctga ccgacagcga gaacgccacc     120
tgcctgtacg ccaagtggca gatgaacttc accgtgaggt acgagaccac caacaagacc     180
tacaagaccg tgaccatcag cgaccacggc accgtgacct acaacggcag catctgcggc     240
gacgaccaga acggcgccaa gatcgccgtg cagttcggcc ccggcttcag ctggatcgcc     300
aacttcacca aggccgccag cacctacagc atcgacagcg tgagcttcag ctacaacacc     360
ggcgacaaca ccaccttccc cgacgccgag gacaagggca tcctgaccgt ggacgagctg     420
ctggccatca ggatccccct gaacgacctg ttcaggtgca acagcctgag caccctggag     480
aagaacgacg tggtgcagca ctactgggac gtgctggtgc aggccttcgt gcagaacggc     540
accgtgagca ccaacgagtt cctgtgcgac aaggacaaga ccagcaccgt ggccccacc     600 atccacacca ccgtgcccag ccccaccacc accccaccc ccaaggagaa gcccgaggcc     660
ggcacctaca gcgtgaacaa cggcaacgac acctgcctgc tggccaccat gggcctgcag     720
ctgaacatca cccaggacaa ggtggccagc gtgatcaaca tcaaccccaa caccacccac     780
agcaccggca gctgcaggag ccacaccgcc ctgctgaggc tgaacagcag caccatcaag     840
tacctggact tcgtgttcgc cgtgaagaac gagaacaggt tctacctgaa ggaggtgaac     900
atcagcatgt acctggtgaa cggcagcgtg ttcagcatcg ccaacaacaa cctgagctac     960
tgggacgccc ccctgggcag cagctacatg tgcaacaagg agcagaccgt gagcgtgagc    1020
```

```
ggcgccttcc agatcaacac cttcgacctg agggtgcagc ccttcaacgt gacccagggc    1080
aagtacagca ccgcccagga gtgcagcctg acgacgaca ccatcctgat ccccatcatc     1140
gtgggcgccg gcctgagcgg cctgatcatc gtgatcgtga tcgcctacgt gatcggcagg    1200
aggaagagct acgccggcta ccagaccctg                                      1230
```

<210> SEQ ID NO 2
<211> LENGTH: 1269
<212> TYPE: DNA
<213> ORGANISM: Mus musculus

<400> SEQUENCE: 2

```
atgtgcctct ctccggttaa aggcgcaaag ctcatcctga tctttctgtt cctaggagcc    60
gttcagtcca atgcattgat agttaatttg acagattcaa agggtacttg cctttatgct    120
cgaggttccg gaggtgcaga atgggagatg aatttcacaa taacatatga aactacaaac    180
caaaccaata aaactataac cattgcagta cctgacaagg cgacacacga tggaagcagt    240
tgtggggatg accggaatag tgccaaaata atgatacaat ttggattcgc tgtctcttgg    300
gctgtgaatt ttaccaagga agcatctcat tattcaattc atgacatcgt gctttcctac    360
aacaccagtg atagcacagt atttcctggt gctgtagcta aaggagttca tactgttaaa    420
aatcctgaga atttcaaagt tccattggat gtcatcttta agtgcaatag tgttttaact    480
tacaacctga ctcctgtcgt tcagaaatat gggggtattc acctgcaagc ttttgtccaa    540
aatggtacag tgagtaaaaa tgaacaagtg tgtgaagaag accaaactcc caccactgtg    600
gcacccatca ttcacaccac tgccccgtcg actacaacta cactcactcc aacttcaaca    660
cccactccaa ctccaactcc aactccaacc gttggaaact acagcattag aaatggcaat    720
actacctgtc tgctggctac catggggctt cagctgaaca tcactgagga aaggtgcct    780 ttcatttta acatcaaccc tgccacaacc aacttcaccg gcagctgtca acctcaaagt    840
gctcaactta gctgaacaa cagccaaatt aagtatcttg actttatctt tgctgtgaaa    900
aatgaaaaac ggttctatct gaaggaagtg aatgtctaca tgtatttggc taatggctca    960
gctttcaaca tttccaacaa gaaccttagc ttctgggatg cccctctggg aagttcttat    1020
atgtgcaaca agagcaggt gctttctgtg tccagagcgt ttcagatcaa caccttaac    1080 ctaaaggtgc aacctttaa tgtgacaaaa ggacagtatt ctacagccca ggagtgttcg    1140
ctggatgatg acaccattct aataccaatt atagttggtg ctggtctttc aggcttgatt    1200
atcgttatag tgattgctta cctaattggc agaagaaaga cctatgctgg atatcagact    1260
ctgactaga                                                             1269
```

<210> SEQ ID NO 3
<211> LENGTH: 1230
<212> TYPE: DNA
<213> ORGANISM: Homo sapiens

<400> SEQUENCE: 3

```
atggtgtgct caggctgtt ccccgtgccc ggcagcggcc tggtgctggt gtgcctggtg     60
ctgggcgccg tgaggagcta cgccctggag ctgaacctga ccgacagcga gaacgccacc    120
tgcctgtacg ccaagtggca gatgaacttc accgtgaggt acgagaccac caacaagacc    180
tacaagaccg tgaccatcag cgaccacggc accgtgacct acaacggcag catctgcggc    240
gacgaccaga acggccccaa gatcgccgtg cagttcggcc ccggcttcag ctggatcgcc    300
aacttcacca aggccgccag cacctacagc atcgacagcg tgagcttcag ctacaacacc    360
```

```
ggcgacaaca ccaccttccc cgacgccgag acaagggca tcctgaccgt ggacgagctg      420
ctggccatca ggatcccct gaacgacctg ttcaggtgca acagcctgag cacctggag       480 aagaacgacg tggtgcagca ctactgggac gtgctggtgc aggccttcgt gcagaacggc     540
accgtgagca ccaacgagtt cctgtgcgac aaggacaaga ccagcaccgt ggccccacc      600 atccacacca ccgtgcccag ccccaccacc accccaccc caaggagaa gcccgaggcc       660 ggcacctaca cgtgaacaa cggcaacgac acctgcctgc tggccaccat gggcctgcag     720
ctgaacatca cccaggacaa ggtggccagc gtgatcaaca tcaaccccaa caccacccac   780
agcaccggca gctgcaggag ccacaccgcc ctgctgaggc tgaacagcag caccatcaag     840
tacctggact tcgtgttcgc cgtgaagaac gagaacaggt tctacctgaa ggaggtgaac     900
atcagcatgt acctggtgaa cggcagcgtg ttcagcatcg ccaacaacaa cctgagctac     960
tgggacgccc ccctgggcag cagctacatg tgcaacaagg agcagaccgt gagcgtgagc    1020
ggcgccttcc agatcaacac cttcgacctg agggtgcagc ccttcaacgt gacccagggc    1080
aagtacagca ccgcccagga ctgcagcgcc gacgacgaca acttcctggt gcccatcgcc    1140
gtgggcgccg ccctggccgg cgtgctgatc ctggtgctgc tggcctactt catcggcctg    1200
aagcaccacc acgccggcta cgagcagttc                                      1230

<210> SEQ ID NO 4
<211> LENGTH: 1245
<212> TYPE: DNA
<213> ORGANISM: Mus musculus

<400> SEQUENCE: 4
atgtgcctga gcccgtgaa gggcgccaag ctgatcctga tcttcctgtt cctgggcgcc       60
gtgcagagca acgccctgat cgtgaacctg accgacagca agggcaccctg cctgtacgcc    120 gagtggggaga tgaacttcac catcacctac gagaccacca ccagaccaa caagaccatc     180 accatcgccg tgcccgacaa ggccacccac gacggcagca gctgcggcga cgacaggaac    240
agcgccaaga tcatgatcca gttcggcttc gccgtgagct gggccgtgaa cttcaccaag    300
gaggccagcc actacagcat ccacgacatc gtgctgagct acaacaccag cgacagcacc    360
gtgttccccg cgccgtggc caagggcgtg cacaccgtga agaaccccga gaacttcaag     420 gtgccctgg acgtgatctt caagtgcaac agcgtgctga cctacaacct gacccccgtg     480
gtgcagaagt actggggcat ccacctgcag gccttcgtgc agaacggcac cgtgagcaag    540
aacgagcagg tgtgcgagga ggaccagacc cccaccaccg tggccccat catccacacc     600 accgcccca gcaccaccac caccctgacc cccaccagca cccccacccc cacccccacc    660 cccacccca ccgtgggcaa ctacagcatc aggaacggca acaccacctg cctgctggcc    720
accatgggcc tgcagctgaa catcaccgag gagaaggtgc ccttcatctt caacatcaac    780
cccgccacca ccaacttcac cggcagctgc agccccaga cgcccagct gaggctgaac     840 aacagccaga tcaagtacct ggacttcatc ttcgccgtga agaacgagaa gaggttctac    900
ctgaaggagg tgaacgtgta catgtacctg gccaacggca gcgccttcaa catcagcaac    960
aagaacctga gcttctggga cgccccctg ggcagcagct acatgtgcaa caaggagcag    1020
gtgctgagcg tgagcagggc cttccagatc aacaccttca acctgaaggt gcagcccttc    1080
aacgtgacca agggccagta cagcaccgcc caggactgca gcgccgacga ggacaacttc    1140
ctggtgccca tcgccgtggg cgccgccctg ggcggcgtgc tgatcctggt gctgctggcc    1200
```

```
tacttcatcg gcctgaagag gcaccacacc ggctacgagc agttc            1245
```

<210> SEQ ID NO 5
<211> LENGTH: 1233
<212> TYPE: DNA
<213> ORGANISM: Homo sapiens

<400> SEQUENCE: 5

```
atggtgtgct tcaggctgtt ccccgtgccc ggcagcggcc tggtgctggt gtgcctggtg     60
ctgggcgccg tgaggagcta cgccctggag ctgaacctga ccgacagcga gaacgccacc    120
tgcctgtacg ccaagtggca gatgaacttc accgtgaggt acgagaccac caacaagacc    180
tacaagaccg tgaccatcag cgaccacggc accgtgacct acaacggcag catctgcggc    240
gacgaccaga acggccccaa gatcgccgtg cagttcggcc ccggcttcag ctggatcgcc    300
aacttcacca aggccgccag cacctacagc atcgacagcg tgagcttcag ctacaacacc    360
ggcgacaaca ccaccttccc cgacgccgag gacaagggca tcctgaccgt ggacgagctg    420
ctggccatca ggatccccct gaacgacctg ttcaggtgca cagcctgag cacccctggag   480
aagaacgacg tggtgcagca ctactgggac gtgctggtgc aggccttcgt gcagaacggc    540
accgtgagca ccaacgagtt cctgtgcgac aaggacaaga ccagcaccgt ggccccccacc   600
atccacacca ccgtgcccag ccccaccacc accccccacc ccaaggagaa gccccgaggcc   660
ggcacctaca cgtgaacaa cggcaacgac acctgcctgc tggccaccat gggcctgcag    720
ctgaacatca cccaggacaa ggtggccagc gtgatcaaca tcaaccccaa caccacccac    780
agcaccggca gctgcaggag ccacaccgcc ctgctgaggc tgaacagcag caccatcaag    840
tacctggact tcgtgttcgc cgtgaagaac gagaacaggt tctacctgaa ggaggtgaac    900
atcagcatgt acctggtgaa cggcagcgtg ttcagcatcg ccaacaacaa cctgagctac    960
tgggacgccc ccctgggcag cagctacatg tgcaacaagg agcagaccgt gagcgtgagc   1020
ggcgccttcc agatcaacac cttcgacctg agggtgcagc ccttcaacgt gacccagggc   1080
aagtacagca ccgccgagga gtgcagcgcc gacagcgacc tgaacttcct gatccccgtg   1140
gccgtgggcg tggcccctgg cttcctgatc atcgtggtgt tcatcagcta catgatcggc   1200
aggaggaaga gcaggaccgg ctaccagagc gtg                                1233
```

<210> SEQ ID NO 6
<211> LENGTH: 1245
<212> TYPE: DNA
<213> ORGANISM: Mus musculus

<400> SEQUENCE: 6

```
atgtgcctga gccccgtgaa gggcgccaag ctgatcctga cttcctgtt cctgggcgcc     60
gtgcagagca acgccctgat cgtgaacctg accgacagca agggcacctg cctgtacgcc   120
gagtgggaga tgaacttcac catcacctac gagaccacca ccagaccaa caagaccatc    180
accatcgccg tgcccgacaa ggccacccac gacggcagca gctgcggcga cgacaggaac   240
agcgccaaga tcatgatcca gttcggcttc gccgtgagct gggccgtgaa cttcaccaag    300
gaggccagcc actacagcat ccacgacatc gtgctgagct acaacaccag cgacagcacc   360
gtgttccccg cgccgtggc caagggcgtg cacaccgtga agaaccccga gaacttcaag    420
gtgcccctgg acgtgatctt caagtgcaac agcgtgctga cctacaacct gacccccgtg    480
gtgcagaagt actggggcat ccacctgcag gccttcgtgc agaacggcac cgtgagcaag    540
aacgagcagg tgtgcgagga ggaccagacc cccaccaccg tggccccccat catccacacc    600
```

-continued

| | |
|---|---|
| accgccccca gcaccaccac caccctgacc cccaccagca cccccacccc caccccacc | 660 |
| cccaccccca ccgtgggcaa ctacagcatc aggaacggca acaccacctg cctgctggcc | 720 |
| accatgggcc tgcagctgaa catcaccgag gagaaggtgc ccttcatctt caacatcaac | 780 |
| cccgccacca ccaacttcac cggcagctgc cagcccaga gcgcccagct gaggctgaac | 840 |
| aacagccaga tcaagtacct ggacttcatc ttcgccgtga agaacgagaa gaggttctac | 900 |
| ctgaaggagg tgaacgtgta catgtacctg gccaacggca gcgccttcaa catcagcaac | 960 |
| aagaacctga gcttctggga cgcccccctg ggcagcagct acatgtgcaa caaggagcag | 1020 |
| gtgctgagcg tgagcagggc cttccagatc aacaccttca acctgaaggt gcagcccttc | 1080 |
| aacgtgacca agggccagta cagcaccgcc caggagtgca gcctggacga cgacaccatc | 1140 |
| ctgatcccca tcatcgtggg cgccggcctg agcggcctga tcatcgtgat cgtgatcgcc | 1200 |
| tacctgatcg gcaggaggaa gacctacgcc ggctaccaga ccctg | 1245 |

<210> SEQ ID NO 7
<211> LENGTH: 1251
<212> TYPE: DNA
<213> ORGANISM: Homo sapiens

<400> SEQUENCE: 7

| | |
|---|---|
| atggccgccc ccggcagcgc caggaggccc ctgctgctgc tgctgctgct gctgctgctg | 60 |
| ggcctgatgc actgcgccag cgccgccatg ttcatggtga agaacggcaa cggcaccgcc | 120 |
| tgcatcatgg ccaacttcag cgccgccttc agcgtgaact acgacaccaa gagcggcccc | 180 |
| aagaacatga ccttcgacct gcccagcgac gccaccgtgg tgctgaacag gagcagctgc | 240 |
| ggcaaggaga caccagcga ccccagcctg gtgatcgcct tcggcagggg ccacaccctg | 300 |
| accctgaact tcaccaggaa cgccaccagg tacagcgtgc agctgatgag cttcgtgtac | 360 |
| aacctgagcg acacccacct gttccccaac gccagcagca aggagatcaa gaccgtggag | 420 |
| agcatcaccg acatcagggc cgacatcgac aagaagtaca ggtgcgtgag cggcacccag | 480 |
| gtgcacatga caacgtgac cgtgaccctg cacgacgcca ccatccaggc ctacctgagc | 540 |
| aacagcagct tcagcagggg cgagaccagg tgcgagcagg acaggcccag ccccaccacc | 600 |
| gcccccccg ccccccccag ccccagcccc agcccgtgc ccaagagccc cagcgtggac | 660 |
| aagtacaacg tgagcggcac caacggcacc tgcctgctgg ccagcatggg cctgcagctg | 720 |
| aacctgacct acgagaggaa ggacaacacc accgtgacca ggctgctgaa catcaacccc | 780 |
| aacaagacca gcgccagcgg cagctgcggc gcccacctgg tgaccctgga gctgcacagc | 840 |
| gagggcacca ccgtgctgct gttccagttc ggcatgaacg ccagcagcag caggttcttc | 900 |
| ctgcagggca tccagctgaa caccatcctg cccgacgcca gggaccccgc cttcaaggcc | 960 |
| gccaacggca gcctgagggc cctgcaggcc accgtgggca acagctacaa gtgcaacgcc | 1020 |
| gaggagcacg tgagggtgac caaggccttc agcgtgaaca tcttcaaggt gtgggtgcag | 1080 |
| gccttcaagg tggagggcgg ccagttcggc agcgtggagg agtgcctgct ggacgagaac | 1140 |
| agcatgctga tccccatcgc cgtgggcggc gccctggccg gctggtgct gatcgtgctg | 1200 |
| atcgcctacc tggtgggcag gaagaggagc cacgccggct accagaccat c | 1251 |

<210> SEQ ID NO 8
<211> LENGTH: 1218
<212> TYPE: DNA
<213> ORGANISM: Mus musculus

<400> SEQUENCE: 8

```
atggccgccc ccggcgccag gaggcccctg ctgctgctgc tgctggccgg cctggcccac      60
ggcgccagcg ccctgttcga ggtgaagaac aacggcacca cctgcatcat ggccagcttc     120
agcgccagct tcctgaccac ctacgagacc gccaacggca ccagatcgt gaacatcagc      180
ctgcccgcca gcgccgaggt gctgaagaac ggcagcagct gcggcaagga gaacgtgagc     240
gaccccagcc tgaccatcac cttcggcagg ggctacctgc tgaccctgaa cttcaccaag     300
aacaccacca ggtacagcgt gcagcacatg tacttcacct acaacctgag cgacaccgag     360
cacttcccca cgccatcag caaggagatc tacaccatgg acagcaccac cgacatcaag     420
gccgacatca acaaggccta caggtgcgtg agcgacatca gggtgtacat gaagaacgtg     480
accgtggtgc tgagggacgc caccatccag gcctacctga gcagcggcaa cttcagcaag     540
gaggagaccc actgcaccca ggacggcccc agccccacca ccggcccccc cagccccagc     600
cccccctgg tgcccaccaa ccccaccgtg agcaagtaca acgtgaccgg caacaacggc      660
acctgcctgc tggccagcat ggccctgcag ctgaacatca cctacctgaa gaggacaac      720
aagaccgtga ccagggcctt caacatcagc ccaacgaca ccagcagcgg cagctgcggc      780
atcaacctgt gaccctgaa ggtggagaac aagaacaggg ccctggagct gcagttcggc      840
atgaacgcca gcagcagcct gttcttcctg cagggcgtga ggctgaacat gaccctgccc     900
gacgccctgg tgcccacctt cagcatcagc aaccacagcc tgaaggccct gcaggccacc     960
gtgggcaaca gctacaagtg caacaccgag gagcacatct tcgtgagcaa gatgctgagc    1020
ctgaacgtgt tcagcgtgca ggtgcaggcc ttcaaggtgg acagcgacag gttcggcagc    1080
gtggaggagt gcgtgcagga cggcaacaac atgctgatcc ccatcgccgt gggcggcgcc    1140
ctggccggcc tggtgctgat cgtgctgatc gcctacctga tcggcaggaa gaggagccac    1200
gccggctacc agaccatc                                                  1218
```

<210> SEQ ID NO 9
<211> LENGTH: 1434
<212> TYPE: DNA
<213> ORGANISM: Homo sapiens

<400> SEQUENCE: 9

```
atgggcaggt gctgcttcta caccgccggc accctgagcc tgctgctgct ggtgaccagc      60
gtgaccctgc tggtggccag ggtgttccag aaggccgtgg accagagcat cgagaagaag     120
atcgtgctga ggaacggcac cgaggccttc gacagctggg agaagccccc cctgcccgtg     180
tacacccagt tctacttctt caacgtgacc aaccccgagg agatcctgag gggcgagacc     240
cccagggtgg aggaggtggg ccctacacc tacaggagc tgaggaacaa ggccaacatc      300
cagttcggcg acaacggcac caccatcagc gccgtgagca caaggccta cgtgttcgag     360
agggaccaga gcgtgggcga ccccaagatc gacctgatca ggaccctgaa catccccgtg     420
ctgaccgtga tcgagtggag ccaggtgcac ttcctgaggg agatcatcga ggccatgctg     480
aaggcctacc agcagaagct gttcgtgacc cacaccgtgg acgagctgct gtggggctac     540
aaggacgaga tcctgagcct gatccacgtg ttcaggcccg acatcagccc ctacttcggc     600
ctgttctacg agaagaacgg caccaacgac ggcgactacg tgttcctgac cggcgaggac     660
agctacctga acttcaccaa gatcgtggag tggaacggca agaccagcct ggactggtgg     720
atcaccgaca agtgcaacat gatcaacggc accgacggcg acagcttcca ccccctgatc    780
accaaggacg aggtgctgta cgtgttcccc agcgacttct gcaggagcgt gtacatcacc    840
```

| | |
|---|---|
| ttcagcgact acgagagcgt gcagggcctg cccgccttca ggtacaaggt gcccgccgag | 900 |
| atcctggcca acaccagcga caacgccggc ttctgcatcc ccgagggcaa ctgcctgggc | 960 |
| agcggcgtgc tgaacgtgag catctgcaag aacggcgccc ccatcatcat gagcttcccc | 1020 |
| cacttctacc aggccgacga gaggttcgtg agcgccatcg agggcatgca ccccaaccag | 1080 |
| gaggaccacg agaccttcgt ggacatcaac cccctgaccg gcatcatcct gaaggccgcc | 1140 |
| aagaggttcc agatcaacat ctacgtgaag aagctggacg acttcgtgga gaccggcgac | 1200 |
| atcaggacca tggtgttccc cgtgatgtac ctgaacgaga gcgtgcacat cgacaaggag | 1260 |
| accgccagca ggctgaagag catgatcaac accaccctga tcatcaccaa catcccctac | 1320 |
| atcatcatgg ccctgggcgt gttcttcggc ctggtgttca cctggctggc ctgcaagggc | 1380 |
| cagggcagca tggacgaggg caccgccgac gagagggccc ccctgatcag gacc | 1434 |

<210> SEQ ID NO 10
<211> LENGTH: 1434
<212> TYPE: DNA
<213> ORGANISM: Mus musculus

<400> SEQUENCE: 10

| | |
|---|---|
| atgggcaggt gctgcttcta caccgccggc accctgagcc tgctgctgct ggtgaccagc | 60 |
| gtgaccctgc tggtggccag ggtgttccag aaggccgtgg accagaccat cgagaagaac | 120 |
| atggtgctgc agaacggcac caaggtgttc aacagctggg agaagccccc cctgccgtg | 180 |
| tacatccagt tctacttctt caacgtgacc aaccccgagg agatcctgca gggcgagatc | 240 |
| cccctgctgg aggaggtggg cccctacacc tacgggagc tgaggaacaa ggccaacatc | 300 |
| cagttcggcg agaacggcac caccatcagc gccgtgacca caaggcccta cgtgttcgag | 360 |
| aggaaccaga gcgtgggcga ccccaacgtg gacctgatca ggaccatcaa catccccctg | 420 |
| ctgaccgtgg tggacctggc ccagctgacc ctgctgaggg agctgatcga ggccatgctg | 480 |
| aaggcctacc agcagaagct gttcgtgatc cacaccgtgc acgagctgct gtggggctac | 540 |
| aaggacgaga tcctgagcct ggtgcacatc ttcaagcccg acgtgagccc caacttcggc | 600 |
| ctgttctacg agaggaacgg caccaacgac ggcgagtacg tgttcctgac cggcgaggac | 660 |
| aactacctga acttcagcaa gatcgtggag tggaacggca agaccagcct ggactggtgg | 720 |
| accaccgaca cctgcaacat gatcaacggc accgacggcg acagcttcca ccccctgatc | 780 |
| agcaaggacg aggtgctgta cctgttcccc agcgacctgt gcaggagcgt gcacatcacc | 840 |
| ttcagcagct cgagaacgt ggagggcctg cccgccttca ggtacaaggt gcccgccgag | 900 |
| atcctggcca acaccagcga gaacgccggc ttctgcatcc ccgagggcaa ctgcatggac | 960 |
| agcggcgtgc tgaacatcag catctgcaag aacggcgccc ccatcatcat gagcttcccc | 1020 |
| cacttctacc aggccgacga gaagttcgtg agcgccatca gggcatgca ccccaacaag | 1080 |
| gaggagcacg agagcttcgt ggacatcaac cccctgaccg gcatcatcct gaggggcgcc | 1140 |
| aagaggttcc agatcaacac ctacgtgagg aagctggacg acttcgtgga gaccggcgac | 1200 |
| atcaggacca tggtgttccc cgtgatgtac ctgaacgaga gcgtgctgat cgacaaggag | 1260 |
| accgccaacc agctgaagag cgtgatcaac accaccctgg tggtgaccaa catcccctac | 1320 |
| atcatcatgg ccctgggcgt gttcttcggc ctggtgttca cctggctggc ctgcaggggc | 1380 |
| cagggcagca tggacgaggg caccgccgac gagagggccc ccctgatcag gacc | 1434 |

<210> SEQ ID NO 11

```
<211> LENGTH: 867
<212> TYPE: DNA
<213> ORGANISM: Homo sapiens

<400> SEQUENCE: 11
atgaaggaca ggctggagca gctgaaggcc aagcagctga cccaggacga cgacaccgac    60
gaggtggaga tcgccatcga caacaccgcc ttcatggacg agttcttcag cgagatcgag   120
gagaccaggc tgaacatcga caagatcagc gagcacgtgg aggaggccaa gaagctgtac   180
agcatcatcc tgagcgcccc catccccgag cccaagacca aggacgacct ggagcagctg   240
accaccgaga tcaagaagag ggccaacaac gtgaggaaca agctgaagag catggagaag   300
cacatcgagg aggacgaggt gaggagcagc gccgacctga ggatcaggaa gagccagcac   360
agcgtgctga gcaggaagtt cgtggaggtg atgaccaagt acaacgaggc ccaggtggac   420
ttcagggaga ggagcaaggg caggatccag aggcagctgg agatcaccgg caagaagacc   480
accgacgagg agctggagga gatgctggag agcggcaacc ccgccatctt caccagcggc   540
atcatcgaca gccagatcag caagcaggcc ctgagcgaga tcgagggcag gcacaaggac   600
atcgtgaggc tggagagcag catcaaggag ctgcacgaca tgttcatgga catcgccatg   660
ctggtggaga ccagggcga gatgctggac aacatcgagc tgaacgtgat gcacaccgtg   720
gaccacgtgg agaaggccag ggacgagacc aagagggcca tgaagtacca gggccaggcc   780
aggaagaagc tgatcatcat catcgtggtg gtggtggtgc tgctgggcat cctggccctg   840
atcatcggcc tgagcgtggg cctgaag                                        867

<210> SEQ ID NO 12
<211> LENGTH: 1284
<212> TYPE: DNA
<213> ORGANISM: Mus musculus

<400> SEQUENCE: 12
atgttcttca cctgcggccc caacgaggcc atggtggtga gcggcttctg caggagcccc    60
cccgtgatgg tggccggcgg cagggtgttc gtgctgccct gcatccagca gatccagagg   120
atcagcctga caccctgac cctgaacgtg aagagcgaga aggtgtacac caggcacggc   180
gtgcccatca gcgtgaccgg catcgcccag gtgaagatcc agggccagaa caaggagatg   240
ctggccgccg cctgccagat gttcctgggc aagaccgagg ccgagatcgc ccacatcgcc   300
ctggagaccc tggagggcca ccagagggcc atcatggccc acatgaccgt ggaggagatc   360
tacaaggaca ggcagaagtt cagcgagcag gtgttcaagg tggccagcag cgacctggtg   420
aacatgggca tcagcgtggt gagctacacc ctgaaggaca tccacgacga ccaggactac   480
ctgcacagcc tgggcaaggc caggaccgcc caggtgcaga aggacgccag gatcggcgag   540
gccgaggcca gagggacgc cggcatcagg gaggccaagg ccaagcagga aaggtgagc   600
gcccagtgcc tgagcgagat cgagatggcc aaggcccaga gggactacga gctgaagaag   660
gccacctacg acatcgaggt gaacaccagg agggcccagg ccgacctggc ctaccagctg   720
caggtggcca agaccaagca gcagatcgag gagcagaggg tgcaggtgca ggtggtggag   780
agggcccagc aggtggccgt gcaggagcag agatcgcca ggaggagaa ggagctggag   840
gccagggtga ggaagcccgc cgaggccgag aggtacaggc tggagaggct ggccgaggcc   900
gagaaggccc agctgatcat gcaggccgag gccgaggccg agagcgtgag gatgaggggc   960
gaggccgagg ccttcgccat cggcgccagg gccagggccg aggccgagca gatggccaag  1020
aaggccgagg ccttccagat gtaccaggag gccgcccagc tggacatgct gctggagaag  1080
```
ctgccccagg tggccgagga gatcagcggc cccctgacca gcgccaacaa gatcaccctg 1140
gtgagcagcg gcagcggcac catgggcgcc gccaaggtga ccggcgaggt gctggacatc 1200
ctgagcaggc tgcccgagag cgtggagagg ctgaccggcg tgagcatcag ccaggtgaac 1260
cacaacaagc ccctgaggac cgcc 1284

<210> SEQ ID NO 13
<211> LENGTH: 1572
<212> TYPE: DNA
<213> ORGANISM: Rabies virus glycoprotein

<400> SEQUENCE: 13
atggtgcccc aggtgctgct gttcgtgctg ctgctgggct tcagcctgtg cttcggcaag 60
ttccccatct acaccatccc cgacaagctg ggcccctgga gccccatcga catccaccac 120
ctgaggtgcc ccaacaacct ggtggtggag gacgagggct gcaccaacct gagcggcttc 180
agctacatgg agctgaaggt gggctacatc agcgccatca aggtgaacgg cttcacctgc 240
accggcgtgg tgaccgaggc cgagacctac accaacttcg tgggctacgt gaccaccacc 300
ttcaagagga agcacttcag gcccaccccc gacgcctgca gggccgccta caactggaag 360
atggccggcg accccaggta cgaggagagc ctgcagaacc cctaccccga ctaccactgg 420
ctgaggaccg tgaggaccac caaggagagc ctgatcatca tcagccccag cgtgaccgac 480
ctggacccct acgacaagag cctgcacagc agggtgttcc ccggcggcaa gtgcagcggc 540
atcaccgtga gcagcaccta ctgcagcacc aaccacgact acaccatctg gatgcccgag 600
aaccccaggc ccggcacccc ctgcgacatc ttcaccaaca gcaggggcaa gagggccagc 660
aacggcaaca agacctgcgg cttcgtggac gagaggggcc tgtacaagag cctgaagggc 720
gcctgcaggc tgaagctgtg cggcgtgctg ggcctgaggc tgatggacgg cacctgggtg 780
gccatgcaga ccagcgacga gaccaagtgg tgcagccccg accagctggt gaacctgcac 840
gacttcagga gcgacgagat cgagcacctg gtggtggagg agctggtgaa gaagagggag 900
gagtgcctgg acaccctgga gagcatcatg accaccaaga gcgtgagctt caggaggctg 960
agccacctga ggaagctggt gcccggcttc ggcaaggcct acaccatctt caacaagacc 1020
ctgatggagg ccgacgccca ctacaagagc gtgaggacct ggaacgagat catccccagc 1080
aagggctgcc tgaaggtggg cggcaggtgc cacccccacg tgaacggcgt gttcttcaac 1140
ggcatcatcc tgggccccga cgacagggtg ctgatccccg agatgcagag cagcctgctg 1200
aggcagcaca tggagctgct ggagagcagc gtgatccccc tgatgcaccc cctggccgac 1260
cccagcaccg tgttcaagga gggcgacgag gccgaggact tcgtggaggt gcacctgccc 1320
gacgtgtaca agcagatcag cggcgtggac ctgggcctgc ccaactgggg caagtacgtg 1380
ctgatgaccg ccggcgccat gatcggcctg gtgctgatct tcagcctgat gacctggtgc 1440
aggagggcca acaggcccga gagcaagcag aggagcttcg gcggcaccgg cggcaacgtg 1500
agcgtgacca gccagagcgg caaggtgatc cccagctggg agagctacaa gagcggcggc 1560
gagatcaggc tg 1572

<210> SEQ ID NO 14
<211> LENGTH: 129
<212> TYPE: DNA
<213> ORGANISM: Artificial Sequence
<220> FEATURE:
<223> OTHER INFORMATION: Synthetic construct

<400> SEQUENCE: 14

```
ggctggaccc tgaacagcgc cggctacctg ctgggcaaga tcaacctgaa ggccctggcc    60
gccctggcca agaagatcct gggcggcggc ggcacccaca ggccccccat gtggagcccc   120
gtgtggccc                                                            129
```

<210> SEQ ID NO 15
<211> LENGTH: 438
<212> TYPE: DNA
<213> ORGANISM: Saccharomyces cerevisiae

<400> SEQUENCE: 15

```
aagctactgt cttctatcga caagcatgc gatatttgcc gacttaaaaa gctcaagtgc     60
tccaaagaaa aaccgaagtg cgccaagtgt ctgaagaaca actgggagtg tcgctactct   120
cccaaaacca aaggtctcc gctgactagg gcacatctga cagaagtgga atcaaggcta   180
gaaagactgg aacagctatt tctactgatt tttcctcgag aagaccttga catgattttg   240
aaaatggatt ctttacagga tataaaagca ttgttaacag gattatttgt acaagataat   300
gtgaataaag atgccgtcac agatagattg gcttcagtgg agactgatat gcctctaaca   360
ttgagacagc atagaataag tgcgacatca tcatcggaag agagtagtaa caaaggtcaa   420
agacagttga ctgtatcg                                                  438
```

<210> SEQ ID NO 16
<211> LENGTH: 2301
<212> TYPE: DNA
<213> ORGANISM: Artificial Sequence
<220> FEATURE:
<223> OTHER INFORMATION: Synthetic construct

<400> SEQUENCE: 16

```
atggtggact tgaggacact cggttattcg caacagcaac aggagaaaat caagcctaag     60
gtcaggagca ccgtcgcgca acaccacgag gcgcttgtgg ggcatggctt cactcatgcg   120
catattgtcg cgcttcaca gcaccctgcg gcgcttggga cggtggctgt caaataccaa   180
gatatgattg cggccctgcc cgaagccacg cacgaggcaa ttgtaggggt cggtaaacag   240
tggtcgggag cgcgagcact tgaggcgctg ctgactgtgg cgggtgagct taggggcct   300
ccgctccagc tcgacaccgg gcagctgctg aagatcgcga agagagggg agtaacagcg   360
gtagaggcag tgcacgcctg gcgcaatgcg ctcaccgggg cccccttgaa cctgacccca   420
gaccaggtag tcgcaatcgc gtcacatgac ggggaaaagc aagccctgga aaccgtgcaa   480
aggttgttgc cggtcctttg tcaagaccac ggccttacac cggagcaagt cgtggccatt   540
gcaaataata acggtggcaa acaggctctt gagacggttc agagacttct cccagttctc   600
tgtcaagccc acgggctgac tccgatcaa gttgtagcga ttgcgtcgca tgacggaggg   660
aaacaagcat tggagactgt ccaacggctc cttcccgtgt tgtgtcaagc ccacggtttg   720
acgcctgcac aagtggtcgc catcgcctcg aatggcggcg gtaagcaggc gctgaaaaca   780
gtacagcgcc tgctgcctgt actgtgccag gatcatggac tgaccccaga ccaggtagtc   840
gcaatcgcgt cacatgacgg gggaaagcaa gccctggaaa ccgtgcaaag gttgttgccg   900
gtccttttgtc aagaccacgg ccttacaccg gagcaagtcg tggccattgc aaataataac   960
ggtggcaaac aggctcttga gacggttcag agacttctcc cagttctctg tcaagcccac  1020
gggctgactc ccgatcaagt tgtagcgatt gcgtcgaaca ttggagggaa caagcattg   1080
gagactgtcc aacggctcct tcccgtgttg tgtcaagccc acggtttgac gcctgcacaa  1140
```

```
gtggtcgcca tcgccagcca tgatggcggt aagcaggcgc tggaaacagt acagcgcctg    1200
ctgcctgtac tgtgccagga tcatggactg accccagacc aggtagtcgc aatcgcgaac    1260
aataatgggg gaaagcaagc cctggaaacc gtgcaaaggt tgttgccggt cctttgtcaa    1320
gaccacggcc ttacaccgga gcaagtcgtg gccattgcaa gcaatggggg tggcaaacag    1380
gctcttgaga cggttcagag acttctccca gttctctgtc aagcccacgg gctgactccc    1440
gatcaagttg tagcgattgc gtcgaacatt ggagggaaac aagcattgga gactgtccaa    1500
cggctccttc ccgtgttgtg tcaagcccac ggtttgacgc tgcacaagt ggtcgccatc     1560 gccagccatg atggcggtaa gcaggcgctg aaaacagtac agcgcctgct gcctgtactg    1620
tgccaggatc atggactgac cccagaccag gtagtcgcaa tcgcgaacaa taatggggga    1680
aagcaagccc tggaaaccgt gcaaaggttg ttgccggtcc tttgtcaaga ccacggcctt    1740
acaccggagc aagtcgtggc cattgcatcc cacgacggtg gcaaacaggc tcttgagacg    1800
gttcagagac ttctcccagt tctctgtcaa gcccacgggc tgactcccga tcaagttgta    1860
gcgattgcgt ccaacggtgg agggaaacaa gcattggaga ctgtccaacg gctccttccc    1920
gtgttgtgtc aagcccacgg tttgacgcct gcacaagtgg tcgccatcgc cagccatgat    1980
ggcggtaagc aggcgctgga aacagtacag cgcctgctgc ctgtactgtg ccaggatcat    2040
ggactgacac ccgaacaggt ggtcgccatt gctaataata acggaggacg gccagccttg    2100
gagtccatcg tagcccaatt gtccaggccc gatcccgcgt tggctgcgtt aacgaatgac    2160
catctggtgg cgttggcatg tcttggtgga cgacccgcgc tcgatgcagt caaaaagggt    2220
ctgcctcatg ctcccgcatt gatcaaaaga accaaccggc ggattcccga gagaacttcc    2280
catcgagtcg cgggatccta a                                              2301

<210> SEQ ID NO 17
<211> LENGTH: 17
<212> TYPE: DNA
<213> ORGANISM: Saccharomyces cerevisiae

<400> SEQUENCE: 17
cggaggactg tcctccg                                                     17

<210> SEQ ID NO 18
<211> LENGTH: 18
<212> TYPE: DNA
<213> ORGANISM: Artificial Sequence
<220> FEATURE:
<223> OTHER INFORMATION: Synthetic construct

<400> SEQUENCE: 18
tcgctcgacg tacgctcg                                                    18

<210> SEQ ID NO 19
<211> LENGTH: 1068
<212> TYPE: DNA
<213> ORGANISM: Homo sapiens

<400> SEQUENCE: 19
atgaccaaga gctacagcga gagcggcctg atgggcgagc cccagcccca gggccccccc      60
agctggaccg acgagtgcct gagcagccag gacgaggagc acgaggccga caagaaggag     120
gacgacctgg agaccatgaa cgccgaggag gacagcctga ggaacggcgg cgaggaggag     180
gacgaggacg aggacctgga ggaggaggag gaggaggagg aggaggacga cgaccagaag     240
```

| | |
|---|---:|
| cccaagagga ggggcccca agaagaagaag atgaccaagg ccaggctgga gaggttcaag | 300 |
| ctgaggagga tgaaggccaa cgccagggag aggaacagga tgcacggcct gaacgccgcc | 360 |
| ctggacaacc tgaggaaggt ggtgccctgc tacagcaaga cccagaagct gagcaagatc | 420 |
| gagaccctga ggctggccaa gaactacatc tgggccctga gcgagatcct gaggagcggc | 480 |
| aagagccccg acctggtgag cttcgtgcag accctgtgca agggcctgag ccagcccacc | 540 |
| accaacctgg tggccggctg cctgcagctg aaccccagga ccttcctgcc cgagcagaac | 600 |
| caggacatgc cccccacct gcccaccgcc agcgccagct tccccgtgca ccctacagc | 660 |
| taccagagcc ccggcctgcc cagcccccc tacggcacca tggacagcag ccacgtgttc | 720 |
| cacgtgaagc cccccccca cgcctacagc gccgccctgg agcccttctt cgagagcccc | 780 |
| ctgaccgact gcaccagccc cagcttcgac ggcccctga gcccccccct gagcatcaac | 840 |
| ggcaacttca gcttcaagca cgagcccagc gccgagttcg agaagaacta cgccttcacc | 900 |
| atgcactacc ccgccgccac cctggccggc gcccagagcc acggcagcat cttcagcggc | 960 |
| accgccgccc ccaggtgcga gatccccatc gacaacatca tgagcttcga cagccacagc | 1020 |
| caccacgaga gggtgatgag cgcccagctg aacgccatct tccacgac | 1068 |

<210> SEQ ID NO 20
<211> LENGTH: 1074
<212> TYPE: DNA
<213> ORGANISM: Mus musculus
<400> SEQUENCE: 20

| | |
|---|---:|
| atgaccaaat catacagcga gagcgggctg atgggcgagc tcagccccca aggtccccca | 60 |
| agctggacag atgagtgtct cagttctcag gacgaggaac acgaggcaga caagaaagag | 120 |
| gacgagcttg aagccatgaa tgcagaggag gactctctga aaacgggggg agaggaggag | 180 |
| gaggaagatg aggacctaga ggaagaggag gaagaagaag aggaggagga ggatcaaaag | 240 |
| cccaagagac gggtcccaa aaagaaaaag atgaccaagg cgcgcctaga acgttttaaa | 300 |
| ttaaggcgca tgaaggccaa cgcccgcgag cggaaccgca tgcacgggct gaacgcggcg | 360 |
| ctggacaacc tgcgcaaggt ggtaccttgc tactccaaga cccagaaact gtctaaaata | 420 |
| gagacactgc gcttggccaa gaactacatc tgggctctgt cagagatcct gcgctcaggc | 480 |
| aaaagccctg atctggtctc cttcgtacag acgctctgca aaggtttgtc ccagcccact | 540 |
| accaatttgg tcgccggctg cctacagctc aaccctcgga cttcttgcc tgagcagaac | 600 |
| ccggacatgc ccccgcatct gccaaccgcc agcgcttcct tcccggtgca tccctactcc | 660 |
| taccagtccc ctggactgcc cagcccgccc tacggcacca tggacagctc ccacgtcttc | 720 |
| cacgtcaagc cgccgccaca cgcctacagc gcagctctgg agcccttctt tgaaagcccc | 780 |
| ctaactgact gcaccagccc ttcctttgac ggacccctca gcccgccgct cagcatcaat | 840 |
| ggcaacttct ctttcaaaca cgaaccatcc gccgagtttg aaaaaaatta tgcctttacc | 900 |
| atgcactacc cagcagcgac gctggcaggg ccccaaagcc acggatcaat cttctcttcc | 960 |
| ggtgccgctg cccctcgctg cgagatcccc atagacaaca ttatgtcttt cgatagccat | 1020 |
| tcgcatcatg agcgagtcat gagtgcccag cttaatgcca tctttcacga ttag | 1074 |

<210> SEQ ID NO 21
<211> LENGTH: 951
<212> TYPE: DNA
<213> ORGANISM: Homo sapiens
<400> SEQUENCE: 21

```
atgtacaaca tgatggagac cgagctgaag cccccccggcc cccagcagac cagcggcggc      60
ggcggcggca acagcaccgc cgccgccgcc ggcggcaacc agaagaacag ccccgacagg     120
gtgaagaggc ccatgaacgc cttcatggtg tggagcaggg gccagaggag gaagatggcc     180
caggagaacc ccaagatgca caacagcgag atcagcaaga ggctgggcgc cgagtggaag     240
ctgctgagcg agaccgagaa gaggcccttc atcgacgagg ccaagaggct gagggccctg     300
cacatgaagg agcaccccga ctacaagtac aggcccagga ggaagaccaa gaccctgatg     360
aagaaggaca agtacaccct gcccggcggc ctgctggccc ccggcggcaa cagcatggcc     420
agcggcgtgg gcgtgggcgc cggcctgggc gccggcgtga accagaggat ggacagctac     480
gcccacatga acggctggag caacggcagc tacagcatga tgcaggacca gctgggctac     540
ccccagcacc ccgcctgaa cgccacggc gccgccaga tgcagcccat gcacaggtac     600
gacgtgagcg ccctgcagta caacagcatg accagcagcc agacctacat gaacggcagc     660
cccacctaca gcatgagcta cagccagcag ggcacccccg gcatggccct gggcagcatg     720
ggcagcgtgg tgaagagcga ggccagcagc agcccccccg tggtgaccag cagcagccac     780
agcagggccc cctgccaggc cggcgacctg agggacatga tcagcatgta cctgcccggc     840
gccgaggtgc ccgagcccgc cgccccccagc aggctgcaca tgagccagca ctaccagagc     900
ggccccgtgc ccggcaccgc catcaacggc accctgcccc tgagccacat g              951

<210> SEQ ID NO 22
<211> LENGTH: 957
<212> TYPE: DNA
<213> ORGANISM: Mus musculus

<400> SEQUENCE: 22
atgtacaaca tgatggagac cgagctgaag cccccccggcc cccagcaggc cagcggcggc      60
ggcggcggcg gcggcaacgc caccgccgcc gccaccggcg gcaaccagaa gaacagcccc     120
gacagggtga agaggcccat gaacgccttc atggtgtgga gcggggccag aggaggaag     180
atggcccagg agaaccccaa gatgcacaac agcgagatca gcaagaggct gggcgccgag     240
tggaagctgc tgagcgagac cgagaagagg cccttcatcg acgaggccaa gaggctgagg     300
gccctgcaca tgaaggagca ccccgactac aagtacaggc caggaggaa gaccaagacc     360
ctgatgaaga aggacaagta caccctgccc ggcggcctgc tggccccgg cggcaacagc     420
atggccagcg gcgtgggcgt gggcgccggc ctgggcggcg cctgaacca gaggatggac     480
agctacgccc acatgaacgg ctggagcaac ggcagctaca gcatgatgca ggagcagctg     540
ggctacccccc agcaccccgg cctgaacgcc cacggcgccg cccagatgca gcccatgcac     600
aggtacgtgt gagcgccct gcagtacaac agcatgacca gcagcagac ctacatgaac     660
ggcagcccca cctacagcat gagctacagc cagcagggca ccccggcat ggccctgggc     720
agcatgggca gcgtggtgaa gagcgaggcc agcagcagcc ccccgtggt gaccagcagc     780
agccacagca gggcccctg ccaggccggc gacctgaggg acatgatcag catgtacctg     840
cccggcgccg aggtgcccga gcccgccgcc ccagcaggc tgcacatggc ccagcactac     900
cagagcggcc ccgtgcccgg caccgccaag tacggcaccc tgcccctgag ccacatg        957

<210> SEQ ID NO 23
<211> LENGTH: 717
<212> TYPE: DNA
<213> ORGANISM: Aequorea victoria
```

<400> SEQUENCE: 23

```
atggtgagca agggcgagga gctgttcacc ggcgtggtgc ccatcctggt ggagctggac    60
ggcgacgtga acggccacaa gttcagcgtg agcggcgagg gcgagggcga cgccacctac   120
ggcaagctga ccctgaagtt catctgcacc accggcaagc tgcccgtgcc ctggcccacc   180
ctggtgacca ccctgaccta cggcgtgcag tgcttcagca ggtaccccga ccacatgaag   240
cagcacgact tcttcaagag cgccatgccc gagggctacg tgcaggagag gaccatcttc   300
ttcaaggacg acggcaacta caagaccagg gccgaggtga agttcgaggg cgacaccctg   360
gtgaacagga tcgagctgaa gggcatcgac ttcaaggagg acggcaacat cctgggccac   420
aagctggagt acaactacaa cagccacaac gtgtacatca tggccgacaa gcagaagaac   480
ggcatcaagg tgaacttcaa gatcaggcac aacatcgagg acggcagcgt gcagctggcc   540
gaccactacc agcagaacac ccccatcggc gacggccccg tgctgctgcc cgacaaccac   600
tacctgagca cccagagcgc cctgagcaag gaccccaacg agaagaggga ccacatggtg   660
ctgctggagt tcgtgaccgc cgccgggatc accctgggca tggacgagct gtacaag      717
```

<210> SEQ ID NO 24
<211> LENGTH: 486
<212> TYPE: DNA
<213> ORGANISM: Synechocystis sp PCC6803

<400> SEQUENCE: 24

```
tgccccggct gcctgagctt cggcaccgag atcctgaccg tggagtacgg cccctgccc    60
atcggcaaga tcgtgagcga ggagatcaac tgcagcgtgt acagcgtgga ccccgagggc   120
agggtgtaca cccaggccat cgcccagtgg cacgacaggg gcgagcagga ggtgctggag   180
tacgagctgg aggacggcag cgtgatcagg gccaccagcg accacaggtt cctgaccacc   240
gactaccagc tgctggccat cgaggagatc ttcgccaggc agctggacct gctgaccctg   300
gagaacatca gcagaccga ggaggccctg gacaaccaca ggctgccctt ccccctgctg   360
gacgccggca ccatcaagat ggtgaaggtg atcggcagga ggagcctggg cgtgcagagg   420
atcttcgaca tcggcctgcc ccaggaccac aacttcctgc tggccaacgg cgccatcgcc   480
gccgcc                                                              486
```

<210> SEQ ID NO 25
<211> LENGTH: 411
<212> TYPE: DNA
<213> ORGANISM: Nostoc punctiforme

<400> SEQUENCE: 25

```
tgccccggct gcctgagcta cgagaccgag atcctgaccg tggagtacgg cctgctgccc    60
atcggcaaga tcgtggagaa gaggatcgag tgcaccgtgt acagcgtgga caacaacggc   120
aacatctaca cccagcccgt ggcccagtgg cacgacaggg gcgagcagga ggtgttcgag   180
tactgcctgg aggacggcag cctgatcagg gccaccaagg accacaagtt catgaccgtg   240
gacggccaga tgctgcccat cgacgagatc ttcgagaggg agctggacct gatgagggtg   300
gacaacatca gatcgccac caggaagtac ctggcaagc agaacgtgta cgacatcggc   360
gtggagaggg accacaactt cgccctgaag aacggcttca tcgccagcgc c            411
```

<210> SEQ ID NO 26
<211> LENGTH: 480
<212> TYPE: DNA
<213> ORGANISM: Penicillium chrysogenum

<400> SEQUENCE: 26
tgccccggct gcctggccaa gggcaccagg ctgctgaggt gcgacggcac cgagatcaac 60
gtggaggacg tgagggaggg cgacctgctg ctgggccccg acggcgagcc caggagggcc 120
ttcaacatcg tgaacggcat cgacaggctg tacaggatca agatcggcgg cgagaaggag 180
gacctggtgg tgacccccaa ccacatcctg gtgctgtaca gggaggacgg cagcaagaac 240
gtggagaagc agaccgtgga gatcaccgcc gccgagttcg ccgccctgag caccgaggag 300
aggagcctgt acagcgcctt caccagcccc agggccgaga agggcgccga cgacagcgcc 360
cagacccaca gcttcaagat cgagcaggtg agcctggaga gcgagaagac cgagtgggcc 420
ggcttcaggg tggacaagga ccagctgtac ctgaggcacg actacctggt gctgcacgcc 480

<210> SEQ ID NO 27
<211> LENGTH: 96
<212> TYPE: DNA
<213> ORGANISM: Artificial Sequence
<220> FEATURE:
<223> OTHER INFORMATION: Synthetic construct

<400> SEQUENCE: 27
aggaagagga agaggagggg cggcggcagc ggcggcagcg gcggcagcgg cggcagcggc 60
ggcagcggcg gcagcggcag gagcaggaag aggagg 96

<210> SEQ ID NO 28
<211> LENGTH: 21
<212> TYPE: DNA
<213> ORGANISM: Artificial Sequence
<220> FEATURE:
<223> OTHER INFORMATION: Synthetic construct

<400> SEQUENCE: 28
cccaagaaga agaggaaggt g 21

<210> SEQ ID NO 29
<211> LENGTH: 2630
<212> TYPE: DNA
<213> ORGANISM: Homo sapiens

<400> SEQUENCE: 29
gagctcccac ctccctctct gtgctgggac tcacagaggg agacctcagg aggcagtctg 60
tccatcacat gtccaaatgc agagcatacc ctgggctggg cgcagtggcg cacaactgta 120
attccagcac tttgggaggc tgatgtggaa ggatcacttg agcccagaag ttctagacca 180
gcctgggcaa catggcaaga ccctatctct acaaaaaaag ttaaaaaatc agccacgtgt 240
ggtgacacac acctgtagtc ccagctattc aggaggctga ggtgagggga tcacttaagg 300
ctgggaggtt gaggctgcag tgagtcgtgg ttgcgccact gcactccagc ctgggcaaca 360
gtgagaccct gtctcaaaag acaaaaaaaa aaaaaaaaaa aaaaagaaca tatcctggtg 420
tggagtaggg gacgctgctc tgacagaggc tcgggggcct gagctggctc tgtgagctgg 480
ggaggaggca gacagccagg ccttgtctgc aagcagacct ggcagcattg ggctggccgc 540
cccccagggc ctcctcttca tgcccagtga atgactcacc ttggcacaga cacaatgttc 600
ggggtgggca cagtgcctgc ttcccgccgc accccagccc ccctcaaatg ccttccgaga 660
agcccattga gcagggggct tgcattgcac cccagcctga cagcctggca tcttgggata 720
aaagcagcac agccccctag ggctgccct tgctgtgtgg cgccaccggc ggtggagaac 780

| | |
|---|---|
| aaggctctat tcagcctgtg cccaggaaag gggatcaggg gatgcccagg catggacagt | 840 |
| gggtggcagg ggggagagg agggctgtct gcttcccaga agtccaagga cacaaatggg | 900 |
| tgagggact gggcagggtt ctgaccctgt gggaccagag tggagggcgt agatggacct | 960 |
| gaagtctcca gggacaacag ggcccaggtc tcaggctcct agttgggccc agtggctcca | 1020 |
| gcgtttccaa acccatccat ccccagaggt tcttcccatc tctccaggct gatgtgtggg | 1080 |
| aactcgagga aataaatctc cagtgggaga cggaggggtg gccagggaaa cggggcgctg | 1140 |
| caggaataaa gacgagccag cacagccagc tcatgtgtaa cggctttgtg gagctgtcaa | 1200 |
| ggcctggtct ctgggagaga ggcacaggga ggccagacaa ggaaggggtg acctggaggg | 1260 |
| acagatccag gggctaaagt cctgataagg caagagagtg ccggccccct cttgccctat | 1320 |
| caggacctcc actgccacat agaggccatg attgacccctt agacaaaggg ctggtgtcca | 1380 |
| atcccagccc ccagccccag aactccaggg aatgaatggg cagagagcag gaatgtggga | 1440 |
| catctgtgtt caaggaagg actccaggag tctgctggga atgaggccta gtaggaaatg | 1500 |
| aggtggccct tgagggtaca gaacaggttc attcttcgcc aaattcccag caccttgcag | 1560 |
| gcacttacag ctgagtgaga taatgcctgg gttatgaaat caaaaagttg gaaagcaggt | 1620 |
| cagaggtcat ctggtacagc ccttccttcc ctttttttt tttttttttt gtgagacaag | 1680 |
| gtctctctct gttgcccagg ctggagtggc gcaaacacag ctcactgcag cctcaaccta | 1740 |
| ctgggctcaa gcaatcctcc agcctcagcc tcccaaagtg ctgggattac aagcatgagc | 1800 |
| caccccactc agccctttcc ttcctttta attgatgcat aataattgta agtattcatc | 1860 |
| atggtccaac caacccttc ttgacccacc ttcctagaga gagggtcctc ttgcttcagc | 1920 |
| ggtcagggcc ccagacccat ggtctggctc caggtaccac ctgcctcatg caggagttgg | 1980 |
| cgtgcccagg aagctctgcc tctgggcaca gtgacctcag tggggtgagg ggagctctcc | 2040 |
| ccatagctgg gctgcggccc aaccccaccc cctcaggcta tgccagggg tgttgccagg | 2100 |
| ggcacccggg catcgccagt ctagcccact ccttcataaa gccctcgcat cccaggagcg | 2160 |
| agcagagcca gagcaggatg gagaggagac gcatcacctc cgctgctcgc cgctcctacg | 2220 |
| tctcctcagg ggagatgatg gtgggggcc tggctcctgg ccgccgtctg ggtcctggca | 2280 |
| cccgcctctc cctggctcga atgccccctc cactcccgac ccgggtggat ttctccctgg | 2340 |
| ctggggcact caatgctggc ttcaaggaga cccgggccag tgagcgggca gagatgatgg | 2400 |
| agctcaatga ccgctttgcc agctacatcg agaaggttcg cttcctggaa cagcaaaaca | 2460 |
| aggcgctggc tgctgagctg aaccagctgc gggccaagga gcccaccaag ctggcagacg | 2520 |
| tctaccaggc tgagctgcga gagctgcggc tgcggctcga tcaactcacc gccaacagcg | 2580 |
| cccggctgga ggttgagagg gacaatctgg cacaggacct ggccactgtg | 2630 |

<210> SEQ ID NO 30
<211> LENGTH: 2353
<212> TYPE: DNA
<213> ORGANISM: Mus musculus

<400> SEQUENCE: 30

| | |
|---|---|
| catgtcgctg gtatggagta taggctgttg ctatgacagg aactcagggg tcttaactgg | 60 |
| cttgagcgct gggagggggc aagcagccag gccttgtctg taagctgaag acctggcagt | 120 |
| gctgagctgg tcacccccca ggacctcctt ttgtgcccaa cgagtgactc accttggcat | 180 |
| agacataatg gtcaggggtg ggcacgcagc ctgcttcccg ctgtgctcca ggcctccttc | 240 |
| gatgctttcc gagaagtcta ttgagctggg agcttgtact gcacccgggg ctgacatcct | 300 |

```
ggcatcctgg gataaaagca gcccacgggg ctgcccttgc catatgcctc actggcggca    360
gaggacaagg ctctattcag caagtgccct ggagtagaca ccagaagccc aagcatgggc    420
agaggaaggc aggggttggg gggagcagag ctgtctgtgt tccagaagcc caaggacaca    480
gatggctaag cgcctggga gggacctgag tggaagagat agatgggcct gaagtctcaa    540
gcagcaacag cctcctcccc gccattggtg agggtgggt ttggtttccc ggacctacat    600
atccctcaga ggcctggtgt gtaggaattt aaaggaggta aatctcctga gagaatgagg    660
ggtacccagg aagacggggt gttacagaaa gactccagca tgcacagcca actcactcaa    720
aactactctg tcaggggctg ccgggggcca ggctcgggt gggggtggg ggggcaaaga    780 gaagctggac cagggagaaa tggcccacta ggctggatat gaggccacag aggggctcag    840
gaatgaagcc tgctgtctta ccctattagg atctgcgtgc ataccttctg ctgtgcactc    900
taaacacaca gccagaggct caagttgacc ctggagtcac agagagggct ccaaccttag    960
ccctccactc ctgaactcca ggaatgaaa gatagagttg gagcgattca ggggagagga   1020
ctctgttgag aatgggggcc acaggaaact gtaatatagg ttgatcccgg aggaagggaa   1080
taggttcttc aagttcctag catctcacag gcccccagag aaggacagag ttggggtggt   1140
cctggcttac aggctctaag aactggaagc tgattacccc accaagctgt gcactctctg   1200
tctctgtctc tgtctctgtg tgtgcgcgct cgtgcacact tatcacacaa atgttcatgt   1260
gtgtgcacat agatgagttg agaccagagg tcaacctcag gcactgttgc cttggttttc   1320
tgagagagca tttctctctg gacctggaac tcgccaatta gtgagagcca ggaagtctgc   1380 tgatttcac tgcccagcac tggagtttac aagtatgcac tgtcaaccca ggccttttgt   1440
attcattctg cagctagaac ttgggtgggt cttcatgctt gacaggcaag caatttatgg   1500
actaagctgt ttcctcggcc ctctcttgac ccatttacca gaaggggggt tccttgatca   1560
atggcgaagc caggctggtg ttcccaagaa agccttgact ctgggtacag tgacctcagt   1620
ggggtgagag gagttctccc cttagctggg ctggggccca gcttcacccc ctcaggctat   1680
tcagtggggg tgcttccagg aagtcagggg cagatttagt ccaacccgtt cctccataaa   1740
ggccctgaca tcccaggagc cagcagaggc agggcaggat ggagcggaga cgcatcacct   1800
ctgcgcgccg ctcctatgcc tccgagacgg tggtcagggg cctcggtcct agtcgacaat   1860
tgggtaccat gccacgcttc tccctgtctc gaatgactcc tccactccct gccagggtgg   1920
acttctccct ggccggggcg ctcaatgctg gcttcaagga cacgggcg agcgagcgtg   1980 cagagatgat ggagctcaat gaccgctttg ctagctacat cgagaaggtc cgcttcctgg   2040
aacagcaaaa caaggcgctg gcagctgaac tgaaccagct tcgagccaag gagcccacca   2100
aactggctga tgtctaccag gcggagcttc gggagctgcg gctgcggctg accagctta   2160 cggccaacag tgcccggctg gaggtggaga gggacaacct tgcacaggac ctcggcaccc   2220
tgaggcagaa gtgagaaggg ggatagggga aatggctagt gagcagagag actgaagtgc   2280
aagggctgcc tgcctggaaa aaagggcact gcctcccca ggggagtctc tcagctcctg   2340
catttcccca tgt                                                       2353
```

<210> SEQ ID NO 31
<211> LENGTH: 688
<212> TYPE: DNA
<213> ORGANISM: Artificial Sequence
<220> FEATURE:
<223> OTHER INFORMATION: Synthetic construct

<400> SEQUENCE: 31

```
gatctaacat atcctggtgt ggagtagggg acgctgctct gacagaggct cgggggcctg      60
agctggctct gtgagctggg gaggaggcag acagccaggc cttgtctgca agcagacctg     120
gcagcattgg gctggccgcc ccccagggcc tcctcttcat gcccagtgaa tgactcacct     180
tggcacagac acaatgttcg gggtgggcac agtgcctgct tcccgccgca ccccagcccc     240
cctcaaatgc cttccgagaa gcccattgag caggggcttt gcattgcacc ccagcctgac     300
agcctggcat cttgggataa aagcagcaca gcccctagg ggctgccctt gctgtgtggc      360
gccaccggcg gtggagaaca aggctctatt cagcctgtgc ccaggaaagg ggatcagggg     420
atgcccaggc atggacagtg ggtggcaggg ggggagagga gggctgtctg cttcccagaa     480
gtccaaggac acaaatgggt gaggggagag ctctccccat agctgggctg cggcccaacc     540
ccacccccctc aggctatgcc aggggtgtt gccaggggca cccgggcatc gccagtctag     600
cccactcctt cataaagccc tcgcatccca ggagcgagca gagccagagc aggttggaga     660
ggagacgcat cacctccgct gctcgcaa                                        688
```

<210> SEQ ID NO 32
<211> LENGTH: 303
<212> TYPE: DNA
<213> ORGANISM: Escherichia coli

<400> SEQUENCE: 32

```
atgcagttta agtgtatac ctataaacgc gaaagccgct atcgcctgtt tgtggatgtg       60
cagagcgata ttattgatac cccgggccgc cgcatggtga ttccgctggc gagcgcgcgc     120
ctgctgagcg ataaagtgag ccgcgaactg tatccggtgg tgcatattgg cgatgaaagc     180
tggcgcatga tgaccaccga tatggcgagc gtgccggtga gcgtgattgg cgaagaagtg     240
gcggatctga gccatcgcga aaacgatatt aaaaacgcga ttaacctgat gttttgggggc     300
att                                                                   303
```

<210> SEQ ID NO 33
<211> LENGTH: 410
<212> TYPE: PRT
<213> ORGANISM: Homo sapiens

<400> SEQUENCE: 33

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
```

```
            130                 135                 140
Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

Ser Leu Asp Asp Asp Thr Ile Leu Ile Pro Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410

<210> SEQ ID NO 34
<211> LENGTH: 423
<212> TYPE: PRT
<213> ORGANISM: Mus musculus

<400> SEQUENCE: 34

Met Cys Leu Ser Pro Val Lys Gly Ala Lys Leu Ile Leu Ile Phe Leu
1               5                   10                  15

Phe Leu Gly Ala Val Gln Ser Asn Ala Leu Ile Val Asn Leu Thr Asp
            20                  25                  30

Ser Lys Gly Thr Cys Leu Tyr Ala Arg Gly Ser Gly Gly Ala Glu Trp
        35                  40                  45

Glu Met Asn Phe Thr Ile Thr Tyr Glu Thr Thr Asn Gln Thr Asn Lys
    50                  55                  60

Thr Ile Thr Ile Ala Val Pro Asp Lys Ala Thr His Asp Gly Ser Ser
65                  70                  75                  80

Cys Gly Asp Asp Arg Asn Ser Ala Lys Ile Met Ile Gln Phe Gly Phe
                85                  90                  95
```

-continued

```
Ala Val Ser Trp Ala Val Asn Phe Thr Lys Glu Ala Ser His Tyr Ser
             100                 105                 110
Ile His Asp Ile Val Leu Ser Tyr Asn Thr Ser Asp Ser Thr Val Phe
         115                 120                 125
Pro Gly Ala Val Ala Lys Gly Val His Thr Val Lys Asn Pro Glu Asn
     130                 135                 140
Phe Lys Val Pro Leu Asp Val Ile Phe Lys Cys Asn Ser Val Leu Thr
145                 150                 155                 160
Tyr Asn Leu Thr Pro Val Val Gln Lys Tyr Trp Gly Ile His Leu Gln
                 165                 170                 175
Ala Phe Val Gln Asn Gly Thr Val Ser Lys Asn Glu Gln Val Cys Glu
             180                 185                 190
Glu Asp Gln Thr Pro Thr Thr Val Ala Pro Ile Ile His Thr Thr Ala
         195                 200                 205
Pro Ser Thr Thr Thr Thr Leu Thr Pro Thr Ser Thr Pro Thr Pro Thr
     210                 215                 220
Pro Thr Pro Thr Pro Thr Val Gly Asn Tyr Ser Ile Arg Asn Gly Asn
225                 230                 235                 240
Thr Thr Cys Leu Leu Ala Thr Met Gly Leu Gln Leu Asn Ile Thr Glu
                 245                 250                 255
Glu Lys Val Pro Phe Ile Phe Asn Ile Asn Pro Ala Thr Thr Asn Phe
             260                 265                 270
Thr Gly Ser Cys Gln Pro Gln Ser Ala Gln Leu Arg Leu Asn Asn Ser
         275                 280                 285
Gln Ile Lys Tyr Leu Asp Phe Ile Phe Ala Val Lys Asn Glu Lys Arg
     290                 295                 300
Phe Tyr Leu Lys Glu Val Asn Val Tyr Met Tyr Leu Ala Asn Gly Ser
305                 310                 315                 320
Ala Phe Asn Ile Ser Asn Lys Asn Leu Ser Phe Trp Asp Ala Pro Leu
                 325                 330                 335
Gly Ser Ser Tyr Met Cys Asn Lys Glu Gln Val Leu Ser Val Ser Arg
             340                 345                 350
Ala Phe Gln Ile Asn Thr Phe Asn Leu Lys Val Gln Pro Phe Asn Val
         355                 360                 365
Thr Lys Gly Gln Tyr Ser Thr Ala Gln Glu Cys Ser Leu Asp Asp Asp
     370                 375                 380
Thr Ile Leu Ile Pro Ile Val Gly Ala Gly Leu Ser Gly Leu Ile Ile
385                 390                 395                 400
Ile Val Ile Val Ile Ala Tyr Leu Ile Gly Arg Arg Lys Thr Tyr Ala
                 405                 410                 415
Gly Tyr Gln Thr Leu Thr Arg
             420

<210> SEQ ID NO 35
<211> LENGTH: 410
<212> TYPE: PRT
<213> ORGANISM: Homo sapiens

<400> SEQUENCE: 35

Met Val Cys Phe Arg Leu Phe Pro Val Pro Gly Ser Gly Leu Val Leu
1               5                   10                  15
Val Cys Leu Val Leu Gly Ala Val Arg Ser Tyr Ala Leu Glu Leu Asn
             20                  25                  30
Leu Thr Asp Ser Glu Asn Ala Thr Cys Leu Tyr Ala Lys Trp Gln Met
         35                  40                  45
```

Asn Phe Thr Val Arg Tyr Glu Thr Thr Asn Lys Thr Tyr Lys Thr Val
 50                  55                  60

Thr Ile Ser Asp His Gly Thr Val Thr Tyr Asn Gly Ser Ile Cys Gly
 65                  70                  75                  80

Asp Asp Gln Asn Gly Pro Lys Ile Ala Val Gln Phe Gly Pro Gly Phe
                 85                  90                  95

Ser Trp Ile Ala Asn Phe Thr Lys Ala Ser Thr Tyr Ser Ile Asp
                100                 105                 110

Ser Val Ser Phe Ser Tyr Asn Thr Gly Asp Asn Thr Thr Phe Pro Asp
                115                 120                 125

Ala Glu Asp Lys Gly Ile Leu Thr Val Asp Glu Leu Leu Ala Ile Arg
                130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
                180                 185                 190

Lys Thr Ser Thr Val Ala Pro Thr Ile His Thr Thr Val Pro Ser Pro
                195                 200                 205

Thr Thr Thr Pro Thr Pro Lys Glu Lys Pro Glu Ala Gly Thr Tyr Ser
210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
                260                 265                 270

Arg Leu Asn Ser Ser Thr Ile Lys Tyr Leu Asp Phe Val Phe Ala Val
275                 280                 285

Lys Asn Glu Asn Arg Phe Tyr Leu Lys Glu Val Asn Ile Ser Met Tyr
290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
                340                 345                 350

Gln Pro Phe Asn Val Thr Gln Gly Lys Tyr Ser Thr Ala Gln Asp Cys
                355                 360                 365

Ser Ala Asp Asp Asp Asn Phe Leu Val Pro Ile Ala Val Gly Ala Ala
                370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410

<210> SEQ ID NO 36
<211> LENGTH: 415
<212> TYPE: PRT
<213> ORGANISM: Mus musculus

<400> SEQUENCE: 36

Met Cys Leu Ser Pro Val Lys Gly Ala Lys Leu Ile Leu Ile Phe Leu

```
               1               5                  10                 15
            Phe Leu Gly Ala Val Gln Ser Asn Ala Leu Ile Val Asn Leu Thr Asp
                            20                  25                 30

Ser Lys Gly Thr Cys Leu Tyr Ala Glu Trp Glu Met Asn Phe Thr Ile
                        35                  40                  45

Thr Tyr Glu Thr Thr Asn Gln Thr Asn Lys Thr Ile Thr Ile Ala Val
                    50                  55                  60

Pro Asp Lys Ala Thr His Asp Gly Ser Cys Gly Asp Asp Arg Asn
             65                  70                  75                  80

Ser Ala Lys Ile Met Ile Gln Phe Gly Phe Ala Val Ser Trp Ala Val
                                85                  90                  95

Asn Phe Thr Lys Glu Ala Ser His Tyr Ser Ile His Asp Ile Val Leu
                            100                 105                 110

Ser Tyr Asn Thr Ser Asp Ser Thr Val Phe Pro Gly Ala Val Ala Lys
                        115                 120                 125

Gly Val His Thr Val Lys Asn Pro Glu Asn Phe Lys Val Pro Leu Asp
                    130                 135                 140

Val Ile Phe Lys Cys Asn Ser Val Leu Thr Tyr Asn Leu Thr Pro Val
             145                 150                 155                 160

Val Gln Lys Tyr Trp Gly Ile His Leu Gln Ala Phe Val Gln Asn Gly
                                165                 170                 175

Thr Val Ser Lys Asn Glu Gln Val Cys Glu Glu Asp Gln Thr Pro Thr
                            180                 185                 190

Thr Val Ala Pro Ile Ile His Thr Thr Ala Pro Ser Thr Thr Thr Thr
                        195                 200                 205

Leu Thr Pro Thr Ser Thr Pro Thr Pro Thr Pro Thr Pro Thr Pro Thr
             210                 215                 220

Val Gly Asn Tyr Ser Ile Arg Asn Gly Asn Thr Thr Cys Leu Leu Ala
             225                 230                 235                 240

Thr Met Gly Leu Gln Leu Asn Ile Thr Glu Glu Lys Val Pro Phe Ile
                                245                 250                 255

Phe Asn Ile Asn Pro Ala Thr Thr Asn Phe Thr Gly Ser Cys Gln Pro
                            260                 265                 270

Gln Ser Ala Gln Leu Arg Leu Asn Asn Ser Gln Ile Lys Tyr Leu Asp
                        275                 280                 285

Phe Ile Phe Ala Val Lys Asn Glu Lys Arg Phe Tyr Leu Lys Glu Val
                    290                 295                 300

Asn Val Tyr Met Tyr Leu Ala Asn Gly Ser Ala Phe Asn Ile Ser Asn
             305                 310                 315                 320

Lys Asn Leu Ser Phe Trp Asp Ala Pro Leu Gly Ser Ser Tyr Met Cys
                                325                 330                 335

Asn Lys Glu Gln Val Leu Ser Val Ser Arg Ala Phe Gln Ile Asn Thr
                            340                 345                 350

Phe Asn Leu Lys Val Gln Pro Phe Asn Val Thr Lys Gly Gln Tyr Ser
                        355                 360                 365

Thr Ala Gln Asp Cys Ser Ala Asp Glu Asp Asn Phe Leu Val Pro Ile
                    370                 375                 380

Ala Val Gly Ala Ala Leu Gly Gly Val Leu Ile Leu Val Leu Leu Ala
             385                 390                 395                 400

Tyr Phe Ile Gly Leu Lys Arg His His Thr Gly Tyr Glu Gln Phe
                                405                 410                 415

<210> SEQ ID NO 37
```

```
<211> LENGTH: 411
<212> TYPE: PRT
<213> ORGANISM: Homo sapiens

<400> SEQUENCE: 37

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
50                  55                  60

Thr Ile Ser Asp His Gly Thr Val Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Glu Glu Cys
        355                 360                 365

Ser Ala Asp Ser Asp Leu Asn Phe Leu Ile Pro Val Ala Val Gly Val
    370                 375                 380

Ala Leu Gly Phe Leu Ile Ile Val Val Phe Ile Ser Tyr Met Ile Gly
```

```
              385                 390                 395                 400
Arg Arg Lys Ser Arg Thr Gly Tyr Gln Ser Val
                    405                 410

<210> SEQ ID NO 38
<211> LENGTH: 415
<212> TYPE: PRT
<213> ORGANISM: Mus musculus

<400> SEQUENCE: 38

Met Cys Leu Ser Pro Val Lys Gly Ala Lys Leu Ile Leu Ile Phe Leu
1               5                   10                  15

Phe Leu Gly Ala Val Gln Ser Asn Ala Leu Ile Val Asn Leu Thr Asp
                20                  25                  30

Ser Lys Gly Thr Cys Leu Tyr Ala Glu Trp Glu Met Asn Phe Thr Ile
            35                  40                  45

Thr Tyr Glu Thr Thr Asn Gln Thr Asn Lys Thr Ile Thr Ile Ala Val
        50                  55                  60

Pro Asp Lys Ala Thr His Asp Gly Ser Ser Cys Gly Asp Asp Arg Asn
65                  70                  75                  80

Ser Ala Lys Ile Met Ile Gln Phe Gly Phe Ala Val Ser Trp Ala Val
                85                  90                  95

Asn Phe Thr Lys Glu Ala Ser His Tyr Ser Ile His Asp Ile Val Leu
                100                 105                 110

Ser Tyr Asn Thr Ser Asp Ser Thr Val Phe Pro Gly Ala Val Ala Lys
            115                 120                 125

Gly Val His Thr Val Lys Asn Pro Glu Asn Phe Lys Val Pro Leu Asp
        130                 135                 140

Val Ile Phe Lys Cys Asn Ser Val Leu Thr Tyr Asn Leu Thr Pro Val
145                 150                 155                 160

Val Gln Lys Tyr Trp Gly Ile His Leu Gln Ala Phe Val Gln Asn Gly
                165                 170                 175

Thr Val Ser Lys Asn Glu Gln Val Cys Glu Glu Asp Gln Thr Pro Thr
                180                 185                 190

Thr Val Ala Pro Ile Ile His Thr Thr Ala Pro Ser Thr Thr Thr Thr
            195                 200                 205

Leu Thr Pro Thr Ser Thr Pro Thr Pro Thr Pro Thr Pro Thr Pro Thr
        210                 215                 220

Val Gly Asn Tyr Ser Ile Arg Asn Gly Asn Thr Thr Cys Leu Leu Ala
225                 230                 235                 240

Thr Met Gly Leu Gln Leu Asn Ile Thr Glu Glu Lys Val Pro Phe Ile
                245                 250                 255

Phe Asn Ile Asn Pro Ala Thr Thr Asn Phe Thr Gly Ser Cys Gln Pro
                260                 265                 270

Gln Ser Ala Gln Leu Arg Leu Asn Asn Ser Gln Ile Lys Tyr Leu Asp
            275                 280                 285

Phe Ile Phe Ala Val Lys Asn Glu Lys Arg Phe Tyr Leu Lys Glu Val
        290                 295                 300

Asn Val Tyr Met Tyr Leu Ala Asn Gly Ser Ala Phe Asn Ile Ser Asn
305                 310                 315                 320

Lys Asn Leu Ser Phe Trp Asp Ala Pro Leu Gly Ser Ser Tyr Met Cys
                325                 330                 335

Asn Lys Glu Gln Val Leu Ser Val Ser Arg Ala Phe Gln Ile Asn Thr
            340                 345                 350
```

```
Phe Asn Leu Lys Val Gln Pro Phe Asn Val Thr Lys Gly Gln Tyr Ser
            355                 360                 365

Thr Ala Gln Glu Cys Ser Leu Asp Asp Thr Ile Leu Ile Pro Ile
370                 375                 380

Ile Val Gly Ala Gly Leu Ser Gly Leu Ile Val Ile Val Ile Ala
385                 390                 395                 400

Tyr Leu Ile Gly Arg Arg Lys Thr Tyr Ala Gly Tyr Gln Thr Leu
                405                 410                 415

<210> SEQ ID NO 39
<211> LENGTH: 417
<212> TYPE: PRT
<213> ORGANISM: Homo sapiens

<400> SEQUENCE: 39

Met Ala Ala Pro Gly Ser Ala Arg Arg Pro Leu Leu Leu Leu Leu
1               5                   10                  15

Leu Leu Leu Leu Gly Leu Met His Cys Ala Ser Ala Ala Met Phe Met
                20                  25                  30

Val Lys Asn Gly Asn Gly Thr Ala Cys Ile Met Ala Asn Phe Ser Ala
            35                  40                  45

Ala Phe Ser Val Asn Tyr Asp Thr Lys Ser Gly Pro Lys Asn Met Thr
50                  55                  60

Phe Asp Leu Pro Ser Asp Ala Thr Val Val Leu Asn Arg Ser Ser Cys
65                  70                  75                  80

Gly Lys Glu Asn Thr Ser Asp Pro Ser Leu Val Ile Ala Phe Gly Arg
                85                  90                  95

Gly His Thr Leu Thr Leu Asn Phe Thr Arg Asn Ala Thr Arg Tyr Ser
            100                 105                 110

Val Gln Leu Met Ser Phe Val Tyr Asn Leu Ser Asp Thr His Leu Phe
        115                 120                 125

Pro Asn Ala Ser Ser Lys Glu Ile Lys Thr Val Glu Ser Ile Thr Asp
    130                 135                 140

Ile Arg Ala Asp Ile Asp Lys Lys Tyr Arg Cys Val Ser Gly Thr Gln
145                 150                 155                 160

Val His Met Asn Asn Val Thr Val Thr Leu His Asp Ala Thr Ile Gln
                165                 170                 175

Ala Tyr Leu Ser Asn Ser Ser Phe Ser Arg Gly Glu Thr Arg Cys Glu
            180                 185                 190

Gln Asp Arg Pro Ser Pro Thr Thr Ala Pro Ala Pro Pro Ser Pro
        195                 200                 205

Ser Pro Ser Pro Val Pro Lys Ser Pro Ser Val Asp Lys Tyr Asn Val
    210                 215                 220

Ser Gly Thr Asn Gly Thr Cys Leu Leu Ala Ser Met Gly Leu Gln Leu
225                 230                 235                 240

Asn Leu Thr Tyr Glu Arg Lys Asp Asn Thr Thr Val Thr Arg Leu Leu
                245                 250                 255

Asn Ile Asn Pro Asn Lys Thr Ser Ala Ser Gly Ser Cys Gly Ala His
            260                 265                 270

Leu Val Thr Leu Glu Leu His Ser Glu Gly Thr Thr Val Leu Leu Phe
        275                 280                 285

Gln Phe Gly Met Asn Ala Ser Ser Ser Arg Phe Phe Leu Gln Gly Ile
    290                 295                 300

Gln Leu Asn Thr Ile Leu Pro Asp Ala Arg Asp Pro Ala Phe Lys Ala
305                 310                 315                 320
```

-continued

```
Ala Asn Gly Ser Leu Arg Ala Leu Gln Ala Thr Val Gly Asn Ser Tyr
            325                 330                 335

Lys Cys Asn Ala Glu Glu His Val Arg Val Thr Lys Ala Phe Ser Val
        340                 345                 350

Asn Ile Phe Lys Val Trp Val Gln Ala Phe Lys Val Glu Gly Gly Gln
    355                 360                 365

Phe Gly Ser Val Glu Glu Cys Leu Leu Asp Glu Asn Ser Met Leu Ile
370                 375                 380

Pro Ile Ala Val Gly Gly Ala Leu Ala Gly Leu Val Leu Ile Val Leu
385                 390                 395                 400

Ile Ala Tyr Leu Val Gly Arg Lys Arg Ser His Ala Gly Tyr Gln Thr
                405                 410                 415

Ile

<210> SEQ ID NO 40
<211> LENGTH: 406
<212> TYPE: PRT
<213> ORGANISM: Mus musculus

<400> SEQUENCE: 40

Met Ala Ala Pro Gly Ala Arg Arg Pro Leu Leu Leu Leu Leu Leu Ala
1               5                   10                  15

Gly Leu Ala His Gly Ala Ser Ala Leu Phe Glu Val Lys Asn Asn Gly
            20                  25                  30

Thr Thr Cys Ile Met Ala Ser Phe Ser Ala Ser Phe Leu Thr Thr Tyr
        35                  40                  45

Glu Thr Ala Asn Gly Ser Gln Ile Val Asn Ile Ser Leu Pro Ala Ser
    50                  55                  60

Ala Glu Val Leu Lys Asn Gly Ser Ser Cys Gly Lys Glu Asn Val Ser
65                  70                  75                  80

Asp Pro Ser Leu Thr Ile Thr Phe Gly Arg Gly Tyr Leu Leu Thr Leu
                85                  90                  95

Asn Phe Thr Lys Asn Thr Thr Arg Tyr Ser Val Gln His Met Tyr Phe
            100                 105                 110

Thr Tyr Asn Leu Ser Asp Thr Glu His Phe Pro Asn Ala Ile Ser Lys
        115                 120                 125

Glu Ile Tyr Thr Met Asp Ser Thr Thr Asp Ile Lys Ala Asp Ile Asn
    130                 135                 140

Lys Ala Tyr Arg Cys Val Ser Asp Ile Arg Val Tyr Met Lys Asn Val
145                 150                 155                 160

Thr Val Val Leu Arg Asp Ala Thr Ile Gln Ala Tyr Leu Ser Ser Gly
                165                 170                 175

Asn Phe Ser Lys Glu Glu Thr His Cys Thr Gln Asp Gly Pro Ser Pro
            180                 185                 190

Thr Thr Gly Pro Pro Ser Pro Ser Pro Pro Leu Val Pro Thr Asn Pro
        195                 200                 205

Thr Val Ser Lys Tyr Asn Val Thr Gly Asn Asn Gly Thr Cys Leu Leu
    210                 215                 220

Ala Ser Met Ala Leu Gln Leu Asn Ile Thr Tyr Leu Lys Lys Asp Asn
225                 230                 235                 240

Lys Thr Val Thr Arg Ala Phe Asn Ile Ser Pro Asn Asp Thr Ser Ser
                245                 250                 255

Gly Ser Cys Gly Ile Asn Leu Val Thr Leu Lys Val Glu Asn Lys Asn
            260                 265                 270
```

```
Arg Ala Leu Glu Leu Gln Phe Gly Met Asn Ala Ser Ser Ser Leu Phe
            275                 280                 285

Phe Leu Gln Gly Val Arg Leu Asn Met Thr Leu Pro Asp Ala Leu Val
        290                 295                 300

Pro Thr Phe Ser Ile Ser Asn His Ser Leu Lys Ala Leu Gln Ala Thr
305                 310                 315                 320

Val Gly Asn Ser Tyr Lys Cys Asn Thr Glu Glu His Ile Phe Val Ser
                325                 330                 335

Lys Met Leu Ser Leu Asn Val Phe Ser Val Gln Val Gln Ala Phe Lys
                340                 345                 350

Val Asp Ser Asp Arg Phe Gly Ser Val Glu Glu Cys Val Gln Asp Gly
            355                 360                 365

Asn Asn Met Leu Ile Pro Ile Ala Val Gly Gly Ala Leu Ala Gly Leu
        370                 375                 380

Val Leu Ile Val Leu Ile Ala Tyr Leu Ile Gly Arg Lys Arg Ser His
385                 390                 395                 400

Ala Gly Tyr Gln Thr Ile
                405

<210> SEQ ID NO 41
<211> LENGTH: 478
<212> TYPE: PRT
<213> ORGANISM: Homo sapiens

<400> SEQUENCE: 41

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
                100                 105                 110

Ser Asn Lys Ala Tyr Val Phe Glu Arg Asp Gln Ser Val Gly Asp Pro
            115                 120                 125

Lys Ile Asp Leu Ile Arg Thr Leu Asn Ile Pro Val Leu Thr Val Ile
        130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
```

```
                225                 230                 235                 240
        Ile Thr Asp Lys Cys Asn Met Ile Asn Gly Thr Asp Gly Asp Ser Phe
                        245                 250                 255

His Pro Leu Ile Thr Lys Asp Glu Val Leu Tyr Val Phe Pro Ser Asp
                        260                 265                 270

Phe Cys Arg Ser Val Tyr Ile Thr Phe Ser Asp Tyr Glu Ser Val Gln
                        275                 280                 285

Gly Leu Pro Ala Phe Arg Tyr Lys Val Pro Ala Glu Ile Leu Ala Asn
                        290                 295                 300

Thr Ser Asp Asn Ala Gly Phe Cys Ile Pro Glu Gly Asn Cys Leu Gly
        305                 310                 315                 320

Ser Gly Val Leu Asn Val Ser Ile Cys Lys Asn Gly Ala Pro Ile Ile
                        325                 330                 335

Met Ser Phe Pro His Phe Tyr Gln Ala Asp Glu Arg Phe Val Ser Ala
                        340                 345                 350

Ile Glu Gly Met His Pro Asn Gln Glu Asp His Glu Thr Phe Val Asp
                        355                 360                 365

Ile Asn Pro Leu Thr Gly Ile Ile Leu Lys Ala Ala Lys Arg Phe Gln
                        370                 375                 380

Ile Asn Ile Tyr Val Lys Lys Leu Asp Asp Phe Val Glu Thr Gly Asp
        385                 390                 395                 400

Ile Arg Thr Met Val Phe Pro Val Met Tyr Leu Asn Glu Ser Val His
                        405                 410                 415

Ile Asp Lys Glu Thr Ala Ser Arg Leu Lys Ser Met Ile Asn Thr Thr
                        420                 425                 430

Leu Ile Ile Thr Asn Ile Pro Tyr Ile Ile Met Ala Leu Gly Val Phe
                        435                 440                 445

Phe Gly Leu Val Phe Thr Trp Leu Ala Cys Lys Gly Gln Gly Ser Met
                        450                 455                 460

Asp Glu Gly Thr Ala Asp Glu Arg Ala Pro Leu Ile Arg Thr
        465                 470                 475

<210> SEQ ID NO 42
<211> LENGTH: 478
<212> TYPE: PRT
<213> ORGANISM: Mus musculus

<400> SEQUENCE: 42

Met Gly Arg Cys Cys Phe Tyr Thr Ala Gly Thr Leu Ser Leu Leu Leu
        1               5                   10                  15

Leu Val Thr Ser Val Thr Leu Leu Val Ala Arg Val Phe Gln Lys Ala
                        20                  25                  30

Val Asp Gln Thr Ile Glu Lys Asn Met Val Leu Gln Asn Gly Thr Lys
                        35                  40                  45

Val Phe Asn Ser Trp Glu Lys Pro Pro Leu Pro Val Tyr Ile Gln Phe
                        50                  55                  60

Tyr Phe Phe Asn Val Thr Asn Pro Glu Glu Ile Leu Gln Gly Glu Ile
        65                  70                  75                  80

Pro Leu Leu Glu Glu Val Gly Pro Tyr Thr Tyr Arg Glu Leu Arg Asn
                        85                  90                  95

Lys Ala Asn Ile Gln Phe Gly Glu Asn Gly Thr Thr Ile Ser Ala Val
                        100                 105                 110

Thr Asn Lys Ala Tyr Val Phe Glu Arg Asn Gln Ser Val Gly Asp Pro
                        115                 120                 125
```

```
Asn Val Asp Leu Ile Arg Thr Ile Asn Ile Pro Leu Leu Thr Val Val
    130                 135                 140

Asp Leu Ala Gln Leu Thr Leu Leu Arg Glu Leu Ile Glu Ala Met Leu
145                 150                 155                 160

Lys Ala Tyr Gln Gln Lys Leu Phe Val Ile His Thr Val His Glu Leu
                165                 170                 175

Leu Trp Gly Tyr Lys Asp Glu Ile Leu Ser Leu Val His Ile Phe Lys
            180                 185                 190

Pro Asp Val Ser Pro Asn Phe Gly Leu Phe Tyr Glu Arg Asn Gly Thr
        195                 200                 205

Asn Asp Gly Glu Tyr Val Phe Leu Thr Gly Asp Asn Tyr Leu Asn
210                 215                 220

Phe Ser Lys Ile Val Glu Trp Asn Gly Lys Thr Ser Leu Asp Trp Trp
225                 230                 235                 240

Thr Thr Asp Thr Cys Asn Met Ile Asn Gly Thr Asp Gly Asp Ser Phe
                245                 250                 255

His Pro Leu Ile Ser Lys Asp Glu Val Leu Tyr Leu Phe Pro Ser Asp
            260                 265                 270

Leu Cys Arg Ser Val His Ile Thr Phe Ser Ser Phe Glu Asn Val Glu
        275                 280                 285

Gly Leu Pro Ala Phe Arg Tyr Lys Val Pro Ala Glu Ile Leu Ala Asn
290                 295                 300

Thr Ser Glu Asn Ala Gly Phe Cys Ile Pro Glu Gly Asn Cys Met Asp
305                 310                 315                 320

Ser Gly Val Leu Asn Ile Ser Ile Cys Lys Asn Gly Ala Pro Ile Ile
                325                 330                 335

Met Ser Phe Pro His Phe Tyr Gln Ala Asp Glu Lys Phe Val Ser Ala
            340                 345                 350

Ile Lys Gly Met His Pro Asn Lys Glu Glu His Glu Ser Phe Val Asp
        355                 360                 365

Ile Asn Pro Leu Thr Gly Ile Ile Leu Arg Gly Ala Lys Arg Phe Gln
370                 375                 380

Ile Asn Thr Tyr Val Arg Lys Leu Asp Asp Phe Val Glu Thr Gly Asp
385                 390                 395                 400

Ile Arg Thr Met Val Phe Pro Val Met Tyr Leu Asn Glu Ser Val Leu
                405                 410                 415

Ile Asp Lys Glu Thr Ala Asn Gln Leu Lys Ser Val Ile Asn Thr Thr
            420                 425                 430

Leu Val Val Thr Asn Ile Pro Tyr Ile Ile Met Ala Leu Gly Val Phe
        435                 440                 445

Phe Gly Leu Val Phe Thr Trp Leu Ala Cys Arg Gly Gln Gly Ser Met
450                 455                 460

Asp Glu Gly Thr Ala Asp Glu Arg Ala Pro Leu Ile Arg Thr
465                 470                 475

<210> SEQ ID NO 43
<211> LENGTH: 427
<212> TYPE: PRT
<213> ORGANISM: Homo sapiens

<400> SEQUENCE: 43

Met Phe Phe Thr Cys Gly Pro Asn Glu Ala Met Val Val Ser Gly Phe
1               5                   10                  15

Cys Arg Ser Pro Pro Val Met Val Ala Gly Gly Arg Val Phe Val Leu
            20                  25                  30
```

```
Pro Cys Ile Gln Gln Ile Gln Arg Ile Ser Leu Asn Thr Leu Thr Leu
         35                  40                  45

Asn Val Lys Ser Glu Lys Val Tyr Thr Arg His Gly Val Pro Ile Ser
 50                  55                  60

Val Thr Gly Ile Ala Gln Val Lys Ile Gln Gly Gln Asn Lys Glu Met
 65                  70                  75                  80

Leu Ala Ala Ala Cys Gln Met Phe Leu Gly Lys Thr Glu Ala Glu Ile
                 85                  90                  95

Ala His Ile Ala Leu Glu Thr Leu Glu Gly His Gln Arg Ala Ile Met
                100                 105                 110

Ala His Met Thr Val Glu Glu Ile Tyr Lys Asp Arg Gln Lys Phe Ser
                115                 120                 125

Glu Gln Val Phe Lys Val Ala Ser Ser Asp Leu Val Asn Met Gly Ile
130                 135                 140

Ser Val Val Ser Tyr Thr Leu Lys Asp Ile His Asp Asp Gln Asp Tyr
145                 150                 155                 160

Leu His Ser Leu Gly Lys Ala Arg Thr Ala Gln Val Gln Lys Asp Ala
                165                 170                 175

Arg Ile Gly Glu Ala Glu Ala Lys Arg Asp Ala Gly Ile Arg Glu Ala
                180                 185                 190

Lys Ala Lys Gln Glu Lys Val Ser Ala Gln Tyr Leu Ser Glu Ile Glu
195                 200                 205

Met Ala Lys Ala Gln Arg Asp Tyr Glu Leu Lys Lys Ala Ala Tyr Asp
210                 215                 220

Ile Glu Val Asn Thr Arg Arg Ala Gln Ala Asp Leu Ala Tyr Gln Leu
225                 230                 235                 240

Gln Val Ala Lys Thr Lys Gln Gln Ile Glu Glu Gln Arg Val Gln Val
                245                 250                 255

Gln Val Val Glu Arg Ala Gln Gln Val Ala Val Gln Glu Gln Glu Ile
                260                 265                 270

Ala Arg Arg Glu Lys Glu Leu Glu Ala Arg Val Arg Lys Pro Ala Glu
                275                 280                 285

Ala Glu Arg Tyr Lys Leu Glu Arg Leu Ala Glu Ala Glu Lys Ser Gln
                290                 295                 300

Leu Ile Met Gln Ala Glu Ala Glu Ala Ala Ser Val Arg Met Arg Gly
305                 310                 315                 320

Glu Ala Glu Ala Phe Ala Ile Gly Ala Arg Ala Arg Ala Glu Ala Glu
                325                 330                 335

Gln Met Ala Lys Lys Ala Glu Ala Phe Gln Leu Tyr Gln Glu Ala Ala
                340                 345                 350

Gln Leu Asp Met Leu Leu Glu Lys Leu Pro Gln Val Ala Glu Glu Ile
                355                 360                 365

Ser Gly Pro Leu Thr Ser Ala Asn Lys Ile Thr Leu Val Ser Ser Gly
370                 375                 380

Ser Gly Thr Met Gly Ala Ala Lys Val Thr Gly Glu Val Leu Asp Ile
385                 390                 395                 400

Leu Thr Arg Leu Pro Glu Ser Val Glu Arg Leu Thr Gly Val Ser Ile
                405                 410                 415

Ser Gln Val Asn His Lys Pro Leu Arg Thr Ala
                420                 425

<210> SEQ ID NO 44
<211> LENGTH: 428
```

<212> TYPE: PRT
<213> ORGANISM: Mus musculus

<400> SEQUENCE: 44

```
Met Phe Phe Thr Cys Gly Pro Asn Glu Ala Met Val Val Ser Gly Phe
1               5                   10                  15

Cys Arg Ser Pro Pro Val Met Val Ala Gly Gly Arg Val Phe Val Leu
            20                  25                  30

Pro Cys Ile Gln Gln Ile Gln Arg Ile Ser Leu Asn Thr Leu Thr Leu
        35                  40                  45

Asn Val Lys Ser Glu Lys Val Tyr Thr Arg His Gly Val Pro Ile Ser
    50                  55                  60

Val Thr Gly Ile Ala Gln Val Lys Ile Gln Gly Gln Asn Lys Glu Met
65                  70                  75                  80

Leu Ala Ala Ala Cys Gln Met Phe Leu Gly Lys Thr Glu Ala Glu Ile
                85                  90                  95

Ala His Ile Ala Leu Glu Thr Leu Glu Gly His Gln Arg Ala Ile Met
            100                 105                 110

Ala His Met Thr Val Glu Glu Ile Tyr Lys Asp Arg Gln Lys Phe Ser
        115                 120                 125

Glu Gln Val Phe Lys Val Ala Ser Ser Asp Leu Val Asn Met Gly Ile
    130                 135                 140

Ser Val Val Ser Tyr Thr Leu Lys Asp Ile His Asp Asp Gln Asp Tyr
145                 150                 155                 160

Leu His Ser Leu Gly Lys Ala Arg Thr Ala Gln Val Gln Lys Asp Ala
                165                 170                 175

Arg Ile Gly Glu Ala Glu Ala Lys Arg Asp Ala Gly Ile Arg Glu Ala
            180                 185                 190

Lys Ala Lys Gln Glu Lys Val Ser Ala Gln Cys Leu Ser Glu Ile Glu
        195                 200                 205

Met Ala Lys Ala Gln Arg Asp Tyr Glu Leu Lys Lys Ala Thr Tyr Asp
    210                 215                 220

Ile Glu Val Asn Thr Arg Arg Ala Gln Ala Asp Leu Ala Tyr Gln Leu
225                 230                 235                 240

Gln Val Ala Lys Thr Lys Gln Gln Ile Glu Glu Gln Arg Val Gln Val
                245                 250                 255

Gln Val Val Glu Arg Ala Gln Gln Val Ala Val Gln Glu Gln Glu Ile
            260                 265                 270

Ala Arg Arg Glu Lys Glu Leu Glu Ala Arg Val Arg Lys Pro Ala Glu
        275                 280                 285

Ala Glu Arg Tyr Arg Leu Glu Arg Leu Ala Glu Ala Glu Lys Ala Gln
    290                 295                 300

Leu Ile Met Gln Ala Glu Ala Glu Ala Glu Ser Val Arg Met Arg Gly
305                 310                 315                 320

Glu Ala Glu Ala Phe Ala Ile Gly Ala Arg Ala Arg Ala Glu Ala Glu
                325                 330                 335

Gln Met Ala Lys Lys Ala Glu Ala Phe Gln Met Tyr Gln Glu Ala Ala
            340                 345                 350

Gln Leu Asp Met Leu Leu Glu Lys Leu Pro Gln Val Ala Glu Glu Ile
        355                 360                 365

Ser Gly Pro Leu Thr Ser Ala Asn Lys Ile Thr Leu Val Ser Ser Gly
    370                 375                 380

Ser Gly Thr Met Gly Ala Ala Lys Val Thr Gly Glu Val Leu Asp Ile
385                 390                 395                 400
```

```
Leu Ser Arg Leu Pro Glu Ser Val Glu Arg Leu Thr Gly Val Ser Ile
                405                 410                 415

Ser Gln Val Asn His Asn Lys Pro Leu Arg Thr Ala
            420                 425

<210> SEQ ID NO 45
<211> LENGTH: 524
<212> TYPE: PRT
<213> ORGANISM: Artificial Sequence
<220> FEATURE:
<223> OTHER INFORMATION: Synthetic construct

<400> SEQUENCE: 45

Met Val Pro Gln Val Leu Leu Phe Val Leu Leu Gly Phe Ser Leu
1               5                   10                  15

Cys Phe Gly Lys Phe Pro Ile Tyr Thr Ile Pro Asp Lys Leu Gly Pro
                20                  25                  30

Trp Ser Pro Ile Asp Ile His His Leu Arg Cys Pro Asn Asn Leu Val
                35                  40                  45

Val Glu Asp Glu Gly Cys Thr Asn Leu Ser Gly Phe Ser Tyr Met Glu
50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
                115                 120                 125

Glu Ser Leu Gln Asn Pro Tyr Pro Asp Tyr His Trp Leu Arg Thr Val
            130                 135                 140

Arg Thr Thr Lys Glu Ser Leu Ile Ile Ser Pro Ser Val Thr Asp Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
                180                 185                 190

Asp Tyr Thr Ile Trp Met Pro Glu Asn Pro Arg Pro Gly Thr Pro Cys
                195                 200                 205

Asp Ile Phe Thr Asn Ser Arg Gly Lys Arg Ala Ser Asn Gly Asn Lys
            210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Ser
                260                 265                 270

Pro Asp Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
            290                 295                 300

Thr Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335
```

```
Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Lys Val Gly Gly
            355                 360                 365

Arg Cys His Pro His Val Asn Gly Val Phe Phe Asn Gly Ile Ile Leu
            370                 375                 380

Gly Pro Asp Asp Arg Val Leu Ile Pro Glu Met Gln Ser Ser Leu Leu
385                 390                 395                 400

Arg Gln His Met Glu Leu Leu Glu Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Pro Asp Val Tyr Lys Gln Ile Ser Gly
            435                 440                 445

Val Asp Leu Gly Leu Pro Asn Trp Gly Lys Tyr Val Leu Met Thr Ala
            450                 455                 460

Gly Ala Met Ile Gly Leu Val Leu Ile Phe Ser Leu Met Thr Trp Cys
465                 470                 475                 480

Arg Arg Ala Asn Arg Pro Glu Ser Lys Gln Arg Ser Phe Gly Gly Thr
                485                 490                 495

Gly Gly Asn Val Ser Val Thr Ser Gln Ser Gly Lys Val Ile Pro Ser
            500                 505                 510

Trp Glu Ser Tyr Lys Ser Gly Gly Glu Ile Arg Leu
            515                 520

<210> SEQ ID NO 46
<211> LENGTH: 43
<212> TYPE: PRT
<213> ORGANISM: Artificial Sequence
<220> FEATURE:
<223> OTHER INFORMATION: Synthetic construct

<400> SEQUENCE: 46

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu Gly Gly Gly Gly Thr
            20                  25                  30

His Arg Pro Pro Met Trp Ser Pro Val Trp Pro
            35                  40

<210> SEQ ID NO 47
<211> LENGTH: 146
<212> TYPE: PRT
<213> ORGANISM: Saccharomyces cerevisiae

<400> SEQUENCE: 47

Lys Leu Leu Ser Ser Ile Glu Gln Ala Cys Asp Ile Cys Arg Leu Lys
1               5                   10                  15

Lys Leu Lys Cys Ser Lys Glu Lys Pro Lys Cys Ala Lys Cys Leu Lys
            20                  25                  30

Asn Asn Trp Glu Cys Arg Tyr Ser Pro Lys Thr Lys Arg Ser Pro Leu
            35                  40                  45

Thr Arg Ala His Leu Thr Glu Val Glu Ser Arg Leu Glu Arg Leu Glu
        50                  55                  60

Gln Leu Phe Leu Leu Ile Phe Pro Arg Glu Asp Leu Asp Met Ile Leu
65                  70                  75                  80
```

```
Lys Met Asp Ser Leu Gln Asp Ile Lys Ala Leu Leu Thr Gly Leu Phe
            85                  90                  95

Val Gln Asp Asn Val Asn Lys Asp Ala Val Thr Asp Arg Leu Ala Ser
        100                 105                 110

Val Glu Thr Asp Met Pro Leu Thr Leu Arg Gln His Arg Ile Ser Ala
        115                 120                 125

Thr Ser Ser Ser Glu Glu Ser Ser Asn Lys Gly Gln Arg Gln Leu Thr
        130                 135                 140

Val Ser
145

<210> SEQ ID NO 48
<211> LENGTH: 766
<212> TYPE: PRT
<213> ORGANISM: Artificial Sequence
<220> FEATURE:
<223> OTHER INFORMATION: Synthetic construct

<400> SEQUENCE: 48

Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30

Val Gly His Gly Phe Thr His Ala His Ile Val Ala Leu Ser Gln His
        35                  40                  45

Pro Ala Ala Leu Gly Thr Val Ala Val Lys Tyr Gln Asp Met Ile Ala
    50                  55                  60

Ala Leu Pro Glu Ala Thr His Glu Ala Ile Val Gly Val Gly Lys Gln
65                  70                  75                  80

Trp Ser Gly Ala Arg Ala Leu Glu Ala Leu Leu Thr Val Ala Gly Glu
                85                  90                  95

Leu Arg Gly Pro Pro Leu Gln Leu Asp Thr Gly Gln Leu Leu Lys Ile
            100                 105                 110

Ala Lys Arg Gly Gly Val Thr Ala Val Glu Ala Val His Ala Trp Arg
        115                 120                 125

Asn Ala Leu Thr Gly Ala Pro Leu Asn Leu Thr Pro Asp Gln Val Val
        130                 135                 140

Ala Ile Ala Ser His Asp Gly Gly Lys Gln Ala Leu Glu Thr Val Gln
145                 150                 155                 160

Arg Leu Leu Pro Val Leu Cys Gln Asp His Gly Leu Thr Pro Glu Gln
                165                 170                 175

Val Val Ala Ile Ala Asn Asn Asn Gly Gly Lys Gln Ala Leu Glu Thr
                180                 185                 190

Val Gln Arg Leu Leu Pro Val Leu Cys Gln Ala His Gly Leu Thr Pro
        195                 200                 205

Asp Gln Val Val Ala Ile Ala Ser His Asp Gly Gly Lys Gln Ala Leu
    210                 215                 220

Glu Thr Val Gln Arg Leu Leu Pro Val Leu Cys Gln Ala His Gly Leu
225                 230                 235                 240

Thr Pro Ala Gln Val Val Ala Ile Ala Ser Asn Gly Gly Gly Lys Gln
                245                 250                 255

Ala Leu Glu Thr Val Gln Arg Leu Leu Pro Val Leu Cys Gln Asp His
                260                 265                 270

Gly Leu Thr Pro Asp Gln Val Val Ala Ile Ala Ser His Asp Gly Gly
            275                 280                 285
```

```
Lys Gln Ala Leu Glu Thr Val Gln Arg Leu Leu Pro Val Leu Cys Gln
290                 295                 300

Asp His Gly Leu Thr Pro Glu Gln Val Val Ala Ile Ala Asn Asn Asn
305                 310                 315                 320

Gly Gly Lys Gln Ala Leu Glu Thr Val Gln Arg Leu Leu Pro Val Leu
                325                 330                 335

Cys Gln Ala His Gly Leu Thr Pro Asp Gln Val Val Ala Ile Ala Ser
                340                 345                 350

Asn Ile Gly Gly Lys Gln Ala Leu Glu Thr Val Gln Arg Leu Leu Pro
            355                 360                 365

Val Leu Cys Gln Ala His Gly Leu Thr Pro Ala Gln Val Val Ala Ile
370                 375                 380

Ala Ser His Asp Gly Gly Lys Gln Ala Leu Glu Thr Val Gln Arg Leu
385                 390                 395                 400

Leu Pro Val Leu Cys Gln Asp His Gly Leu Thr Pro Asp Gln Val Val
                405                 410                 415

Ala Ile Ala Asn Asn Asn Gly Gly Lys Gln Ala Leu Glu Thr Val Gln
                420                 425                 430

Arg Leu Leu Pro Val Leu Cys Gln Asp His Gly Leu Thr Pro Glu Gln
                435                 440                 445

Val Val Ala Ile Ala Ser Asn Gly Gly Gly Lys Gln Ala Leu Glu Thr
450                 455                 460

Val Gln Arg Leu Leu Pro Val Leu Cys Gln Ala His Gly Leu Thr Pro
465                 470                 475                 480

Asp Gln Val Val Ala Ile Ala Ser Asn Ile Gly Gly Lys Gln Ala Leu
                485                 490                 495

Glu Thr Val Gln Arg Leu Leu Pro Val Leu Cys Gln Ala His Gly Leu
                500                 505                 510

Thr Pro Ala Gln Val Val Ala Ile Ala Ser His Asp Gly Gly Lys Gln
                515                 520                 525

Ala Leu Glu Thr Val Gln Arg Leu Leu Pro Val Leu Cys Gln Asp His
530                 535                 540

Gly Leu Thr Pro Asp Gln Val Val Ala Ile Ala Asn Asn Asn Gly Gly
545                 550                 555                 560

Lys Gln Ala Leu Glu Thr Val Gln Arg Leu Leu Pro Val Leu Cys Gln
                565                 570                 575

Asp His Gly Leu Thr Pro Glu Gln Val Val Ala Ile Ala Ser His Asp
                580                 585                 590

Gly Gly Lys Gln Ala Leu Glu Thr Val Gln Arg Leu Leu Pro Val Leu
            595                 600                 605

Cys Gln Ala His Gly Leu Thr Pro Asp Gln Val Val Ala Ile Ala Ser
610                 615                 620

Asn Gly Gly Gly Lys Gln Ala Leu Glu Thr Val Gln Arg Leu Leu Pro
625                 630                 635                 640

Val Leu Cys Gln Ala His Gly Leu Thr Pro Ala Gln Val Val Ala Ile
                645                 650                 655

Ala Ser His Asp Gly Gly Lys Gln Ala Leu Glu Thr Val Gln Arg Leu
                660                 665                 670

Leu Pro Val Leu Cys Gln Asp His Gly Leu Thr Pro Glu Gln Val Val
                675                 680                 685

Ala Ile Ala Asn Asn Asn Gly Gly Arg Pro Ala Leu Glu Ser Ile Val
                690                 695                 700

Ala Gln Leu Ser Arg Pro Asp Pro Ala Leu Ala Ala Leu Thr Asn Asp
```

```
                705                 710                 715                 720
His Leu Val Ala Leu Ala Cys Leu Gly Gly Arg Pro Ala Leu Asp Ala
                    725                 730                 735

Val Lys Lys Gly Leu Pro His Ala Pro Ala Leu Ile Lys Arg Thr Asn
                740                 745                 750

Arg Arg Ile Pro Glu Arg Thr Ser His Arg Val Ala Gly Ser
                755                 760                 765

<210> SEQ ID NO 49
<211> LENGTH: 356
<212> TYPE: PRT
<213> ORGANISM: Homo sapiens

<400> SEQUENCE: 49

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
                20                  25                  30

Glu His Glu Ala Asp Lys Lys Glu Asp Asp Leu Glu Thr Met Asn Ala
            35                  40                  45

Glu Glu Asp Ser Leu Arg Asn Gly Gly Glu Glu Asp Glu Asp
        50                  55                  60

Asp Leu Glu Glu Glu Glu Glu Glu Glu Asp Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320
```

Thr Ala Ala Pro Arg Cys Glu Ile Pro Ile Asp Asn Ile Met Ser Phe
               325                 330                 335

Asp Ser His Ser His His Glu Arg Val Met Ser Ala Gln Leu Asn Ala
           340                 345                 350

Ile Phe His Asp
        355

<210> SEQ ID NO 50
<211> LENGTH: 357
<212> TYPE: PRT
<213> ORGANISM: Mus musculus

<400> SEQUENCE: 50

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Glu Leu Glu Ala Met Asn Ala
        35                  40                  45

Glu Glu Asp Ser Leu Arg Asn Gly Gly Glu Glu Glu Glu Asp Glu
    50                  55                  60

Asp Leu Glu Glu Glu Glu Glu Glu Glu Glu Glu Glu Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Pro Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Pro Gln Ser His Gly Ser Ile Phe Ser Ser
305                 310                 315                 320

Gly Ala Ala Ala Pro Arg Cys Glu Ile Pro Ile Asp Asn Ile Met Ser
                325                 330                 335

```
Phe Asp Ser His Ser His His Glu Arg Val Met Ser Ala Gln Leu Asn
                340                 345                 350

Ala Ile Phe His Asp
        355

<210> SEQ ID NO 51
<211> LENGTH: 317
<212> TYPE: PRT
<213> ORGANISM: Homo sapiens

<400> SEQUENCE: 51

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
        50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 52
<211> LENGTH: 319
<212> TYPE: PRT
```

<213> ORGANISM: Mus musculus

<400> SEQUENCE: 52

Met Tyr Asn Met Met Glu Thr Glu Leu Lys Pro Pro Gly Pro Gln Gln
1               5                   10                  15

Ala Ser Gly Gly Gly Gly Gly Gly Asn Ala Thr Ala Ala Ala Thr
            20                  25                  30

Gly Gly Asn Gln Lys Asn Ser Pro Asp Arg Val Lys Arg Pro Met Asn
            35                  40                  45

Ala Phe Met Val Trp Ser Arg Gly Gln Arg Arg Lys Met Ala Gln Glu
    50                  55                  60

Asn Pro Lys Met His Asn Ser Glu Ile Ser Lys Arg Leu Gly Ala Glu
65                  70                  75                  80

Trp Lys Leu Leu Ser Glu Thr Glu Lys Arg Pro Phe Ile Asp Glu Ala
                85                  90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
            115                 120                 125

Leu Pro Gly Gly Leu Leu Ala Pro Gly Gly Asn Ser Met Ala Ser Gly
            130                 135                 140

Val Gly Val Gly Ala Gly Leu Gly Gly Leu Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Val Val Ser Ala Leu Gln
            195                 200                 205

Tyr Asn Ser Met Thr Ser Ser Gln Thr Tyr Met Asn Gly Ser Pro Thr
            210                 215                 220

Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Pro Pro Val
                245                 250                 255

Val Thr Ser Ser His Ser Arg Ala Pro Cys Gln Ala Gly Asp Leu
            260                 265                 270

Arg Asp Met Ile Ser Met Tyr Leu Pro Gly Ala Glu Val Pro Glu Pro
            275                 280                 285

Ala Ala Pro Ser Arg Leu His Met Ala Gln His Tyr Gln Ser Gly Pro
    290                 295                 300

Val Pro Gly Thr Ala Lys Tyr Gly Thr Leu Pro Leu Ser His Met
305                 310                 315

<210> SEQ ID NO 53
<211> LENGTH: 239
<212> TYPE: PRT
<213> ORGANISM: Aequorea victoria

<400> SEQUENCE: 53

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile

-continued

```
                35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 54
<211> LENGTH: 162
<212> TYPE: PRT
<213> ORGANISM: Synechocystis sp. PCC6803

<400> SEQUENCE: 54

Cys Pro Gly Cys Leu Ser Phe Gly Thr Glu Ile Leu Thr Val Glu Tyr
 1               5                  10                  15

Gly Pro Leu Pro Ile Gly Lys Ile Val Ser Glu Ile Asn Cys Ser
                20                  25                  30

Val Tyr Ser Val Asp Pro Glu Gly Arg Val Tyr Thr Gln Ala Ile Ala
             35                  40                  45

Gln Trp His Asp Arg Gly Glu Gln Glu Val Leu Glu Tyr Glu Leu Glu
 50                  55                  60

Asp Gly Ser Val Ile Arg Ala Thr Ser Asp His Arg Phe Leu Thr Thr
 65                  70                  75                  80

Asp Tyr Gln Leu Leu Ala Ile Glu Glu Ile Phe Ala Arg Gln Leu Asp
                 85                  90                  95

Leu Leu Thr Leu Glu Asn Ile Lys Gln Thr Glu Glu Ala Leu Asp Asn
                100                 105                 110

His Arg Leu Pro Phe Pro Leu Leu Asp Ala Gly Thr Ile Lys Met Val
            115                 120                 125

Lys Val Ile Gly Arg Arg Ser Leu Gly Val Gln Arg Ile Phe Asp Ile
130                 135                 140

Gly Leu Pro Gln Asp His Asn Phe Leu Leu Ala Asn Gly Ala Ile Ala
145                 150                 155                 160

Ala Ala
```

<210> SEQ ID NO 55
<211> LENGTH: 137
<212> TYPE: PRT
<213> ORGANISM: Nostoc punctiforme

<400> SEQUENCE: 55

Cys Pro Gly Cys Leu Ser Tyr Glu Thr Glu Ile Leu Thr Val Glu Tyr
1               5                   10                  15

Gly Leu Leu Pro Ile Gly Lys Ile Val Glu Lys Arg Ile Glu Cys Thr
                20                  25                  30

Val Tyr Ser Val Asp Asn Asn Gly Asn Ile Tyr Thr Gln Pro Val Ala
            35                  40                  45

Gln Trp His Asp Arg Gly Glu Gln Glu Val Phe Glu Tyr Cys Leu Glu
    50                  55                  60

Asp Gly Ser Leu Ile Arg Ala Thr Lys Asp His Lys Phe Met Thr Val
65                  70                  75                  80

Asp Gly Gln Met Leu Pro Ile Asp Glu Ile Phe Glu Arg Glu Leu Asp
                85                  90                  95

Leu Met Arg Val Asp Asn Ile Lys Ile Ala Thr Arg Lys Tyr Leu Gly
                100                 105                 110

Lys Gln Asn Val Tyr Asp Ile Gly Val Glu Arg Asp His Asn Phe Ala
            115                 120                 125

Leu Lys Asn Gly Phe Ile Ala Ser Ala
    130                 135

<210> SEQ ID NO 56
<211> LENGTH: 160
<212> TYPE: PRT
<213> ORGANISM: Penicillium chrysogenum

<400> SEQUENCE: 56

Cys Pro Gly Cys Leu Ala Lys Gly Thr Arg Leu Leu Arg Cys Asp Gly
1               5                   10                  15

Thr Glu Ile Asn Val Glu Asp Val Arg Glu Gly Asp Leu Leu Leu Gly
                20                  25                  30

Pro Asp Gly Glu Pro Arg Arg Ala Phe Asn Ile Val Asn Gly Ile Asp
            35                  40                  45

Arg Leu Tyr Arg Ile Lys Ile Gly Gly Glu Lys Glu Asp Leu Val Val
    50                  55                  60

Thr Pro Asn His Ile Leu Val Leu Tyr Arg Glu Asp Gly Ser Lys Asn
65                  70                  75                  80

Val Glu Lys Gln Thr Val Glu Ile Thr Ala Ala Glu Phe Ala Ala Leu
                85                  90                  95

Ser Thr Glu Glu Arg Ser Leu Tyr Ser Ala Phe Thr Ser Pro Arg Ala
                100                 105                 110

Glu Lys Gly Ala Asp Asp Ser Ala Gln Thr His Ser Phe Lys Ile Glu
            115                 120                 125

Gln Val Ser Leu Glu Ser Glu Lys Thr Glu Trp Ala Gly Phe Arg Val
    130                 135                 140

Asp Lys Asp Gln Leu Tyr Leu Arg His Asp Tyr Leu Val Leu His Ala
145                 150                 155                 160

<210> SEQ ID NO 57
<211> LENGTH: 32
<212> TYPE: PRT
<213> ORGANISM: Artificial Sequence
<220> FEATURE:
<223> OTHER INFORMATION: Synthetic construct

```
-continued

<400> SEQUENCE: 57

Arg Lys Arg Lys Arg Arg Gly Gly Gly Ser Gly Gly Ser Gly Gly Ser
1               5                   10                  15

Gly Gly Ser Gly Gly Ser Gly Gly Ser Gly Arg Ser Arg Lys Arg Arg
            20                  25                  30

<210> SEQ ID NO 58
<211> LENGTH: 7
<212> TYPE: PRT
<213> ORGANISM: Artificial Sequence
<220> FEATURE:
<223> OTHER INFORMATION: Synthetic construct

<400> SEQUENCE: 58

Pro Lys Lys Lys Arg Lys Val
1               5
```